(12) United States Patent
Lu et al.

(10) Patent No.: US 10,955,496 B2
(45) Date of Patent: Mar. 23, 2021

(54) GAS-FILLED STRUCTURES AND RELATED COMPOSITIONS, METHODS AND SYSTEMS FOR MAGNETIC RESONANCE IMAGING

(71) Applicant: CALIFORNIA INSTITUTE OF TECHNOLOGY, Pasadena, CA (US)

(72) Inventors: George J. Lu, Pasadena, CA (US); Mikhail G. Shapiro, Los Angeles, CA (US); Arash Farhadi, Pasadena, CA (US); Jerzy O. Szablowski, Sherman Village, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 624 days.

(21) Appl. No.: 15/663,600

(22) Filed: Jul. 28, 2017

(65) Prior Publication Data
US 2018/0038922 A1 Feb. 8, 2018

Related U.S. Application Data

(60) Provisional application No. 62/367,750, filed on Jul. 28, 2016.

(51) Int. Cl.
| | | |
|---|---|---|
| *G01R 33/28* | (2006.01) | |
| *A61B 5/055* | (2006.01) | |
| *G01R 33/50* | (2006.01) | |
| *A61B 8/08* | (2006.01) | |
| *G01R 33/48* | (2006.01) | |

(Continued)

(52) U.S. Cl.
CPC ............ *G01R 33/281* (2013.01); *A61B 5/055* (2013.01); *A61B 8/4416* (2013.01); *A61B 8/481* (2013.01); *A61B 8/5261* (2013.01); *G01R 33/4814* (2013.01); *G01R 33/50* (2013.01); *G01R 33/5601* (2013.01); *G01R 33/5602* (2013.01)

(58) Field of Classification Search
CPC .............. G01R 33/281; G01R 33/5601; G01R 33/5602; G01R 33/50; G01R 33/4814; A61B 8/4416; A61B 5/055; A61B 8/481; A61B 8/5261
See application file for complete search history.

(56) References Cited

U.S. PATENT DOCUMENTS

| | | |
|---|---|---|
| 7,498,024 B2 | 3/2009 | Fang et al. |
| 10,493,172 B2 | 12/2019 | Lakshmanan et al. |

(Continued)

FOREIGN PATENT DOCUMENTS

| | | |
|---|---|---|
| CN | 105232045 A | 1/2016 |
| WO | 2007/014162 A2 | 2/2007 |

(Continued)

OTHER PUBLICATIONS

Abdul-Rahman, H.S. et al., "Fast and Robust Three-Dimensional Best Path Phase Unwrapping Algorithm." Appl. Optics, vol. 46, No. 26, pp. 6623-6635, (2007), 13 pages.

(Continued)

*Primary Examiner* — Sanjay Cattungal
(74) *Attorney, Agent, or Firm* — Steinfl + Bruno, LLP

(57) ABSTRACT

Gas vesicle protein structures and related compositions, methods, and systems for singleplexed and/or multiplexed magnetic resonance imaging of a target site alone or in combination with ultrasound are described, in which the gas vesicle protein structures provide contrast for the imaging.

33 Claims, 24 Drawing Sheets

(51) Int. Cl.
   G01R 33/56    (2006.01)
   A61B 8/00     (2006.01)

(56) References Cited

U.S. PATENT DOCUMENTS

| | | | |
|---|---|---|---|
| 2003/0157025 A1 | 8/2003 | Unger et al. | |
| 2005/0058605 A1 | 3/2005 | Schneider et al. | |
| 2006/0216810 A1 | 9/2006 | Ju | |
| 2014/0288411 A1* | 9/2014 | Shapiro | A61K 49/1809 600/420 |
| 2014/0288421 A1* | 9/2014 | Shapiro | A61B 8/481 600/431 |
| 2016/0220672 A1 | 8/2016 | Chalasani et al. | |
| 2018/0028693 A1 | 2/2018 | Lakshmanan et al. | |
| 2018/0030501 A1* | 2/2018 | Bourdeau | C07K 14/32 |
| 2020/0164095 A1* | 5/2020 | Lakshmanan | A61K 49/0002 |
| 2020/0237346 A1 | 7/2020 | Sawyer et al. | |
| 2020/0291409 A1 | 9/2020 | Farhadi et al. | |

FOREIGN PATENT DOCUMENTS

| | | |
|---|---|---|
| WO | 2012/038950 A1 | 3/2012 |
| WO | 2018/069788 A1 | 4/2018 |
| WO | 2020/146367 A1 | 7/2020 |
| WO | 2020/146379 A1 | 7/2020 |

OTHER PUBLICATIONS

Ahrens, E.T., et al., "Tracking Immune Cells In Vivo Using Magnetic Resonance Imaging", Nature Reviews: Immunology, 13(10), pp. 755-763, (2013), 19 pages.

Atanasijevic, T. et al., "Calcium-Sensitive MRI Contrast Agents Based on Superparamagnetic Iron Oxide Nanoparticles and Calmodulin", Proceedings of the National Academy of Sciences, vol. 103, No. 40, pp. 14707-14712, (2006), 6 pages.

Barrett, T. et al., "MRI of Tumor Angiogenesis", Journal of Magnetic Resonance Imaging 26, pp. 235-249, (2007), 15 pages.

Blanco, E., et al., "Principles of Nanoparticle Design for Overcoming Biological Barriers to Drug Delivery", Nature Biotechnology, 33(9), pp. 941-951, (2015), 11 pages.

Bowen, C.V. et al., "Application of the Static Dephasing Regime Theory to Superparamagnetic Iron-Oxide Loaded Cells", Magnetic Resonance in Medicine, 48(1), pp. 52-61, (2002), 10 pages.

Brock, R., "The Uptake of Arginine-Rich Cell-Penetrating Peptides: Putting the Puzzle Together", Bioconjurate Chemistry, vol. 25(5), pp. 863-868, (2014), 6 pages.

Brooks, R.A. et al., "On $T_2$-shortening by Weakly Magnetized Particles: The Chemical Exchange Model", Magnetic Resonance in Medicine, 45(6), pp. 1014-1020, (2001), 7 pages.

Buchholz, B., et al., "The Distribution of the Outer Gas Vesicle Protein, GvpC, on the *Anabaena* Gas Vesicle, and its Ratio to GvpA", Journal of General Microbiology 139(10), pp. 2353-2363, (1993), 11 pages.

Burns, P.N., "Harmonic Imaging with Ultrasound Contrast Agents", Clinical Radiology, 51, Suppl. 1, pp. 50-55, (1996), 7 pages.

Caravan, P. et al., "Gadolinium(III) Chelates as MRI Contrast Agents: Structure, Dynamics, and Applications." Chemical Reviews 99(9), pp. 2293-2352, (1999), 60 pages.

Cherin, E., et al., "Acoustic Behavior of *Halobacterium salinarum* Gas Vesicles in the High-Frequency Range: Experiments and Modeling", Ultrasound in Med. & Biol., vol. 43, No. 5, pp. 1016-1030, (2016), 17 pages.

Choi, J.J. et al., "Noninvasive, Transcranial and Localized Opening of the Blood-Brain Barrier Using Focused Ultrasound in Mice", Ultrasound in Medicine & Biology, vol. 33, No. 1, pp. 95-104, (2007), 10 pages.

Cohen, B. et al., "MRI Detection of Transcriptional Regulation of Gene Expression in Transgenic Mice", Nat Med, 13(4), pp. 498-503, (2007), 6 pages.

Cohen, B. et al., "Ferritin as an Endogenous MRI Reporter for Noninvasive Imaging of Gene Expression in C6 Glioma Tumors", Neoplasia vol. 7, No. 2, pp. 109-117, (2005), 9 pages.

Cosgrove, D., et al., "Clinical Uses of Microbubbles in Diagnosis and Treatment", Med. Biol. Eng. Comput., 47, pp. 813-826, (2009), 14 pages.

Cunningham, C.H. et al., "Positive Contrast Magnetic Resonance Imaging of Cells Labeled with Magnetic Nanoparticles", Magnetic Resonance in Medicine, 53(5), pp. 999-1005, (2005), 7 pages.

DasSarma, S., et al., "An Improved Genetic System for Bioengineering Buoyant Gas Vesicle Nanoparticles from Haloarchaea", BMC Biotechnol., vol. 13(112), (2013), 10 pages.

Dawson, P.E., et al., "Synthesis of Proteins by Native Chemical Ligation", Science, vol. 266(5186), pp. 776-779, (1994), 5 pages.

Donaldson, G.P. et al., "Gut Biogeography of the Bacterial Microbiota", Nature Reviews Microbiology, vol. 14 (1), pp. 20-32, (2016), 31 pages.

Errico, C., et al., "Ultrafast Ultrasound Localization Microscopy for Deep Super-Resolution Vascular Imaging", Nature, vol. 527, pp. 499-502, (2015), 9 pages.

Ferrara, K., et al., "Ultrasound Microbubble Contrast Agents: Fundamentals and Application to Gene and Drug Delivery", Annu. Rev. Biomed. Eng., vol. 9, pp. 415-447, (2017), 35 pages.

Fischer, H. et al., "Average Protein Density is a Molecular-Weight-Dependent Function", Protein Science, vol. 13, pp. 2825-2828, (2004), 4 pages.

Genove, G. et al., "A New Transgene Reporter for In Vivo Magnetic Resonance Imaging", Nat Med, vol. 11, No. 4, pp. 450-454, (2005), 5 pages.

Gilad, A.A. et al., "Artificial Reporter Gene Providing MRI Contrast Based on Proton Exchange", Nat Biotech, vol. 25, No. 2, pp. 217-219, (2007), 3 pages.

Gilad, A.A. et al. "Review Article: Developing MR Reporter Genes: Promises and Pitfalls", NMR in Biomedicine 20, pp. 275-290, (2007), 16 pages.

Gilad, A.A. et al., "MRI Reporter Genes", Journal of Nuclear Medicine, vol. 49, No. 12, pp. 1905-1908, (2008), 9 pages.

Gillis, P. et al., "On $T_2$-Shortening by Strongly Magnetized Spheres: A Partial Refocusing Model", Magnetic Resonance in Medicine, 47(2), pp. 257-263, (2002), 7 pages.

Gillis, P. et al., "Transverse Relaxation of Solvent Protons Induced by Magnetized Spheres: Application to Ferritin, Erythrocytes, and Magnetite", Magnetic Resonance in Medicine 5, pp. 323-345, (1987), 23 pages.

Haacke, E.M. et al., "Susceptibility-Weighted Imaging: Technical Aspects and Clinical Applications," Part 1. American Journal of Neuroradiology 30 (1), pp. 19-30, (2009), 29 pages.

Hayes, P.K., Walsby, A.E. & Walker, J.E., "Complete Amino Acid Sequence of Cyanobacterial Gas-Vesicle Protein Indicates a 70-Residue Molecule that Corresponds in Size to the Crystallographic Unit Cell", Biochemical Journal, 236, pp. 31-36, (1986), 6 pages.

Hayes, P.K., et al., "Gas Vesicles are Strengthened by the Outer-Surface Protein, GvpC", Archives of Microbiology, 157(3), pp. 229-234, (1992), 7 pages.

Hayes, P. et al., "The gvpA/C Cluster of *Anabaena flos-aquae* has Multiple Copies of a GeneEncoding GvpA", Archives of Microbiology, vol. 164(1), pp. 50-57, (1995), 9 pages.

He, X. et al., "Biophysical Mechanisms of Phase Contrast in Gradient Echo MRI", Proceedings of the National Academy of Sciences, 106(32), pp. 13558-13563, (2009), 6 pages.

Jaffer, F.A. et al., "Molecular and Cellular Imaging of Atherosclerosis", Emerging Applications. Journal of the American College of Cardiology, vol. 47, No. 7, pp. 1328-1338, (2006), 11 pages.

Jensen, J.H. et al., "NMR Relaxation in Tissues with Weak Magnetic Inhomogeneities", Magnetic Resonance in Medicine 44(1), pp. 144-156, (2000), 13 pages.

Jolesz, F.A., "MRI-Guided Focused Ultrasound Surgery", Annual Review of Medicine, 60(1), pp. 417-430, (2009), 17 pages.

Karlin, S. et al., "Applications and Statistics for Multiple High-Scoring Segments in Molecular Sequences", Proceedings of the Natl Academy of Sciences, vol. 90(12), pp. 5873-5877, (1993), 5 pages.

(56) References Cited

OTHER PUBLICATIONS

Karlin, S. et al., "Methods for Assessing the Statistical Significance of Molecular Sequence Features by Using General Scoring Schemes", Proceedings of the Natl Academy of Sciences, vol. 87(6), pp. 2264-2268, (1990), 5 pages.

Kaufmann, B.A., et al., "Molecular Imaging with Targeted Contrast Ultrasound", Current Opinion in Biotechnology, 18(1), pp. 11-16, (2007), 6 pages.

Kinsman, R. et al., "Genes Encoding Proteins Homologous to Halobacterial Gvps N, J, K, F & L are located downstream of gvpC in the Cyanobacterium *Anabaena flos-aguae*", DNA Sequence—The Journal of Sequencing and Mapping, vol. 7(2), pp. 97-106, (1997), 12 pages.

Kinsman, R., et al., "GvpCs With Reduced Numbers of Repeating Sequence Elements Bind to and Strengthen Cyanobacterial Gas Vesicles", Molecular Microbiology, 17(1), pp. 147-154, (1995), 10 pages.

Kislukhin A.A., et al., "Paramagnetic Fluorinated Nanoemulsions for Sensitive Cellular Fluorine-19 Magnetic Resonance Imaging", Nat. Mater, 15(6), pp. 662-668, (2016), 19 pages.

Lakshmanan et al., "Molecular Engineering of Acoustic Protein Nanostructures", ACS Nano Publications, vol. 10, No. 8, (Aug. 2016), 19 pages.

Lecoq, J. et al., "An Infrared Fluorescent Protein for Deeper Imaging", Nat Biotech, vol. 29, No. 8, pp. 715-716 (2011), 2 pages.

Lee, J.-H. et al., "Artificially Engineered Magnetic Nanoparticles for Ultra-Sensitive Molecular Imaging", Nat Med vol. 13, No. 1, pp. 95-99, (2007), 5 pages.

Li, Z. et al., "Comparison of Reporter Gene and Iron Particle Labeling for Tracking Fate of Human Embryonic Stem Cells and Differentiated Endothelial Cells in Living Subjects", Stem Cells 26 (4), pp. 864-873, (2008), 21 pages.

Li, N. et al., "Gas Vesicle Genes Identified in *Bacillus megaterium* and Functional Expression in *Escherichia coli*", Journal of Bacteriology, vol. 180, No. 9, pp. 2450-2458, (1998), 9 pages.

Mani, V. et al., "Gradient Echo Acquisition for Superparamagnetic Particles with Positive Contrast (GRASP): Sequence Characterization in Membrane and Glass Superparamagnetic Iron Oxide Phantoms at 1.5T and 3T", Magnetic Resonance in Medicine 55(1), pp. 126-135, (2006), 10 pages.

Maresca, D., et al., "Imaging Microvasculature with Contrast-Enhanced Ultraharmonic Ultrasound", Ultrasound in Medicine & Biology, vol. 40, No. 6, pp. 1318-1328, (2014), 13 pages.

Maresca, D., et al., "Nonlinear Ultrasound Imaging of Nanoscale Acoustic Biomolecules", Applied Physics Letters 110(7), pp. 073704-1-073704-5, (2017), 6 pages.

McMahon, M.T. et al., "New "Multicolor" Polypeptide Diamagnetic Chemical Exchange Saturation Transfer (DIACEST) Contrast Agents for MRI", Magnetic Resonance in Medicine 60(4), pp. 803-812, (2008), 10 pages.

Milo, R. et al., "BioNumbers—the Database of Key Numbers in Molecular and Cell Biology", Nucleic Acids Research 38, pp. D750-D753, (2010), 4 pages.

Myers, E.W. et al., "Optimal Alignments in Linear Space", Computer Applications in the Biosciences: CABIOS, vol. 4, No. 1, pp. 11-17, (1998), 8 pages.

Needleman, S.B. et al., "A General Method Applicable to the Search for Similarities in the Amino Acid Sequence of Two Proteins", Journal of Molecular Biology, 48(3), pp. 443-453, (1970), 12 pages.

Nilsson, B.L., et al., "Chemical Synthesis of Proteins", Annu. Rev. Biophys. Biomol. Struct.,34, pp. 91-118, (2005), 38 pages.

Pearson, W.R. et al., "Improved Tools for Biological Sequence Comparison", Proceedings of the Natl Academy Sciences, vol. 85, pp. 2444-2448, (1988), 5 pages.

Perez, J.M., et al., "Magnetic Relaxation Switches Capable of Sensing Molecular Interactions", Nat Biotech, vol. 20, No. 8, pp. 816-820, (2002), 5 pages.

Pfeifer, F., "Distribution, Formation, and Regulation of Gas Vesicles", Nat. Rev. Microbiol., vol. 10(10), pp. 705-715, (2012), 11 pages.

Rodriguez, P.L., et al., "Minimal "Self" Peptides that Inhibit Phagocytic Clearance and Enhance Delivery of Nanoparticles", Science, 339 (6122), pp. 971-975, (2013), 11 pages.

Ruoslahti, E., "RGD and Other Recognition Sequences for Integrins", Annual Rev. Cell Dev. Biol. 12(1), pp. 697-715, (1996), 21 pages.

Shaner, N.C., et al., "A Bright Monomeric Green Fluorescent Protein Derived from Branchiostoma Lanceolatum", Nat Meth, 10(5); pp. 407-409, (2013), 18 pages.

Schindelin, J. et al., "Fiji: An Open-Source Platform for Biological-Image Analysis", Nat Meth, vol. 9, No. 7, pp. 676-682, (2012), 7 pages.

Smith, T.F. et al., "Comparison of Biosequences", Advances in Applied Mathematics 2, pp. 482-489, (1981), 8 pages.

Shapiro et al., "Biogenic Gas Nanostructures as Ultrasonic Molecular Reporters", Nature Nanotechnology, vol. 9(4), pp. 311-316, (2014), 15 pages.

Shapiro, M.G. et al., "Directed Evolution of a Magnetic Resonance Imaging Contrast Agent for Noninvasive Imaging of Dopamine", Nat Biotech, 28(3), pp. 264-270, (2010), 15 pages.

Shapiro et al., "Genetically Encoded Reporters for Hyperpolarized Xenon Magnetic Resonance Imaging", Nat Chem, Advance Online Publication, DOI:10.1038/NCHEM.1934, vol. 6(7), pp. 629-634, (2014), 6 pages.

Shapiro, M.G., et al., "Protein Nanoparticles Engineered to Sense Kinase Activity in MRI", Journal of the American Chemical Society, 131(7), pp. 2484-2486, (2009), 8 pages.

Simon, R.D., "Morphology and Protein Composition of Gas Vesicles from Wild Type and Gas Vacuole Defective Strains of *Halobacterium salinarium* Strain 5", Journal of General Microbiology, 125, pp. 103-111, (1981), 9 pages.

Sremac, M., et al., "Recombinant Gas Vesicles from *Halobacterium* sp. Displaying SIV Peptides Demonstrate Biotechnology Potential as a Pathogen Peptide Delivery Vehicle", BMC Biotechnology, vol. 8(9), (2008), 14 pages.

Srivastava, A.K. et al., "Advances in Using MRI Probes and Sensors for In Vivo Cell Tracking as Applied to Regenerative Medicine", Disease Models and Mechanisms 8, pp. 323-336, (2015), 14 pages.

Stuber, M. et al., "Positive Contrast Visualization of Iron Oxide-Labeled Stem Cells Using Inversion-Recovery with ON-Resonant Water Suppression (IRON)", Magnetic Resonance in Medicine, 58(5), pp. 1072-1077, (2007), 6 pages.

Taratula et al., "Functionalized $^{129}$xe Contrast Agents for Magnetic Resonance Imaging", Current Opinion in Chemical Biology, 14(1), pp. 97-104, (2010), 14 pages.

Tashiro, Y. et al., "Molecular Genetic and Physical Analysis of Gas Vesicles in Buoyant Enterobacteria", Environmental Microbiology, 18(4), pp. 1264-1276, (2016), 13 pages.

Terreno, E. et al., "Challenges for Molecular Magnetic Resonance Imaging", Chemical Reviews, vol. 110, No. 5, pp. 3019-3042, (2010), 24 pages.

Walsby, A.E., "Ch. 10: Cyanobacteria: Planktonic Gas-Vacuolate Forms", The Prokaryotes, a Handbook on Habitats, Isolation, and Identification of Bacteria, 1, pp. 224-235, (2013), 13 pages.

Walsby, A.E., et al., "The Gas-Permeability Coefficient of the Cyanobacterial Gas Vesicle Wall", Journal of General Microbiology 138, pp. 837-845, (1992), 9 pages.

Walsby, A.E., "Ch. 28: Gas-Vacuolate Bacteria" (apart from cyanobacteria), in The Prokaryotes, Springer, pp. 441-447, (1981), 8 pages.

Walsby, A.E., et al., "Gas Vesicle Proteins", Biochem. J., vol. 264, pp. 313-322, (1989), 10 pages.

Walsby, A.E., "Gas Vesicles", Microbiological Reviews, vol. 58, No. 1, pp. 94-144, (1994), 51 pages.

Wang, Y. & Liu, T., "Quantitative Susceptibility Mapping (QSM): Decoding MRI Data for a Tissue Magnetic Biomarker", Magnetic Resonance in Medicine, vol. 73, pp. 82-101, (2015), 20 pages.

Woese, C.R. et al., "Bacterial Evolution", Microbiological Reviews, vol. 51, No. 2, pp. 221-271, (1987), 51 pages.

Yablonskiy, D.A., et al., "Theory of NMR Signal Behavior in Magnetically Inhomogeneous Tissues: The Static Dephasing Regime", Magnetic Resonance in Medicine 32, pp. 749-763, (1994), 15 pages.

(56) References Cited

OTHER PUBLICATIONS

Yi, G.et al., "Identifying Clusters of Functionally Related Genes in Genomes", Bioinformatics, vol. 23, No. 9, pp. 1053-1060, (2007), 8 Pages.

Zabow, G., et al., "Shape-Changing Magnetic Assemblies as High-Sensitivity NMR-Readable Nanoprobes", Nature, 520(7545), pp. 73-77, (2015), 24 pages.

Zakeri, B., et al., "Peptide Tag Forming a Rapid Covalent Bond to a Protein, Through Engineering a Bacterial Adhesin", PNAS, vol. 109, No. 12, pp. E690-E697, (2012), 8 pages.

Zordan, R.E., et al., "Avoiding the Ends: Internal Epitope Tagging of Proteins Using Transposon Tn7", Genetics, vol. 200(1), pp. 47-58, (2015), 42 pages.

Zurkiya, O. et al., "Off-Resonance Saturation as a Means of Generating Contrast with Superparamagnetic Nanoparticles", Magnetic Resonance in Medicine 56(4), pp. 726-732, (2006), 7 pages.

Caldwell et al. "A *Zoogloea* sp. associated with blooms of Anabaena flosaquae" Canadian Journal of Microbiology, NRC Research Press. Aug. 1978. vol. 24, No. 8. pp. 922-931. (Abstract Only) 2 pages.

Griffiths, et al., "The homologies of gas vesicle proteins", Journal of General Microbiology (1992), 138, 1243-1250.

Haacke, E.M. et al., "Susceptibility-Weighted Imaging: Technical Aspects and Clinical Applications," Part 1. American Journal of Neuroradiology 30 (1), pp. 19-30, (Jan. 2009), 29 pages.

Ngamdee et al. "Competition between Burkholderia pseudomallei and B. thailandesis" *BMC Microbiology, BioMed Central*. 2015. vol. 15, No. 56. 15 pages.

Non-Final Office Action for U.S. Appl. No. 15/663,635, filed Jul. 28, 2017, on behalf of California Institute of Technology, dated Jan. 2, 2019. 29 pages.

Pfeifer, Felicitas. "Distribution, formation and regulation of gas vesicles" *Nature Reviews—Microbiology, Macmillan Publishers Ltd.* Oct. 2012. vol. 10. pp. 705-715. 11 pages.

Qin et al. "Bacterial abundance and diversity in pond water supplied with different feeds" *Nature—Scientific Reports, Nature Publishing Group*. Oct. 19, 2016. vol. 6, No. 35232. pp. 1-13. 13 pages.

Restriction Requirement for U.S. Appl. No. 15/613,104 filed Jun. 2, 2017 on behalf of California Institute of Technology, dated Feb. 21, 2019. 9 pages.

Walsby, et al., "Average thickness of the gas vesicle wall in Anabaena flos-aquae". Journal of Molecular Biology, 1979. 129(2): p. 279-285.

Watanabe et al. "Distribution and identification of proteolytic *Bacillus* spp. in paddy field soil under rice cultivation" Canadian Journal of Microbiology, NRC Research Press. Jul. 1993. vol. 39. No. 7. pp. 674-680. (Abstract Only) 2 pages.

Altschul, et al, Gapped BLAST and PSI-BLAST: a new generation of protein database search programs. Nucleic Acids Res., 1997. 25(17): 3389-3402. p. 14.

Bar-Zion, A. et al. Acoustically Detonated Biomolecules for Genetically Encodable Inertial Cavitation. bioRxiv 620567 (2019) 11 pages.

Beard, P. "Biomedical photoacoustic imaging." *Interface Focus* 1, 602-631(2011).

Calvo, et al, Upstream open reading frames cause widespread reduction of protein expression and are polymorphic among humans. Proc Natl Acad Sci U S A, 2009. 106(18): p. 7507-7512.

Church C. "Frequency, pulse length, and the mechanical index." *Acoustics Research Letters Online*, 6(3), 162-168, 1-8 (2005).

Corrected Notice of Allowability for U.S. Appl. No. 15/613,104, filed Jun. 2, 2017 on behalf of California Institute of Technology dated Sep. 9, 2019 10 pages.

Coussios, C. et al., "Applications of Acoustics and Cavitation to Noninvasive Therapy and Drug Delivery." *Annu. Rev. Fluid Mech.* (2008) 40, 395-420. 28 pages.

Dang, L. H. et al., "Combination bacteriolytic therapy for the treatment of experimental tumors." *Proc. Natl. Acad. Sci. U. S. A.*98, 26, 15155-60 (2001).

Davila, M. L. et al. "Efficacy and Toxicity Management of 19-28z CAR T Cell Therapy in B Cell Acute Lymphoblastic Leukemia". 6(224), *Sci Transl Med* (2014). 23 pages.

Del Vecchio, D and Muarray, R.M. "Biomolecular Feedback Systems" bfs-pupss. Jun. 13, 2014. 280 pages.

Farhadi, A., et al., Recombinantly Expressed Gas Vesicles as Nanoscale Contrast Agents for Ultrasound and Hyperpolarized MRI. AlChE J, 2018. 64(8): p. 2927-2933.

Farhadi A. et al., "Ultrasound imaging of gene expression in mammalian cells" Science 365, 1469-1475, Sep. 2019, 43 pages.

Final Office Action for U.S. Appl. No. 15/663,635, filed Jul. 28, 2017 on behalf of California Institute of Technology dated Oct. 24, 2019 27 pages.

Forbes N. S., et al., "Sparse initial entrapment of systemically injected *Salmonella typhimurium* leads to heterogeneous accumulation within tumors." *Cancer Res*. 63, 5188-5193 (2003).

Häcker, G. et al., "Activation of the immune system by bacterial CpG-DNA." *Immunology*105, 245-251 (2002).

Holland C. et al., "An Improved Theory for the Prediction of Microcavitation Thresholds." vol. 36, No. 2, 204-208 *IEEE* (1989).

Huang, H. et al. "A G-Quadruplex-Containing RNA Activates Flourescence in a GFP-Like Flourophore", Nat Chem Biol., Aug. 2014, 10 (8); 686-691. 22 pages.

International Search Report for International Application No. PCT/US2020/012557 filed on Jan. 7, 2020 on behalf of California Institute of Technology dated May 1, 2020 5 pages.

International Search Report for International Application No. PCT/US2020/012572 filed on Jan. 7, 2020 on behalf of California Institute of Technology dated May 6, 2020 4 pages.

Jackson, H. J. et al., "Driving CAR T-cells forward." *Nat. Rev. Clin. Oncl*.13 (6), 370-383 (2016). 31 pages.

Jang, M. J. et al., "NeuroCa: integrated framework for systematic analysis of spatiotemporal neuronal activity patterns from large-scale optical recording data." *Neurophotonics*2(3), 035003 (2015). 16 pages.

Koehne G. et al., "Serial in vivo imaging of the targeted migration of human HSV-TK-transduced antigen-specific lymphocytes." *Nature Biotechnology* vol. 21, 405-413 (Apr. 2003).

Kunth, M. et al., "Protein Nanostructures Produce Self-Adjusting Hyperpolarized Magnetic Resonance Imaging Contrast through Physical Gas Partitioning." *ACS Nano* (2018). 12, 10939-10948. doi:10.1021/acsnano.8b04222.

Kwan, J. J. et al. "Ultrasound-Propelled Nanocups for Drug Delivery." *Small Journal* 11, No. 39, 5305-5314 (2015).

Lakshmanan, A., et al., Preparation of biogenic gas vesicle nanostructures for use as contrast agents for ultrasound and MRI. Nat Protoc, 2017. 12(10): p. 2050-2080.

Lu, G.J., et al., Acoustically modulated magnetic resonance imaging of gas-filled protein nanostructures. Nat Mater, 2018. 17(5): p. 456-463. 15 pages.

Maresca D, et al ., "Nonlinear X-Wave Ultrasound Imaging of Acoustic Biomolecules" *Phys Rev X* vol. 8, (2018). 041002-1 to 041002-12. 12 pages.

Maresca D, et al., "Biomolecular Ultrasound and Sonogenetics" *Annu Rev Chem Biomol Eng* vol. 9, 229-252 (Jun. 2018). 29 pages.

Milenic D. E. et al., "Antibody-Targeted Radiation Cancer Therapy." *Nature* 3, (2004). 488-498.

Natarajan, S, "NS3 protease from flavivirus as a target for designing antiviral inhibitors against dengue virus", Genetics and Molecular Biology, 33, 2, 214-219 (2010).

Notice of Allowance for U.S. Appl. No. 15/613,104, filed Jun. 2, 2017 on behalf of California Institute of Technology dated Jul. 18, 2019 15 pages.

Ntziachristos, V. "Going deeper than microscopy: the optical imaging frontier in biology." *Nature Methods* 7, No. 8, 603-614 (2010).

Piraner, D. I. et al. Going Deeper: Biomolecular Tools for Acoustic and Magnetic Imaging and Control of Cellular Function. Biochemistry 56, 5202-5209 (2017).

Purnick, P.E. and R. Weiss, "The second wave of synthetic biology: from modules to systems." *Nat Rev Mol Cell Biol*, 2009. 10(6): p. 410-422.

(56) References Cited

OTHER PUBLICATIONS

Ramnarine, et al, "Construction and geometric stability of physiological flow rate wall-less stenosis phantoms." *Ultrasound in medicine & biology* 27, No. 2, 245-250 (2001).
Ramsay, J.P., et al., "A quorum-sensing molecule acts as a morphogen controlling gas vesicle organelle biogenesis and adaptive flotation in an enterobacterium." *Proc Natl Acad Sci U S A*, 2011. 108(36): p. 14932-14937.
Rose, A.B., Intron-mediated regulation of gene expression. Curr Top Microbiol Immunol, 2008. 326: p. 277-290.
Ryan, R. M. et al. "Bacterial delivery of a novel cytolysin to hypoxic areas of solid tumors." *Gene Ther*.16, 329-339 (2009).
Santos E. B. et al., "Sensitive in vivo imaging of T cells using a membrane-bound Gaussia princeps luciferase", *Nat Med* vol. 15, No. 3, 338-344 (Mar. 2009).
Savage, D. C. "Microbial ecology of the gastrointestinal tract." *Annual review of microbiology* 31, 107-133 (1977).
Schechter, et al, On the active site of proteases. 3. Mapping the active site of papain; specific peptide inhibitors of papain. Biochem Biophys Res Commun., 1968 32(5): p. 898-902.
Schechter, et al, On the size of the active site in proteases. I. Papain. Biochem Biophys Res Commun., 1967. 27(2): p. 157-162.
Schneider, C. et al., "NIH Image to ImageJ: 25 years of image analysis." *Nat. Methods* 9(7), 671-675 (2012). 12 pages.
Simon, G. L. & Gorbach, S. L. Intestinal flora in health and disease. Gastroenterology 86, 174-193 (1984).
Smith TF, et al., Identification of common molecular subsequences. J Mol Biol, 1981. 147(1): 195-197. p. 3.
Szymczak A. L. et al., "Development of 2A peptide-based strategies in the design of multicistronic vectors." *Expert Opin Biol*Th 5 (5), 627-638 (2005).
Tsien R. Y., "Imagining imaging's future" *Nature Reviews Molecular Cell Biology*, Ss16-Ss21 (Sep. 2003).
Tsien, R. Y. The Green Fluorescent Protein. Annual Review of Biochemistry 67, 509-544 (1998).
Walsby, A. E."Gas Vesicles." *Annu. Rev. Plant Physiol*.26, 427-439 (1975).
Walsby, A. E. "The pressure relationships of gas vacuoles." *Proc. R. Soc. London. Ser. B. Biol. Sci*.178, 301-326 (1971).
Written Opinion for International Application No. PCT/US2020/012572 filed on Jan. 7, 2020 on behalf of California Institute of Technology dated May 6, 2020 6 pages.
Written Opinion for International Application No. PCT/US2020/012557 filed on Jan. 7, 2020 on behalf of California Institute of Technology dated May 1, 2020 6 pages.
Zhang, H. F. et al., "Imaging of hemoglobin oxygen saturation variations in single vessels in vivo using photoacoustic microscopy." *Appl. Phys. Lett*.90, 5-7, 053901 (2007).
Archer, E.J., et al., "Engineered *E. coli* That Detect and Respond to Gut Inflammation through Nitric Oxide Sensing." *ACS Synthetic Biology*, 1(10), 451-457, (2012). 7 pages.
Belkaid, Y., et al., "Role of the Microbiota in Immunity and Inflammation", Cell, 157(1): pp. 121-141, (2014), 21 pages.
Braat, H. et al., "A phase I Trial with Transgenic Bacteria Expressing Interleukin-10 in Crohn's Disease", Clinical Gastroenterology and Hepatology, 4 (6): pp. 754-759, (2006), 6 pages.
Bourdeau, R.W., et al., "Acoustic Reporter Genes for Non-Invasive Imaging of Microbial Populations in Mammalian Hosts." Nature 553, 86-90, (Jan. 2018). 19 pages.
Buchler, N.E., et al., "On Schemes of Combinatorial Transcription Logic", Proceedings of the National Academy of Sciences, 100 (9): pp. 5136-5141, (2003), 6 pages.
Chu, J., et al., "A Bright Cyan-Excitable Orange Fluorescent Protein Facilitates Dual-Emission Microscopy and Enhances Bioluminescence Imaging In Vivo." Nat Biotech, 34 (7): pp. 760-767, (2016), 29 pages.
Claesen, J., et al., "Synthetic Microbes as Drug Delivery Systems" ACS Synthetic Biology, 4 (4): pp. 358-364, (2014), 7 pages.

Courbet, A., et al., "Detection of Pathological Biomarkers in Human Clinical Samples via Amplifying Genetic Switches and Logic Gates", Science Translational Medicine, 7(289): pp. 289ra83-289ra83, (2015), 49 pages.
Daniel, C., et al., "Bioluminescence Imaging Study of Spatial and Temporal Persistence of Lactobacillus Plantarum and Lactococcus Lactis in Living Mice" Applied and Environmental Microbiology, 79 (4): pp. 1086-1094, (2013), 9 pages.
Daniel, C., et al., "Recombinant Lactic Acid Bacteria as Mucosal Biotherapeutic Agents", Trends in Biotechnology, 29 (10): pp. 499-508, (2011), 10 pages.
Danino, T., et al., "In Vivo Gene Expression Dynamics of Tumor-Targeted Bacteria", ACS Synthetic Biology, 1 (10): pp. 465-470, (2012), 6 pages.
Danino, T., et al., "Programmable Probiotics for Detection of Cancer in Urine", Science Translational Medicine, 7 (289): pp. 289ra84-289ra84, (2015), 28 pages.
Dassarma, P., et al., "Bioengineering Novel Floating Nanoparticles for Protein and Drug Delivery." *Materials Today: Proceedings: Advances in Functional Materials (Conference 2015)*, 3(2), 206-210, (2016). 8 pages.
Derrien, M. et al "Fate, Activity, and Impact of Ingested Bacteria within the Human Gut Microbiota." *Trends in Microbiology*, 23(6), 354-366, (2015). 13 pages.
Din, M.O., et al., "Synchronized Cycles of Bacterial Lysis for In Vivo Delivery", Nature, 536 (7614): pp. 81-85, (2016), 18 pages.
Evbuomwan, O.M., et al. "Chapter 10: CEST and PARACEST Agents for Molecular Imaging," in *The Chemistry of Molecular Imaging*. Ed. Nicholas Long and Wing-Tak Wong, 225-243, Wiley & Sons, 2015. 27 pages.
Fischbach, M.A., et al., "Cell-Based Therapeutics: The Next Pillar of Medicine", Science Translational Medicine, 5 (179), pp. 179ps7-179ps7, (2013), 7 pages.
Foster, F.S., et al., "Advances in Ultrasound Biomicroscopy", Ultrasound in Medicine & Biology, 26 (1), pp. 1-27, (2000), 27 pages.
Foster, F.S., et al., "Principles and Applications of Ultrasound Backscatter Microscopy." *IEEE Transactions on Ultrasonics, Ferroelectrics and Frequency Control*, 40(5), 608-617, (1993). 10 pages.
Foucault, M.-L., et al., "In Vivo Bioluminescence Imaging for the Study of Intestinal Colonization by *Escherichia coli* in Mice", Applied and Environmental Microbiology, 76 (1): pp. 264-274, (2010), 11 pages.
Gorbach, S.L., "Chapter 95: Microbiology of the Gastrointestinal Tract", *Medical Microbiology, 4th Edition*, Editor: Samuel Baron, University of Texas Medical Branch at Galveston, Galveston, TX (1996). 10 pages.
Hung, A.H., et al., "Magnetic Barcode Imaging for Contrast Agents." *Magnetic Resonance in Medicine*, 77(3), 970-978, (2017). 9 pages.
Klumpp, S., et al., "Bacterial Growth: Global Effects on Gene Expression, Growth Feedback and Proteome Partition", Current Opinion in Biotechnology, 28, pp. 96-102, (2014), 7 pages.
Kotula, J.W., et al., "Programmable Bacteria Detect and Record an Environmental Signal in the Mammalian Gut", Proceedings of the National Academy of Sciences, 111 (13): pp. 4838-4843, (2014), 6 pages.
Matsumoto, Y., et al., "T2 Relaxation Inducesd by Clusters of Supermagnetic Nanoparticles: Monte Carlo Simulations." *Magnetic Resonance Imaging* 26, 994-998, (2008). 6 pages.
Meeker, D. Finite Element Method Magnetics. *FEMM*, 4, 32 (2010). 162 pages.
Mowat, A.M., et al., "Regional Specialization within the Intestinal Immune System." *Nature Reviews Immunology*, 14(10), 667-685, (2014). 19 pages.
Ntziachristos, V., et al., "Looking and Listening to Light: the Evolution of Whole-Body Photonic Imaging." *Nature Biotechnology*, 23(3), 313-320, (2005). 8 pages.
Puderbach, M. et al. "MR Imaging of the Chest: A Practical Approach at 1.5 T." *European Journal of Radiology* 64, 345-355, (2007). 13 pages.

(56) References Cited

OTHER PUBLICATIONS

Reits, E.A., et al., "From Fixed to FRAP: Measuring Protein Mobility and Activity in Living Cells", Nature Cell Biology, 3 (6), pp. E145-E147, (2001), 3 pages.
Romero, P.A., et al., "Exploring Protein Fitness Landscapes by Directed Evolution", Nature Reviews Molecular Cell Biology, 10 (12): pp. 866-876, (2009), 25 pages.
Round, J.L., et al., "The Gut Microbiota Shapes Intestinal Immune Responses During Health and Disease." *Nature Reviews Immunology*, 9(5), 313-323, (2009). 12 pages.
Schweser, F., et al., "Quantitative Imaging of Intrinsic Magnetic Tissue Properties Using MRI Signal Phase: An Approach to in vivo Brain Iron Metabolism?" *NeuroImage*, 54(4), 2789-2807, (2011). 19 pages.
Shaner, N.C., et al., "Improved Monomeric Red, Orange and Yellow Fluorescent Proteins Derived from *Discosoma* sp. Red Fluorescent Protein", Nature Biotechnology, 22 (12): pp. 1567-1572, (2004), 7 pages.
Shaner, N.C., et al., "Improving the Photostability of Bright Monomeric Orange and Red Fluorescent Proteins", Nature Methods, 5 (6): pp. 545-551, (2008), 25 pages.
Silva-Rocha, et al., "Mining Logic Gates in Prokaryotic Transcriptional Regulation Networks", FEBS Letters, 582 (8): pp. 1237-1244, (2008), 8 pages.
Smith-Bindman, R., et al., "Use of Diagnostic Imaging Studies and Associated Radiation Exposure for Patients Enrolled in Large Integrated Health Care Systems, 1996-2010" JAMA, 307 (22): pp. 2400-2409, (2012), 10 pages.
Sprinzak. D., et al., "Reconstruction of Genetic Circuits", Nature, 438 (7067), pp. 443-448, (2005), 6 pages.
Steidler, L., et al., "Treatment of Murine Colitis by Lactococcus Lactis Secreting Interleukin-10", Science, 289 (5483): pp. 1352-1355, (2000), 4 pages.
Tang, J., et al., "Chapter 25: SWIM: Susceptibility Mapping as a Means to Visualize Veins and Quantify Oxygen Saturation." in *Susceptibility Weighted Imaging in MRI*. John Wiley & Sons, Inc., 461-485, (2011). 26 pages.
Van Keulen, G et al. "Gas Vesicles in Actinomycetes: Old Buoys in Novel Habitats?", Trends in Microbiology, 13 (8): pp. 350-354, (2005), 6 pages.
Walsby, A.E., et al., "Gas Vesicles." *Microbiological Reviews*, vol. 58, No. 1, pp. 94-144, (1994). 51 pages.
Wang, Y., et al., "The Role of Microbiome in Central Nervous System Disorders", Brain, Behavior, and Immunity, 38, pp. 1-12, (2014), 28 pages.
Weissleder, R., et al., "Ultrasmall Superparamagnetic Iron Oxide: Characterization of a New Class of Contrast Agents for MR Imaging." Radiology, 175(2), 489-493, (1990). 7 pages.
Wells, J.M., et al., "Mucosal Delivery of Therapeutic and Prophylactic Molecules Using Lactic Acid Bacteria", Nature Reviews Microbiology, 6 (5), pp. 349-362, (2008), 14 pages.
Yurist-Doutsch, S., et al., "Gastrointestinal Microbiota-Mediated Control of Enteric Pathogens", Annual Review of Genetics, 48, pp. 361-382, (2014), 25 pages.
Zhang, S., et al., "PARACEST Agents: Modulating MRI Contrast via Water Proton Exchange." *Accounts of Chemical Research*, 36(10), 783-790, (2003). 8 pages.
International Search Report and Written Opinion for PCT App. No. PCT/US2020/025608 filed on Mar. 29, 2020 on behalf of California Institute of Technology, dated Jul. 17, 2020. 13 Pages.
Non-Final Office Action for U.S. Appl. No. 15/663,635, filed Jul. 28, 2017 on behalf of California Institute of Technology dated May 29, 2020 24 pages.
Blum-Oehler, G., et al., "Development of strain-specific PCR reactions for the detection of the probiotic *Escherichia coli* strain Nissle 1917 in fecal samples." Research in Microbiology, 2002. 154(1): p. 59-66.
Parks, T.D., et al., "Release of proteins and peptides from fusion proteins using a recombinant plant virus proteinase." Analytical Biochemistry, 1994. 216(2): p. 413-417.

Sauer, R.T. and Baker, T.A., "AAA+ Proteases: ATP-Fueled Machines of Protein Destruction." Annual Review of Biochemistry, 2011. 80: p. 587-612.
St-Pierre, F., et al., "One-step cloning and chromosomal integration of DNA." ACS synthetic biology, 2013. 2(9): p. 537-541.
Suzuki, S., et al., "Development of an artificial calcium-dependent transcription factor to detect sustained intracellular calcium elevation." ACS Synthetic Biology, 2014. 3(10): p. 717-722.
Aguilera et al., "Systemic in vivo distribution of activatable cell penetrating peptides is superior to cell penetrating peptides." Integr Biol (Camb). 2009. 1(5-6): p. 371-381. 22 pages.
Baker, T.A. et al., "ClpXP, an ATP-powered unfolding and protein-degradation machine." Biochimica et Biophysica Acta (BBA)-Molecular Cell Research, 2012. 1823(1): p. 15-28. 33 pages.
Blum-Oehler, G., et al., "Development of strain-specific PCR reactions for the detection of the probiotic *Escherichia coli* strain Nissle 1917 in fecal samples." Research in Microbiology, 2003. 154(1): p. 59-66. Abstract Only.
Cameron, D.E. and Collins, J.J., "Tunable protein degradation in bacteria." Nature Biotechnology 2014. 32 (12): p. 1276-1281. 19 pages.
Cha-Molstad et al., "Modulation of SQSTM1/p62 activity by N-terminal arginylation of the endoplasmic reticulum chaperone HSPA5/GRP78/BiP." Autophagy, 2016. 12(2): p. 426-428.
Chassin H. et al., "A modular degron library for synthetic circuits in mammalian cells." Nature Communications 2019.10: 2013. 11 pages.
Datsenko, K.A. et al., "One-step inactivation of chromosomal genes in *Escherichia coli* K12 using PCR products." Proceedings of the National Academy of Sciences, 2000. 97(12): p. 6640-6645.
Drag, M. et al., "Emerging principles in protease-based drug discovery." Nature Reviews Drug Discovery 9 (9), 690-701, (2010). 27 pages.
Elowitz, M.B. and S. Leibler, A synthetic oscillatory network of transcriptional regulators. Nature, 2000. 403 (6767): p. 335-338.
Fernandez-Rodriguez, J. et al., "Post-translational control of genetic circuits using Potyvirus proteases." Nucleic Acids Research 44, No. 13, 6493-6502 (2016).
Gao, X.J. et al., "Programmable protein circuits in living cells." Science 361, 1252-1258 (2018).
Gardner, T.S. et al., "Construction of a genetic toggle switch in *Escherichia coli*." Nature, 2000. 403 (6767): p. 339-342.
Geva-Zatorsky, N., et al., "In vivo imaging and tracking of host-microbiota interactions via metabolic labeling of gut anaerobic bacteria." Nature Medicine, 2015. 21(9): p. 1091-1100. 27 pages.
Goll, D.E., et al., "The calpain system." Physiological Reviews, 2003. 83(3): p. 731-801.
Heim, R. et al., "Engineering green fluorescent protein for improved brightness, longer wavelengths and fluorescence resonance energy transfer." Current Biology 6, 178-182 (1996).
Khalil, A.S. et al., "Synthetic biology: applications come of age." Nature Reviews Genetics, 2010. 11(5): p. 367-379.
Lin, M.Z. et al., "Genetically encoded indicators of neuronal activity." Nature Neuroscience 19, No. 9, 1142-1153 (2016).
Lopez-Otin, C. et al., "Proteases: multifunctional enzymes in life and disease." Journal of Biological Chemistry 283, No. 45, 30433-7 (2008).
Machtaler, S., et al., "Assessment of inflammation in an acute on chronic model of inflammatory bowel disease with ultrasound molecular imaging." Theranostics, 2015. 5(11): p. 1175-1186.
Mark Welch, J.L., et al., "Spatial organization of a model 15-member human gut microbiota established in gnotobiotic mice." Proceedings of the National Academy of Sciences, 2017. 114(43): p. E9105-E9114.
Mitra, R.D. et al., "Fluorescence resonance energy transfer between blue emitting and red-shifted excitation derivatives of the green fluorescent protein." Gene 173, 13-17 (1996).
Miyawaki, A. et al., "Molecular spies for bioimaging-fluorescent protein-based probes." Molecular Cell 58, 632-643 (2015).
Muradali, D. et al., "US of gastrointestinal tract disease." Radiographics, 2015. 35(1): p. 50-68.
Ong, I.L.H. et al., "Recent developments in protease activity assays and sensors." Analyst 142, 1867-1881 (2017).

(56) References Cited

OTHER PUBLICATIONS

Ono, Y. et al., "Calpain research for drug discovery: challenges and potential." Nature Reviews Drug Discovery, 2016. 15(12): p. 854-876. 34 pages.

Ono, Y. et al., "Calpains—an elaborate proteolytic system." Biochimica et Biophysica Acta (BBA)-Proteins and Proteomics, 2012. 1824(1): p. 224-236.

Palmer, A.E. et al., "Design and application of genetically encoded biosensors." Trends in Biotechnology 29 (3), 144-152 (2011). 18 pages.

Parks, T.D., et al., "Release of proteins and peptides from fusion proteins using a recombinant plant virus proteinase." Analytical Biochemistry, 1994. 216(2): p. 413-417. Abstract Only.

Phan, J., et al., "Structural basis for the substrate specificity of tobacco etch virus protease." Journal of Biological Chemistry, 2002. 277(52): p. 50564-50572.

Rodriguez, E.A. et al. "The growing and glowing toolbox of fluorescent and photoactive proteins." Trends in Biochemical Sciences 42 (2), 111-129 (2017). 31 pages.

Sauer, R.T. and Baker, T.A., "AAA+ Proteases: ATP-Fueled Machines of Protein Destruction." Annual Review of Biochemistry, 2011. 80: p. 587-612. Abstract Only.

Sauer, R.T., et al., "Sculpting the proteome with AAA(+) proteases and disassembly machines." Cell, 2004. 119(1): p. 9-18. 21 pages.

Sonnenborn, U. et al., "The non-pathogenic *Escherichia coli* strain Nissle 1917—features of a versatile probiotic." Microbial Ecology in Health and Disease, 2009. 21(3-4):p. 122-158.

Stein, V. et al. "Protease-based synthetic sensing and signal amplification." Proceedings of the National Academy of Sciences 111, No. 45, 15934-15939 (2014).

St-Pierre, F., et al., "One-step cloning and chromosomal integration of DNA." ACS synthetic biology, 2013. 2(9): p. 537-541. Abstract Only.

Suzuki, S., et al., "Development of an artificial calcium-dependent transcription factor to detect sustained intracellular calcium elevation." ACS Synthetic Biology, 2014. 3(10): p. 717-722. Abstract Only.

Tigges, M., et al., "A tunable synthetic mammalian oscillator. Nature," 2009. 457(7227): p. 309-312.

Turk, B., et al., "Protease signaling: the cutting edge." The EMBO Journal 31, 1630-1643 (2012).

Yin, L. et al., "Quantitatively Visualizing Tumor-Related Protease Activity in Vivo Using a Ratiometric Photoacoustic Probe." J. Am. Chem. Soc., 2019. 141(7): p. 3265-3273.

\* cited by examiner

GAS-FILLED STRUCTURES AND RELATED COMPOSITIONS, METHODS AND SYSTEMS FOR MAGNETIC RESONANCE IMAGING

CROSS REFERENCE TO RELATED APPLICATIONS

The present application claims priority to U.S. Provisional Application No. 62/367,750, entitled "Acoustomagnetic imaging with gas-filled protein nanostructures" filed on Jul. 28, 2016, which is incorporated herein by reference in its entirety. The present application is also related to co-pending U.S. application Ser. No. 15/613,104, entitled "Gas-filled Structures and related Compositions, methods and systems to image a target site" filed on Jun. 2, 2017, which is also incorporated herein by reference in its entirety.

STATEMENT OF INTEREST

This invention was made with government support under Grant No. EB018975 awarded by the National Institutes of Health. The government has certain rights in the invention.

FIELD

The present disclosure relates to gas-filled structures for use in imaging technologies, and related compositions, methods and systems to image a target site with particular reference to imaging performed by magnetic resonance imaging.

BACKGROUND

Contrast enhanced imaging of cellular and molecular processes inside living animals and patients can be performed with contrast agents compatible with imaging modalities such as magnetic resonance imaging (MRI) and ultrasound, which are among the most widely used biomedical imaging modalities due to their superior spatiotemporal resolution, safety, cost and ease of use.

Challenges remain for identifying and developing methods and biocompatible nanoscale contrast agents that are non-toxic, genetically modifiable, capable of enabling detection at nanomolar concentrations and producing dynamic contrast in response to local molecular signals.

SUMMARY

Provided herein are gas vesicles protein structures (GVPS) with associated acoustic and magnetic properties and related compositions, methods, and systems which can be used in several embodiments to perform singleplex or multiplex magnetic resonance imaging (MRI) alone or in combination with ultrasound, as well as cell-specific molecular targeting.

According to a first aspect, a method to provide a magnetic resonance imaging of a target site comprising a bulk material and GVPS is described. In the method, the gas vesicle protein structure (GVPS) contains a gas having a gas susceptibility. In the method, the bulk material of the target site has a bulk material susceptibility and the gas susceptibility is substantially distinct from the bulk material susceptibility. The method comprises imaging a target site comprising GVPS to obtain an MRI image by detecting volume susceptibilities ($\chi$) of the target site or relaxation rates (R2 or R2*) of nuclear spins of atoms in the bulk material. In some embodiments, the MRI image is QSM, T2, T2*, T2- or T2*-weighted map.

According to a second aspect, a method is described to provide a background-free magnetic resonance imaging of a target site containing a bulk material contrasted with a contrast agent comprising a gas vesicle protein structure (GVPS) type. In the method, the GVPS type contains a gas having susceptibility substantially distinct from the susceptibility of the bulk material in the target site. The GVPS type also has a selectable acoustic collapse pressure value derived from an acoustic collapse pressure profile of the GVPS type. The method comprises administering to a target site a contrast agent comprising a gas vesicle protein structure (GVPS) type herein described, imaging the target site by obtaining a first MRI image of the target site, collapsing the GVPS type by applying collapsing ultrasound to the target site, the collapsing ultrasound applied at a collapsing ultrasound pressure greater than a selectable acoustic collapse pressure value, and after collapsing, imaging the target site by applying an external magnetic field to the target site to obtain a second MRI image of the target site.

According to a third aspect, an acoustically modulated multiplexed imaging method and system to be used on a target site contrasted with at least a first and second gas vesicle protein structure (GVPS) types are described. In the method, the first GVPS type exhibits a first acoustic collapse pressure profile and a first selectable acoustic collapse pressure value and the second GVPS type exhibits a second acoustic collapse pressure profile and a second selectable acoustic collapse pressure value. The method comprises imaging the target site by applying an external magnetic field to the target site to obtain a first MRI image of the target site, selectively collapsing the first GVPS type by applying collapsing ultrasound to the target site, the collapsing ultrasound applied at a first acoustic collapse pressure value equal to or higher than the first selectable acoustic collapse pressure value and lower than the second selectable acoustic collapse pressure value. The method further comprises imaging the target site containing at least the second, uncollapsed GVPS type by applying an external magnetic field to the target site to obtain a second MRI image of the target site. MRI imaging parameters used before and after each collapsing are identical.

According to a fourth aspect, an MRI multiplexing method and system are described to be used on a target site contrasted with at least a first and a second gas vesicle protein structure (GVPS) type. In the method, a parameter fingerprint type is established, the established parameter fingerprint type consisting of a set of at least two parameters taken from QSM susceptibility ($\chi$), T2 relaxivity (r2), T2* relaxivity (r2*) and T1 relaxivity (r1) (e.g. $\chi$ and r2). For the established parameter fingerprint type, a first set of parameter fingerprint values is known for the first GVPS type (e.g. $\chi(\alpha)$ and r2($\alpha$)) and a second set of parameter fingerprint values is known for the second GVPS type (e.g. $\chi(\beta)$ and r2($\beta$)). The ratio of all the first set of parameter fingerprint values (e.g. $\chi(\alpha)$:r2($\alpha$)) is different than the corresponding ratio of all the second set of parameter fingerprint values (e.g. $\chi(\beta)$:r2($\beta$)). The at least two parameters of the established parameter fingerprint type are measured (e.g. $X_{obs}$ in QSM and $R2_{obs}$ in T2) by MRI at the target site containing the at least first and second GVPS type. The measured first and second parameters can be unmixed with the first and second sets of parameter fingerprint values to produce a voxel-wise mapping of concentration values of the at least first and second GVPS type in the target site.

According to a fifth aspect, a method is described to perform MRI and ultrasound imaging of a target site comprising water and contrasted with a gas vesicle protein structure (GVPS) type. In the method, the GVPS type has an associated susceptibility and relaxivity property distinct from water and a selectable acoustic collapse pressure value derived from an acoustic collapse pressure profile of the GVPS type. The method comprises administering to a target site a contrast agent comprising a gas vesicle protein structure (GVPS) herein described, imaging the target site by applying an external magnetic field to the target site to obtain a MRI image of the target site, imaging the target site by applying imaging ultrasound to the target site to obtain an ultrasound image of the target site, and the imaging ultrasound applied an imaging ultrasound pressure lower than a selectable acoustic collapse pressure value. An enhanced image can be created from the MRI image and the ultrasound image.

According to a sixth aspect, a method to perform MRI imaging of a biochemical event in a target site contrasted with a gas vesicle protein structure (GVPS) type is described. In the method, the GVPS type presents a functional group able to attach directly or indirectly to a corresponding functional group on the same or other GVPS type upon occurrence of the biochemical event. The method comprises imaging the target site by obtain a series of MRI images of the target site and detecting an increase or decrease in MRI contrast. In some embodiments, the increase or decrease in MRI contrast is an increase or decrease in $R_2$ or $R_2^*$ relaxation rate at the same measured susceptibility value. The increase in R2* and R2 can be 5-fold, 10-fold or 15-fold or greater compared to control samples with no clustering of GVPSs.

According to a seventh aspect, a method and system are described to image a biochemical event within a prokaryotic host and/or to label the prokaryotic host comprised in an imaging target site, the method comprising:

introducing into the prokaryotic host a gas vesicle gene cluster (GVGC) configured for expression in the prokaryotic host, the gas vesicle gene cluster (GVGC) encoding a gas vesicle (GV) type, wherein the GV type is a reportable molecular component of a gas vesicle reporting (GVR) genetic circuit, in which molecular components are connected one to another in accordance to a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to the biochemical event and/or a trigger molecular component within the target prokaryotic host; and imaging the target site comprising the prokaryotic host by any of the method to perform MRI and/or ultrasound imaging of the target site herein described.

The system comprises the GVGC, related GVR genetic circuits, related components and/or prokaryotic host cells in a combination for simultaneous combined or sequential use in the imaging methods herein described.

According to an eight aspect, a method and system is described to provide an MRI and/or ultrasound multiplexed imaging of two or more biochemical events and/or labeled prokaryotic cell types comprised in an imaging target site, the method comprising:

in some embodiments, the existence of two or more prokaryotic cell types at the imaging target site, and each prokaryotic cell types express a single but different GV type.

in some other embodiments, introducing into the one or more prokaryotic cell types a plurality of gas vesicle reporter genes (GVGCs) encoding a plurality of gas vesicle (GV) types, the plurality of GVGCs introduced to provide a plurality of reportable genetic molecular components of one or more GVR genetic circuits, in which molecular components are connected one to another in accordance to a circuit design by activating, inhibiting, binding or converting reactions to form a fully connected network of interacting components, wherein in each reportable genetic molecular component the gas vesicle (GV) type is expressed from the plurality of GVGCs when the one or more GVR genetic circuits operate according to the circuit design in response to a same or different biochemical events and/or to a same or different triggering molecular component, wherein each GV type exhibits i) an acoustic collapse pressure profile defined as a collapse function from which a collapse amount can be determined, and ii) a selectable acoustic collapse pressure value, selectable acoustic collapse pressure values going from a lowest acoustic collapse pressure value to a highest acoustic collapse pressure value, and iii) a distinguishable MRI fingerprint from two or more of the four parameters: $\chi$, r2, r2* and r1 imaging the target site of the one or more prokaryotic cell type by the method to perform multiplexed MRI imaging and/or ultrasound imaging herein described.

In some embodiments, the method can further comprise:

selectively collapsing each GV type to a collapse amount higher than a collapse amount of each remaining GV type by applying collapsing ultrasound to the target site comprising the one or more prokaryotic cell types, the collapsing ultrasound applied at a pressure value equal to or higher than the selectable acoustic collapse pressure value of the GV type being collapsed and lower than an acoustic collapse pressure value of said each remaining GV type or types.

The method further comprises imaging the target site containing the remaining GV type or types by applying imaging ultrasound to the target site, the imaging ultrasound applied at a pressure value lower than a lowest acoustic collapse pressure value of said each remaining GV type or types and/or with MRI imaging method herein described. In those embodiments, the method can also comprises repeating the collapsing and the imaging until all GV types are collapsed, thus providing a sequence of visible images of the target site, the sequence being indicative of image-by-image decreasing remaining GV types.

The gas vesicle protein structures and related variants, compositions methods and systems herein described can be used in several embodiments to provide magnetic resonance imaging with enhanced contrast and molecular sensitivity at sub-nanomolar concentration with particular reference to imaging of internal body structures of an individual such as tendons, muscles, joints, vessels and internal organs.

The gas vesicle protein structures and related variants, compositions methods and systems herein described can be used in several embodiments to allow multiplexed imaging using parametric MRI, and differential acoustic sensitivity and background-free MRI when combined with ultrasound.

The gas vesicle protein structures and related variants, compositions methods and systems herein described can be used in several embodiments to detect clustering-induced changes in MRI contrast also enable the design of dynamic molecular sensors.

The gas vesicle protein structures and related variants, compositions methods and systems herein described can be used in several embodiments to track moving target sites such as cells or other structures within the body of an individual or other environments.

The gas vesicle protein structures and related variants, compositions methods and systems herein described can be used in several embodiments to provide MRI imaging with high sensitivity, biodistribution, multiplexing, multimodal detection and/or molecular targeting to help MRI fulfill its potential as a high-performance modality for molecular imaging.

The gas vesicle protein structures and related variants, compositions methods and systems herein described can be used in several embodiments to produce non-toxic, robust MRI contrast via differential magnetic susceptibility at nanomolar concentrations.

The gas vesicle protein structures and related variants, compositions methods and systems herein described can be used in several embodiments to produce dynamic contrast in response to local molecular signals.

The gas vesicle protein structures and related variants, compositions methods and systems herein described allow GVPS to be used as multi-modal contrast agent compatible with different types of imaging modalities, including susceptibility-based MRI, Xenon Hyper-CEST and ultrasound imaging.

The gas vesicle protein structures and related variants, compositions, methods, and systems herein described can be used in connection with various applications wherein magnetic resonance imaging of a target site is desired. For example, The gas vesicle protein structures and related variants, compositions methods and systems herein described can be used to spatially and/or temporally control the contrast of the imaging of a biological target site and in particular internal body structure or molecular composition or cellular composition and activity of tissues of an individual in medical applications, as well diagnostics applications. These methods can also be used to image GVs expressed genetically inside cells, thereby acting as labels of cell location or reporter of gene expression. These methods can also be used to induce the clustering of GVs upon a specific biochemical event, and thereby the change of MRI contrast upon clustering can provide a way to report the specific biochemical event. Additional exemplary applications include uses of gas vesicle protein structures and related variants, compositions methods and systems herein described in several fields including basic biology research, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 shows a rendition of GVs illustrating GvpA as the main building block of GVs. GvpA is a structural protein that assembles through repeated unites to make up the bulk of GVs. GvpC is a scaffold protein with 5 repeat units that assemble on the outer shell of GVs. GvpC can be engineered to tune the mechanical and acoustic properties of GVs as well as act as a handle for appending moieties on to.

FIG. 3A shows T2*-weighted and FIG. 3B shows T2-weighted images at echo time TE=45 msec. FIG. 3C and FIG. 3D show T2* and T2 map, respectively, where image intensities are in the unit of msec. T2* relaxation is significantly faster at the rim than at the center of the well, while T2 relaxation does not show the same pattern. In all the images, $B_0$ fields are along the vertical direction. The well contained 1.42 nM Halo GVs.

FIG. 5A shows TEM images and simulated magnetic field profiles generated by intact (left) and collapsed (right) Mega GVs. FIG. 5B shows Magnetic susceptibility maps of wells containing phosphate-buffered saline (PBS) or 4.9 nM Mega GVs before and after the application of ultrasound, and the resulting difference image. FIG. 5C shows T2*-weighted images of a phantom containing wells with 8.1 and 4.9 nM Mega GVs alongside hyperintense contrast from wells with low-percentage agarose and hypointense contrast from 40 μm (inner diameter) capillary tubes containing 500 mM $NiSO_4$, before and after the application of ultrasound, and the resulting difference image.

FIG. 7A shows T2*-weighted image of a coronal slice of the mouse brain including the site of GV injection at the striatum. FIG. 7B shows QSM image of the same slice.

FIG. 8A shows schematic of the pressure-scanning paradigm, wherein sequential ultrasound pulses are applied between MRI images. The low-pressure ultrasound (Low US) selectively collapses $Ana_{AC}$ GVs and eliminates their MRI contrast; subsequently, high-pressure ultrasound (High US) collapses $Ana_{WT}$ GVs. FIG. 8B shows hydrostatic collapse measurement of $Ana_{AC}$ and $Ana_{WT}$ monitored by pressure-sensitive optical density at 500 nm ($OD_{500,PS}$). FIG. 8C shows, in the left, representative QSM images taken before ultrasound application (Pre), after the low-pressure ultrasound (Low) and after high-pressure ultrasound (High) of wells containing $Ana_{WT}$, $Ana_{AC}$ or a 1:1 mixture of the two, as indicated. In the Right: difference images obtained by pairwise subtraction, color mapped to distinguish variants collapsing at different pressures. The total GV concentrations were 0.91 nM in all three samples and the images were displayed from −10 to +50 ppb. FIG. 8D shows average susceptibility of each sample type relative to PBS buffer at each stage of the pressure-scanning paradigm. N=4. Error bars represent SEM. Complete collapse of GV specimens resulted in slightly negative susceptibility relative to the PBS solution, as expected since proteins are more diamagnetic than water [1]. FIG. 8E shows anatomical image with outlines for the subcutaneously injected areas of $Ana_{AC}$ GVs (13.7 nM clustered form) and E. coli expressing A2C GVs ($OD_{600}$ 150). FIG. 8F shows maps of changes in signal intensity in insonated regions following the sequential application of Low US and High US to mice. The insonated regions are outlined in white. FIG. 8G shows statistics on the differential change of the change in signal intensity after the application of Low US relative to High US. GVs collapsed at Low US are expected to have positive values, whereas GVs collapsed only at High US are expected to have negative values. Average signal change at 8 injection sites (4 of each type from a total of 4 mice are shown and the error bars represent SEM.

FIG. 9A shows TEM images (top row) and magnetic susceptibility and r2 relaxivity values for Bacillus megaterium (Mega), Anabaena flos-aquae (Ana) and Halobacterium salinarum (Halo) GVs. The molar susceptibility ($\Delta\chi$) values are referenced to blank PBS buffer. Error bars represent the standard error of the slope from linear regression fitting (FIG. 4). As it shows, different GV types can have different GV geometries (short and thin for Mega, long and thin for Ana, short and rounded for Halo, etc.). These different geometries produce different susceptibility contrast ($\Delta\chi$) and T2 contrast (r2) values. Note that susceptibility would be based mainly on the GV size, while T2 would be based on both size and shape. These differences can be used to fingerprint the GV type, or at least GV types having similar geometries. FIG. 9B shows representative QSM map (first row), T2 map (second row) and calculated GV concentrations (the 3rd and 4th rows) of three samples that contain Halo GVs, Mega GVs or a 1:1 mixture of both GV types. The concentration of Mega (magenta) and Halo (cyan) GVs were pixel-wise calculated and displayed in overlay. The overlaid image demonstrates that two types of cells carrying different types of GVs can be distinguished even if they are located at the same site. FIG. 9C plots GV concentrations calculated from MRI images in N=6 phantoms prepared as in (b). Black bars represent the expected GV concentration. As shown, the alignment of measured concentrations to the expected values provides fingerprint identification of the two GV types (Halo and Mega).

FIG. 10A shows diagram of the clustering experiment using biotinylated Ana GVs and streptavidin (SA). FIG. 10B shows dynamic light scattering (DLS) measurement of the size distributions of biotinylated GVs with SA (dashed), biotinylated GVs without SA (black solid) and non-biotinylated GVs with SA (gray solid). FIG. 10C shows finite element model of the magnetic field pattern expected from individual and clustered GVs. FIG. 10D shows representative T2*-weighted (T2*w) and T2-weighted (T2w) images (echo time=144 msec) and QSM maps (scaled linearly from −2 to 20 ppb) of agarose phantom wells containing GVs with the indicated biotinylation state and presence or absence of SA. FIGS. 10E-G show average in R2*, R2 and $\Delta\chi$ relative to buffer. N=4. Error bars represent SEM. All the GV samples contained Ana GVs at 0.57 nM.

FIGS. 11A-C show plots of $\Delta R2^*$, $\Delta R2$ and $\Delta X$, respectively, of samples with the various SA-to-GV ratio and the two control samples. The ratios are listed below the graph, and the values are relative to sample containing PBS buffer. N=3; error bars represent SEM. FIG. 11D shows TEM images of the most clustered GV sample and FIG. 11E shows TEM images of an unclustered control. Note that the clustered image shows greater number of GVs because clusters are sparsely distributed on the TEM grid.

DETAILED DESCRIPTION

Figure 1:
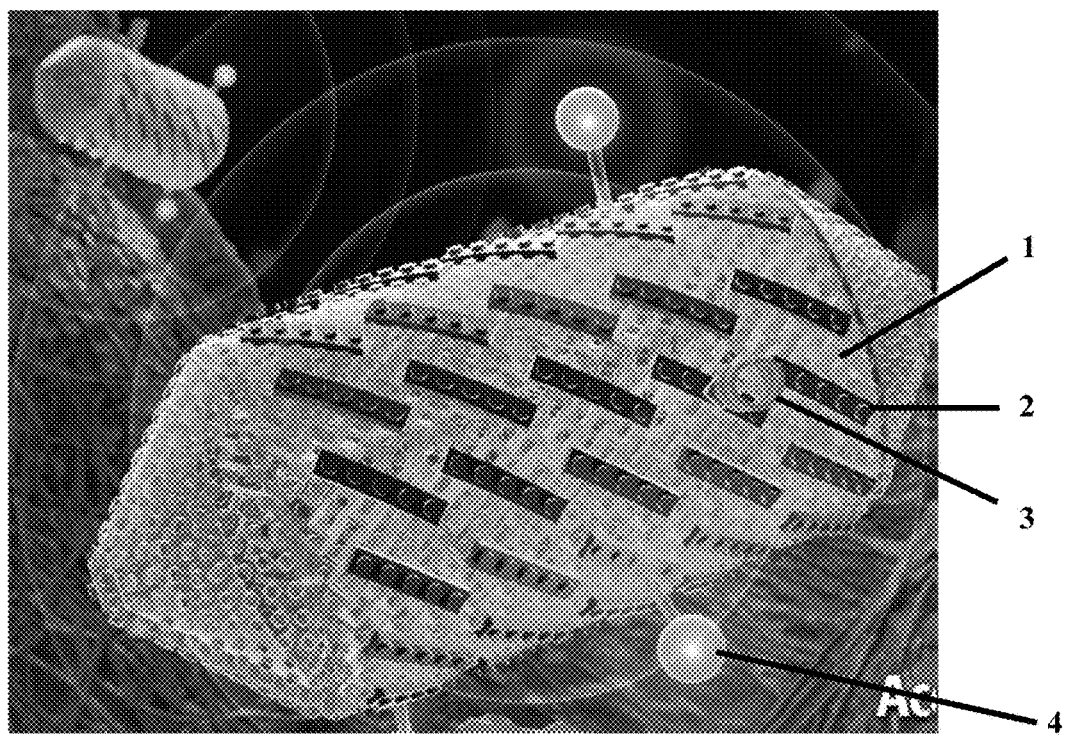

Provided herein are gas-filled protein structures (GVPS), also referred to as "gas vesicles" (GVs), and related compositions methods and systems for use in contrast enhanced magnetic resonance imaging of a target site alone or in combination with ultrasound.

The term "contrast enhanced imaging" or "imaging", as herein indicates a visualization of a target site performed with the aid of a contrast agent administered to the target site to improve the visibility of structures or fluids by devices process and techniques suitable to provide a visual representation of a target site when imaged. Accordingly, contrast agent in the sense of the disclosure is a substance that enhances the contrast of structures or fluids within the target site, producing a higher contrast image for evaluation.

The term "target site" as used herein indicates an environment comprising one or more targets intended as a combination of structures and fluids to be contrasted, such as cells. In particular, the term "target site" refers to biological environments such as cells, tissues, organs in vitro in vivo or ex vivo that contain at least one target. A target is a portion of the target site to be contrasted against the background (e.g. surrounding matter) of the target site. Accordingly, a target can include any molecule, cell, tissue, body part, body cavity, organ system, whole organisms, collection of any number of organisms within any suitable environment in vitro, in vivo or ex vivo as will be understood by a skilled person. Exemplary target sites include collections of microorganisms, including, bacteria or archaea in a solution in vitro, as well as cells grown in an in vitro culture, including, primary mammalian, cells, immortalized cell lines, tumor cells, stem cells, and the like. Additional exemplary target sites include tissues and organs in an ex vivo colture and tissue, organs, or organs systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term "individual" or "subject" or "patient" as used herein in the context of imaging includes a single plant or animal and in particular higher plants or animals and in particular vertebrates such as mammals and more particularly human beings. Types of ultrasound imaging of biological target sites include abdominal ultrasound, vascular ultrasound, obstetrical ultrasound, hysterosonography, pelvic ultrasound, renal ultrasound, thyroid ultrasound, testicular ultrasound, and pediatric ultrasound as well as additional ultrasound imaging as would be understood by a skilled person.

In embodiments, herein described the contrast enhanced imaging of a target site is performed by imaging the target site with magnetic resonance imaging alone or in combination with other imaging techniques such as ultrasound imaging.

The term "magnetic resonance imaging" or "MRI" as used herein indicates an imaging technique performed by applying a magnetic field to a target site and detecting the resulting magnetic resonance. In MRI, a target site is positioned within a magnet provided by an MRI scanner where the magnetic field is used to align the magnetization of some atomic nuclei in the target site, and radio frequency magnetic fields are applied to systematically alter the alignment of this magnetization. This causes the nuclei to produce a rotating magnetic field detectable by the scanner, and this information is recorded to construct an image of the scanned area of the target site. The magnetic resonance of the target site is then detected, and the resulting data are analyzed to produce an image. MRI is thus performed based on nuclear magnetic resonance (NMR) property of nuclei of atoms inside the target site. For example, MRI is commonly used in radiology to visualize a target site formed by internal structures of the body of an individual. In this example, MRI makes use of the property of nuclear magnetic resonance (NMR) to image nuclei of atoms inside the body.

Exemplary MRI systems comprise clinical systems operating at a magnetic strength around 1.5 Tesla (T), as well as commercial system which can run from earth magnetic field around 50 µT to high magnetic field such as 21 T and other systems identifiable by a skilled person.

The term "susceptibility-based MRI" as used herein refers to MRI based on susceptibility and/or proton relaxivity. The susceptibility-based MRI can be performed by either detecting the volume susceptibility of the volume areas at the target site, such as in QSM, or measuring the relaxation rate of nuclear spins of atoms in the volume areas, such as in T1, T2, and T2* MRI. T1 refers to longitudinal relaxation time and T2 refers to transverse relaxation time. T2* is a combination of T2 relaxation and relaxation caused by magnetic field inhomogeneities. In some embodiments, the nuclear spin can be the nuclear spin of the $^1H$ proton of water or $^{19}F$ of fluorine-containing polymers at the target site. The nuclear spin of an atom refers to the intrinsic spin angular momentum of the atom. Associated with the nuclear spin is a nuclear magnetic moment, which allows for magnetic interactions with its environment, which in turn allows for MRI.

The term "CEST" as used herein refers to MRI based on Chemical Exchange Saturation Transfer (CEST). CEST works by having exchangeable solute protons that resonate at a frequency different from the bulk water protons when selectively saturated using RF irradiation. This saturation is subsequently transferred to the bulk water by the solute protons exchanging with the surrounding water protons, resulting in a slight attenuation of the water signal. Because the bulk water has significantly more protons than the solute, each exchange typically results in replacing a saturated solute proton with an unsaturated water proton (which, then, becomes saturated), thereby magnifying the saturation such that each Xe-based molecule saturates hundreds of water molecules. If a solution is used where the solute protons have a fast exchange rate and long saturation time, then the prolonged irradiation causes an enhancement to the saturation effect to the point that the solute can be imaged indirectly by plotting the water saturation normalized by the signal without saturation as a function of saturation frequency (aka CEST spectrum). As a convention, the water frequency is given a baseline score of 0 ppm.

The term "Hyper-CEST" as used herein refers to a CEST technique that utilizes hyperpolarized agents, such as $^{129}Xe$. The hyperpolarization occurs when rubidium vapor is energized by polarized light, then the hyperpolarization of the rubidium is transferred to xenon nuclei. This increases the proportion of spin-up oriented xenon nuclei. Using Hyper-CEST with Xe based contrast allows imaging at much lower concentrations (i.e. increased sensitivity) compared to susceptibility-based MRI techniques (e.g. T1, T2/T2*, QSM). However, unlike T2/T2* and QSM, multiparametric GV multiplexing is not available in Hyper-CEST, since the Hyper-CEST cannot measure T2/T2* and QSM of the surrounding nuclear spin. Another difference between the two techniques is that Hyper-CEST requires xenon as the contrast agent gas, and GVs need to be exposed to sufficient amount and sufficiently polarized xenon gas before acting as a Hyper-CEST contrast agent, and this requirement often constitutes a limitation to the usage of Xenon Hyper-CEST.

In contrast enhanced imaging performed by MRI, an image contrast can be obtained by the measurement of relaxation rates based on the nuclei relaxation to the ground state after being excited by an radio frequency pulse. T2 or T2* maps can be created based on the relaxation time itself, also known as relaxometry. T2 or T2* maps can be constructed by applying two or more different times of echo (TE) and a long time of repetition and plotting the relaxation time constant or the relaxation rate as the intensity of the image. The relaxation rate can be obtained from curve fitting to the exponential decay observed in the multiple echo experiments.

An image contrast can be further enhanced by weighting. Two forms of weighting for susceptibility-based MRI are T1 and T2, based on which relaxivity value is to be enhanced. T1-weighted, also known as spin-lattice weighting and sometimes indicated as T1WI, allow magnetization to recover before the magnetic resonance signal is measured by changing the repetition time. The repetition time is the time, measured in milliseconds, from the application of an excitation pulse to the application of the next pulse, which shows how much of the longitudinal magnetization recovers between each pulse. T2-weighted, or spin-spin weighting and sometimes indicated as T2WI, allows magnetization to decay before the magnetic resonance signal is measured by changing the echo time. The echo time refers to time, measured in milliseconds, between the application of radiofrequency excitation pulse and the peak of the signal induced in the coil. For T2-weighted images, the selected TE values should be close of the T2 of the tissue. In general, T2-weighted images are produced by using longer TE and TR times, while T2-weighted images are produced by using short TE and TR times. The spin-spin weighting rate can also be denoted T2*. T2* can be considered an "observed" or "effective" T2 (which includes effects from the magnetic field inhomogeneity), whereas the first T2 can be considered the "natural" or "true" T2 of the tissue being imaged (i.e. purely spin-spin interaction). T2* is less than or equal to T2. In MRI, T2* is usually measured by variants of gradient echo pulse sequences and T2 by variants of spin echo pulse sequences. The specific images formed with a pre-set echo time (TE) in the form of gradient echo or spin echo are referred to as T2*- or T2-weighted images or maps.

As used herein, T2 imaging and T2* imaging generally refers to any T2 based and T2* based imaging techniques, including both using multiple spin echo or gradient echo sequences such as in T2/T2* maps or a single spin or gradient echo such as in T2/T2*-weighted maps.

In contrast enhanced imaging performed by MRI, an image contrast can be further enhanced by quantitative susceptibility mapping (QSM) which utilizes phase images to generate a 3D susceptibility distribution. The mapping can be performed by various techniques (COSMOS, MEDI, TKD, etc.), but ultimately the result is a calculated determination of the underlying susceptibility value at each pixel/voxel of the image. Theoretically, the susceptibility is approximately linearly proportional to the concentration of the contrast material (in this case, air). Different contrast agent with different volumes would, therefore, produce different delta susceptibility per contrast agent.

In contrast enhanced imaging performed by MRI, various contrast agent can be used as it will be understood by a skilled person, including cellular and molecular processes inside living animals and patients. In particular, existing contrast agents for MRI are primarily based on heavy metal chelates [3], superparamagnetic iron oxides and in particular superparamagnetic iron oxide nanoparticles (SPIONs) [4, 5], metalloproteins [6-9], molecules with chemically exchangeable nuclei [10-13] and fluorinated compounds [14]. More particularly, commonly used contrast agents for MRI are chelates of gadolinium, and iodinated agents, as well as SPIONs used as conventional T2 and T2* contrast agents used in MRI applications such as in vivo cell tracking. Further contrast agents are CEST agents with distinct chemical shifts for exchanging nuclei [40, 64], and contrast agents to be used dynamic sensors capable of imaging specific biological activities such as neurotransmission or enzymatic function [8, 58, 73-75], e.g. superparamagnetic structures designed to cluster in response molecular signals of interest leading to an increase or decrease in T2 or T2* contrast [73, 75, 76].

In embodiments herein described, the MRI of target site is performed in connection with the existence of GVPS at the target site. The GVPS can be pre-made ex vivo and subsequently administered to the target site via methods such as direct injection, intravenous injection of GVPS with targeting moiety or intravenous injection of GVPS with tissue tropism. Alternatively, GVPS can also be made in situ by cells, provided that GVPS is genetically encoded in these cells and the cells are capable of expressing GVPS.

The wordings "gas vesicles protein structure" or "GV", "GVP", "GVPS" or "Gas Vesicles" as used herein refer to a gas-filled protein structure intracellularly expressed by certain bacteria or archea as a mechanism to regulate cellular buoyancy in aqueous environments [15]. In particular, gas vesicles are protein structures natively expressed almost exclusively in microorganisms from aquatic habitats, to provide buoyancy by lowering the density of the cells [15]. GVs have been found in over 150 species of prokaryotes, comprising cyanobacteria and bacteria other than cyanobacteria [16, 17], from at least 5 of the 11 phyla of bacteria and 2 of the phyla of archaea described by Woese (1987) [18]. Exemplary microorganisms expressing or carrying gas vesicle protein structure include cyanobacteria such as *Microcystis aeruginosa, Aphanizomenon flos-aquae, Oscillatoria agardhii, Anabaena, Microchaete diplosiphon* and *Nostoc*; phototropic bacteria such as *Amoebobacter, Thiodiclyon, Pelodiclyon*, and *Ancalochloris*; non phototropic bacteria such as *Microcyclus aquaticus*; Gram-positive bacteria such as *Bacillus megaterium*; Gram-negative bacteria such as *Serratia*; and archaea such as *Haloferax mediterranei, Methanosarcina barkeri, Halobacteria salinarium* as well as additional microorganisms identifiable by a skilled person.

In particular, a GV in the sense of the disclosure is a structure intracellularly expressed by cells forming a hollow structure wherein a gas is enclosed by a protein shell, which is a shell made natively entirely of protein. Various chemically modified GV would also be compatible with the imaging methods in the disclosure, which is subject to the identification by a skilled person. In gas vesicles in the sense of the disclosure, the protein shell is formed by a plurality of proteins herein also indicated as Gyp proteins or Gvps, which are expressed by the bacteria or archea and form in the bacteria or archea cytoplasm a gas permeable and liquid impermeable protein shell configuration encircling gas. Accordingly, a protein shell of a GV is permeable to gas but not to surrounding liquid such as water. In particular, GVs' protein shells exclude water but permit gas to freely diffuse in and out from the surrounding media [19] making them physically stable despite their usual nanometer size, unlike microbubbles, which trap pre-loaded gas in an unstable configuration. GVs are typically nanostructures with widths and lengths of nanometer dimensions (in particular with widths of 45-250 nm and lengths of 100-800 nm) but can have lengths up to 2 µm as will be understood by a skilled person. In certain embodiments, the gas vesicles protein nanostructure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. In some embodiments, the gas vesicles protein nanostructures have average dimension larger than 1000 nm. By "average" is meant the arithmetic mean.

GVs in the sense of the disclosure have different shapes and sizes depending on their genetic origins [19]. For example, GVs in the sense of the disclosure can be substantially spherical, ellipsoid, cylindrical, or have other shapes such as football shape or cylindrical with cone shaped end portions depending on the type of bacteria providing the gas vesicles.

In some embodiments herein described, the magnetic susceptibility of the gas in the GV, for example air, is different from that of the diamagnetic water at the target site. For example, air has a gas susceptibility of 0.37 ppm under atmospheric pressure while water has a water susceptibility of about −9.0 ppm. Gas under anaerobic or hypoxic condition can be less paramagnetic or even diamagnetic, but the susceptibility should still be higher than −1 ppm. Such difference allows for gas-filled GVs to be used as a contrast agent for MRI to produce susceptibility-based MRI contrast, which could be observed by T2/T2*-weighted imaging, T2/T2* map, quantitative susceptibility mapping and other MRI modalities that can reveal susceptibility difference The term "magnetic susceptibility" or "susceptibility", also denoted as $\chi$, refers to the characteristic of a material, such as water or gas, which is quantified as a dimensionless proportionality constant that indicates the degree of magnetization of a material in response to an applied magnetic field. For example, air has a gas susceptibility of about 0.37 ppm, Xe has a gas susceptibility of about 0.024 ppm, and water has a water susceptibility of about 9.0 ppm. The susceptibility is defined as the proportionality constant between applied magnetic field and induced tissue magnetization.

The susceptibility of a material, such as gas or water, or a target site can be generally defined according to the following equation:

$$M = \chi_v H \quad \text{(Eq. 1)}$$

wherein M is the magnetization of the material or target site, H is the magnetic field strength and $\chi_v$ is the volume susceptibility of the material or target site detected or measured in MRI.

Susceptibility of a given gas-filled protein structure, such as GV, can be measured or calculated as mass susceptibility denoted as $\chi_{mass}$ or molar susceptibility $\chi_{molar}$ based on the volume susceptibility observed in MRI, the concentration and molecular weight of the GV.

The GV-specific mass susceptibility is defined as:

$$\chi_{mass} = (\chi_{v,+GV} - \chi_{v,-GV})/m_{GV,protein} \quad \text{(Eq. 2)}$$

wherein $m_{GV,protein}$ is the mass concentration (mass per unit volume) of the protein components of GVs present inside a specific sample, $\chi_{v,+GV}$ is the volume susceptibility of the sample, and $\chi_{v,-GV}$ is the volume susceptibility of the sample if all GV particles are removed.

The GV-specific molar susceptibility is defined as:

$$\chi_{mol} = \chi_{mass} \times MW_{GV} \quad \text{(Eq. 3)}$$

wherein $MW_{GV}$ is the molecular weight of the specific type of GV inside the sample.

The mass concentration of the GV protein ($m_{GV,protein}$) and the volume of the GV can be determined from the molecular weights of GVs. The length and width of the GVs can be quantified from TEM images, and geometric calculations can be performed to derive the molecular weights of each type of GVs. Protein concentration of GVs can be measured by standard protein concentration determination assay, such as Bradford assay and Pierce 660 assay as will be understood by a person skilled in the art. Details about how to measure the GV geometry and concentrations can be found in the example section. Exemplary measurement of geometrical, optical, magnetic properties and concentration relationship of three types of gas vesicles are listed in Table 1.

In general, the molar and mass susceptibility of a given GV type are determined by the geometrical information of the GV, including volume, shape, dimension and surface area etc. The surface of the GV particles can be estimated from the shape and dimension of the particles. The GV-specific molar susceptibility is predominantly determined by the volume of the GV particles. The GV-specific mass susceptibility is predominantly determined by the volume to surface ratio of the GV particles. As a person skilled in the art will understand, GV types with substantially different volume will have substantially distinct molar susceptibility and GV types with substantially different volume to surface ratio will have substantially distinct mass susceptibility. In embodiments that the primary structural proteins in GVs, such as GvpA and GvpC, are genetically engineered, if the genetic engineering does not influence the volume and shape of the GVs, the susceptibility of the GV are expected to be unaltered.

Volume susceptibility of a sample can be measured experimentally by MRI as would be understood by a person skilled in the art. Algorithms used for such measurement include "quantitative susceptibility mapping" (QSM) as described above and others identifiable to a person skilled in the art.

The volume susceptibility of a GVPS type at a specific concentration can be directly detected in MRI (for example, Example 1). To obtain GV-specific molar and mass susceptibility, the volume magnetic susceptibility of a concentration series of samples containing the contrast agents can be measured. The volume magnetic susceptibility is then plotted as a function of the GV molar concentrations. The slope of the line represents the molar susceptibility. The value of the slope is derived from the linear regression fitting for the plot core. This concentration series can be performed in vitro and at specific tissue of interest in vivo.

Exemplary molar and mass susceptibility of GV types from Ana, Halo and Mega which are substantially distinct as used herein are also shown in the Example section. In particular, Mega GVs, Ana GVs and Halo GVs have a molar susceptibility of about 3.52, 18.53, and 22.2 ppb/nM respectively and a mass susceptibility of about 39.2, 57.2, and 80.9 ppb/[gm/ml], respectively.

In embodiments herein described, GVs in the sense of the disclosure is also characterized by their relaxivity. In MRI methods, the term "relaxivity" indicates the degree of the contrast agent to which the agent can increase the longitudinal or transverse water relaxation rate constant normalized to concentration of the contrast agent. In particular, the relaxivity of a MRI contrast agent reflects how the relaxation rates of a solution change as a function of concentration.

As a person skilled in the art will understand, relaxation time and relaxation rates are inverses of each other. The values for T1, T2 and T2* are relaxation times and typically measured in milliseconds (ms). The corresponding relaxation rates are measured in units of second$^{-1}$ or Hertz. Relaxation rates corresponding to T1, T2 and T2* are typically designed by the symbols R1, R2 and R2*, wherein $$R1 = \frac{1}{T1} \quad \text{(Eq. 4)}$$

$$R2 = \frac{1}{T2} \quad \text{(Eq. 5)}$$

$$R_2^* = \frac{1}{T_2^*} \quad \text{(Eq. 6)}$$

Since a contrast agent can affect the two relaxation rates, R1 and R2, individually, there are two corresponding relaxivities, denoted $r_1$ and $r_2$, in which $r_1$ is the longitudinal relaxivity and $r_2$ is the transverse relaxivity.

Using $R_2$ as an example, the correlation between the relaxation rate and the relaxivity of a MRI contrast agent can be defined as follows:

$$R_2 = R_2^0 + r_2 C \quad \text{(Eq. 7)}$$

wherein $R_2$ is the relaxation rate with the presence of the contrast agent, $R_2^0$ is the relaxation rate without the presence of the contrast agent, C is the molar concentration of the contrast agent and $r_2$ is the relaxivity or relaxivity constant of the agent.

Similarly, $r_2^*$ can be defined as follows:

$$R_2^* = \frac{1}{T_2^*} = R_2^{*,0} + r_2^* C \quad \text{(Eq. 8)}$$

Analogous to the procedure of deriving molar and mass susceptibility, the relaxation rates ($R_1$, $R_2$ or $R_2^*$) of a contrast agent can be measured with the contrast agents at different concentrations and plotted as a function of concentrations by MRI imaging a given contrast agent type (e.g. GVPS type) at different concentrations against a constant target site composition. The slope of the lines represents $r_1$, $r_2$ or $r_2^*$ and can be obtained by linear regression fitting. Exemplary measurement of $r_2$ and $r_2^*$ are shown in Example 1 (see in particular FIG. 2, panels g and h), where the T2* relaxation rate (i.e. R2*) is measured for different concentrations of Ana GVs. The value of the slope from the linear regression fitting of the plot corresponds to r2* relaxivity. Similarly, T2 relaxation rate (i.e. R2) is measured for different concentrations of Ana GVs. The value of the slope from the linear regression fitting of the plot corresponds to r2 relaxivity.

Exemplary r2 and r2* relaxivity of GV types from Mega, Ana and Halo are shown in the Example section (see in particular Table 1). For example, exemplary Mega GVs, Ana GVs and Halo GVs shown in the examples have a r2* relaxivity of about 0.280, 1.19 and 0.89 sec$^{-1}$/nM or about 3.11, 3.66 and 3.24 sec$^{-1}$/[mg/mL]. Mega GVs, Ana GVs and Halo GVs have a r2 relaxivity of about 0138, 0.67 and 0.273 sec$^{-1}$/nM or about 1.53, 2.06 and 1.00 sec$^{-1}$/[mg/mL].

At the high magnetic field (>1 T) that most MRI machine possess, GVs are expected to have negligible r1 relaxivity. Exemplary r1 relaxivities of GV types from Mega, Ana and Halo are shown in Example 1 (see in particular FIG. 4, panels j-l).

It should be noted that r2 and r2* values experimentally measured for a type of GVPS would also depend on the distribution of GVPS inside the sample. Herein described are GVPS homogenously distributed in cylindrical shaped wells, and the r2 and r2* values are recorded from the intensity of the images of the center of the wells disregarding the contrast at the rim of the wells (for example, FIGS. 3A-D). These r2 and r2* values are predicted to be different from those values obtained from the same quantity of GVPS, if GVPS are administered at a single point source and diffuse into the tissue. A skilled person should characterize r2 and r2* values of GVPS in phantoms that are as analogous to the application scenario as possible.

Accordingly, in methods and systems of the present disclosure and related compositions and contrast agents, a GV type or types can be used as a contrast agent in MRI imaging which allows non-toxic, highly sensitive and robust contrast in MRI at sub-nanomolar concentrations, with the optional ability of background erasure and/or multiplexing.

In some embodiments herein described, a method to provide a magnetic resonance imaging of a target site contrasted with a contrast agent comprising gas vesicle protein structure (GVPS) type is described. In the method, the contrast agent comprises a gas vesicle protein structure (GVPS) type which contains a gas having a gas susceptibility. In the method, the bulk material of the target site has a bulk material susceptibility and the gas susceptibility is substantially distinct from the bulk material susceptibility. Substantially distinct is defined as having a difference of at least 3 ppm. The method comprises imaging a target site contrasted with GVPS to obtain an MRI image by detecting volume susceptibility ($\chi$) of the target site or relaxation rates (R2 or R2*) of nuclear spins of an atom in the bulk material. The GVPS contained in the contrast agent can be administered to the target site or expressed in situ in the cells at the target site.

The MRI image can be obtained by quantitative susceptibility mapping (QSM), T2/T2* mapping, or T2/T2*-weighted mapping or other image enhancing methods identifiable to a person skilled in the art. QSM method usually provides the highest sensitivity but may not be available in some in vivo applications due to its requirement for imaging quality and time. In cases where large change of tissue susceptibility is present, for example, near lung or air passage way, T2* weighted imaging or T2* map will likely have artifact as can be judged by the skilled person, and therefore T2 weighted imaging or T2 map should be used instead.

In some embodiments, the MRI images are obtained by measuring volume susceptibility of the target site, such as quantitative susceptibility mapping (QSM), especially in cases when the susceptibility of the target site can be distinguished in the MRI images by the skilled person at the accuracy of at least 1 ppb. The desired concentration of GVPS can be calculated from the molar or mass susceptibility values of GVPS. The higher the molar susceptibility of the GV, the lower the concentration is required to achieve certain accuracy. For example, among the Mega, Ana and Halo GV, Halo GV has the highest molar susceptibility of 22.2 ppb/nM and Mega GV has the lowest molar susceptibility of 3.52 ppb/nM. Therefore, to achieve the accuracy of 1 ppb, the required concentration of Halo GVs is about 45 picomolar or 12.4 µg/mL and the required concentration of Mega GV is about 284 picomolar.

In some embodiments, the MRI images are obtained by measuring relaxation rates of nuclear spins of an atom in the bulk material through the acquisition of an image series, such as T2/T2* mapping or weighted by the relaxation rate of nuclear spins such as in T2/T2*-weighted mapping. The nuclear spin can be, for example, of the $^1$H proton of water or $^{19}$F of fluorine-containing polymers at the target site.

The MRI pulse sequences used include T2-weighted and T2*-weighted sequences. A sequence of such images can be acquired for processing into T2 maps, T2* maps or quantitative susceptibility maps. In addition, images with alternative weighing (e.g. T1, proton or diffusion) can also be acquired to obtain anatomical background.

In these scenarios, the echo time (TE) can be specified based on the relaxivity parameters to maximize the contrast in T2*-weighted or T2-weighted images. For example, if the skilled person has measured the background tissue to have R2*=12 sec$^{-1}$ and R2=10 sec$^{-1}$, the required 1% change on a T2* and T2 map would be 0.12 and 0.1 sec$^{-1}$, respectively. For T2 and T2*-weighted images, the parameter of optimal echo time needs to be determined, so that the parameter $$\frac{e^{R_2^0 \cdot t} - e^{(R_2^0 + r_2 C) \cdot t}}{e^{R_2^0 \cdot t}}$$

is maximal (t being the echo time) and equal to the desired contrast change, e.g. 1%. The echo time refers to time between the application of radiofrequency excitation pulse and the peak of the signal induced in the coil. It is typically measured in milliseconds, so the value may need to be scaled if R2/R2* are given in seconds.

This method is applicable to many different field strength of the static magnet used in a variety of MRI equipment, including clinical and preclinical MRI.

In certain embodiments, imaging the target site comprises applying an external magnetic field to the target site in the subject, transmitting a radio frequency (RF) signal from a transmitter to the target site, and receiving MRI data at a receiver. The MRI data can be analyzed using a processor, such as a processor configured to analyze the MRI data and produce an MRI image from the MRI data. In certain embodiments, the MRI data detected by the receiver includes an MRI signal (e.g., a radio frequency MRI signal of the target site of the subject). In certain embodiments, the method includes obtaining a MRI data (e.g., signal) of the target site, and analyzing the MRI data (e.g., signal) to produce an MRI image of the target site. The MRI data (e.g., signal) can be obtained using a standard MRI device, or can be obtained using an MRI device configured to specifically detect the contrast agent used. Obtaining the MRI data (e.g., signal) can include detecting the MRI data (e.g., signal) with an MRI detector.

In certain embodiments, MRI data are obtained by applying to a subject a static magnetic field, a rapidly switching gradient field for spatial coding, and RF pulses with frequency matched such that the RF pulses trigger magnetic resonance signals from excited atomic nuclei at the target site. For example, an atomic nucleus can produce magnetic resonance signals when the RF pulse has a frequency that matches the resonance frequency (measured in chemical shifts (δ) in parts per million (ppm)) of the atomic nucleus. In such cases, the nucleus absorbs the RF pulse energy to become excited, and releases a magnetic resonance signal when the excited nucleus subsequently relaxes to an unexcited state after characteristic time periods. The magnetic resonance signals are detected by RF receiving antennas and digitized to generate the MRI data. The MRI data is analyzed using any known method of analyzing MRI data. In certain instances, the MRI data is analyzed to reconstruct the MRI image. For example, the MRI image is reconstructed from the MRI data by decoding the spatial information encoded in the MRI data using a linear reconstruction algorithm, such as Fourier transformation.

In certain embodiments, the magnetic field has a strength between 50 µT and more than 20 T, including magnetic strength used in earth-field MRI, low-field MRI, clinical and preclinical MRI.

In some embodiments, the contrast agents are administered to the target site with the selected GVPS type at a sub-nanomolar concentration (≤0.1 mg/mL), within the range of other protein-based MRI reporters such as haem-containing cytochromes, ferritin, aquaporin and chemical exchange saturation transfer polypeptides.

In some exemplary embodiments in which Ana GVs are used in the contrast agent, the Ana GVs are detectable by QSM at concentrations below 300 pM (see Example 1). In some cases, GVs at such concentrations can produce negligible T1 contrast and have an insignificant effect on proton density due to water exclusion.

In methods herein described, administering the contrast agent can be performed in any way suitable to deliver a GV to the target site to be imaged, either in vivo or in vitro.

In some embodiments, in which the target site is the body of an individual or a part thereof, the contrast agent can be administered to the target site locally or systemically.

The wording "local administration" or "topic administration" as used herein indicates any route of administration by which a GV is brought in contact with the body of the individual, so that the resulting GV location in the body is topic (limited to a specific tissue, organ or other body part where the imaging is desired). Exemplary local administration routes include injection into a particular tissue by a needle, gavage into the gastrointestinal tract, and spreading a solution containing GVs on a skin surface.

The wording "systemic administration" as used herein indicates any route of administration by which a GV is brought in contact with the body of the individual, so that the resulting GV location in the body is systemic (not limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

Accordingly, in some embodiments of methods herein described, administering a contrast agent can be performed topically or systemically by intradermal, intramuscular, intraperitoneal, intravenous, subcutaneous, intranasal, rectal, vaginal, and oral routes. In particular, a contrast agent can be administered by infusion or bolus injection, by absorption through epithelial or mucocutaneous linings (e.g., oral mucosa, vaginal, rectal and intestinal mucosa, etc.) and can optionally be administered together with other biologically active agents. In some embodiments of methods herein described, administering a contrast agent can be performed by injecting the contrast agent into a subject at the target site of interest, such as in a body cavity or lumen. In some embodiments, it can be performed by spreading a solution containing the contrast agent on a region of the skin. For GVPS contrast agents, the gas used for contrast can be infused into the GV prior to administration, or the GV (being in a non-collapsed state) can self-infuse air from the surrounding solution. Once the GVs reaches the target site, the target site can be contrast imaged.

In embodiments herein described, GVs in the sense of the disclosure are capable of withstanding pressures of several kPa. but collapse irreversibly at a pressure at which the GV protein shell is deformed to the point where it flattens or breaks, allowing the gas inside the GV to dissolve irreversibly in surrounding media, herein also referred to as a critical collapse pressure, or selectable critical collapse pressure, as there are various points along a collapse pressure profile.

A collapse pressure profile as used herein indicates a range of pressures over which collapse of a population of GVs of a certain type occurs. In particular, a collapse pressure profile in the sense of the disclosure comprise increasing acoustic/hydrostatic collapse pressure values, starting from an initial collapse pressure value at which the GV signal/optical scattering by GVs starts to be erased to a complete collapse pressure value at which the GV signal/optical scattering by GVs is completely erased. The collapse pressure profile of a set type of GV is thus characterized by a mid-point pressure where 50% of the GVs of the set type have been collapsed (also known as the "midpoint collapse pressure"), an initial collapse pressure where 5% or lower of the GVs of the type have been collapsed, and a complete collapse pressure where at least 95% of the GVs of the type have been collapsed. In embodiments herein described a selectable critical collapse pressure can be any of these collapse pressures within a collapse pressure profile, as well as any point between them. The critical collapse pressure profile of a GV is functional to the mechanical properties of the protein shell and the diameter of the shell structure. The profiles under hydrostatic pressure and under acoustic pressure are different, with the points on the acoustic pressure profile being higher in pressure than the hydrostatic profile at the midpoint collapse pressure point, at least.

It has been surprisingly found that the critical collapse pressure is also functional to the manner in which the forces are applying the pressure to the GV shell. Accordingly, different ways of applying pressure on a set GVs result in different types of critical collapse pressures associated to the set GV. As a consequence, GVs in the sense of the disclosure are associated to more than one critical collapse pressure profile, depending on whether the pressure on the GV is applied in a hydrostatic manner (hydrostatic pressure), or applied in an acoustic manner (acoustic pressure).

The term "hydrostatic pressure" as used herein indicates the pressure exerted by a fluid at a given point within the fluid, absent fluid motion. Hydrostatic pressure includes pressure due to gravity, which pressure increases in proportion to depth measured from the surface because of the increasing weight of fluid exerting downward force from above. In addition, the hydrostatic pressure may include pressure due to forces applied to the fluid by solid surfaces adjoining the fluid, or by another fluid, such as a gas. As used herein, hydrostatic pressure does not include pressure due to sound waves.

The term the "acoustic pressure" as used herein indicates the pressure exerted by a sound wave, such as ultrasound wave, propagating through a medium. In ultrasound imaging, this wave is typically generated by an ultrasound transducer, and the pressure resulting at any time and point in the medium is determined by transducer output and patterns of constructive and destructive interference, attenuation, reflection, refraction and diffraction. Ultrasound images are generated by transmitting one or more pulses into the medium and acquiring backscattered signals from the medium, which depend on medium composition, including the presence of contrast agents.

Accordingly, in some embodiments herein described each GV type has a hydrostatic collapse pressure profile and an acoustic collapse pressure profile.

It has been found that in GVs according to the present disclosure the acoustic collapse pressure is higher than the hydrostatic collapse pressure. In particular, an acoustic collapse pressure profile of a given GV type is always shifted to higher pressures compared to its hydrostatic collapse pressure profile. The approximate mid-point acoustic collapse pressure, Pa, can be related to the mid-point hydrostatic collapse pressure, Ph, using a linear expression. This linear expression includes a non-zero positive constant, C, and a positive slope, M, such that $$Pa=C+M*Ph \qquad \text{(Eq. 9)}$$

In embodiments, herein described, for a given GV type, a Pa can be predicted, to within ±10% error, from a measured Ph value, using the parameters C=475 and M=0.64. An even more precise prediction can be made for GVs that share a substantially similar shell structure.

In embodiments, herein described, for a given GV type, the spread of the acoustic collapse pressure profile can similarly be predicted from the spread of the hydrostatic collapse pressure profile using a linear relationship with positive constant C and positive slope M, such that ΔPa=C+M*ΔPh. In particular, for a ΔPh value measured for a given GV type, the corresponding Pa can be predicted to within 30 kPa using the parameters C=6.32 and M=1.15.

In embodiments herein described, the hydrostatic collapse pressure of a particular GV can be approximated by a sigmoidal function with a defined mid-point and transition width. For example, it can be defined according to Equation (2).

$$f(p)=(1+e^{(p-p_c)/\Delta p})^{-1} \qquad \text{(Eq. 10)}$$

with $p_c$ defined as the mid-point and $\Delta p$ defined as the transition width. These parameters are determined for each GV type by measuring collapse as a function of pressure and fitting the resulting data with this equation, or predicted based on the GV's molecular characteristics.

For example, the hydrostatic collapse pressure can be measured by detecting a hydrostatic collapse behavior of the GV structures using pressurized absorbance spectroscopy, in which the optical density of GVs is measured under increasing hydrostatic pressure.

In embodiments herein described, the collapse behavior of GVs under ultrasound exhibits a spectral pattern, as the GVs can collapse over a range or spectra of continuous increasing acoustic collapse pressure values, starting from an initial collapse pressure value at which the GV signal starts to be erased to a complete collapse pressure value at which the GV signal is completely erased.

The acoustic collapse pressures of a given GV type can be characterized by an acoustic collapse pressure profile, which is a normalized sigmoid function f(p) defined as follows:

$$f(p)=(1+e^{(p-p_c)/\Delta p})^{-1} \qquad \text{(Eq. 11)}$$

where p is the applied pressure, $p_c$ is the collapse mid-point and $\Delta p$ is the variance, the latter two being parameters obtained from fitting with a sigmoid function. The acoustic collapse pressure profile shows normalized ultrasound signal intensities as a function of increasing pressures.

Figure 4:
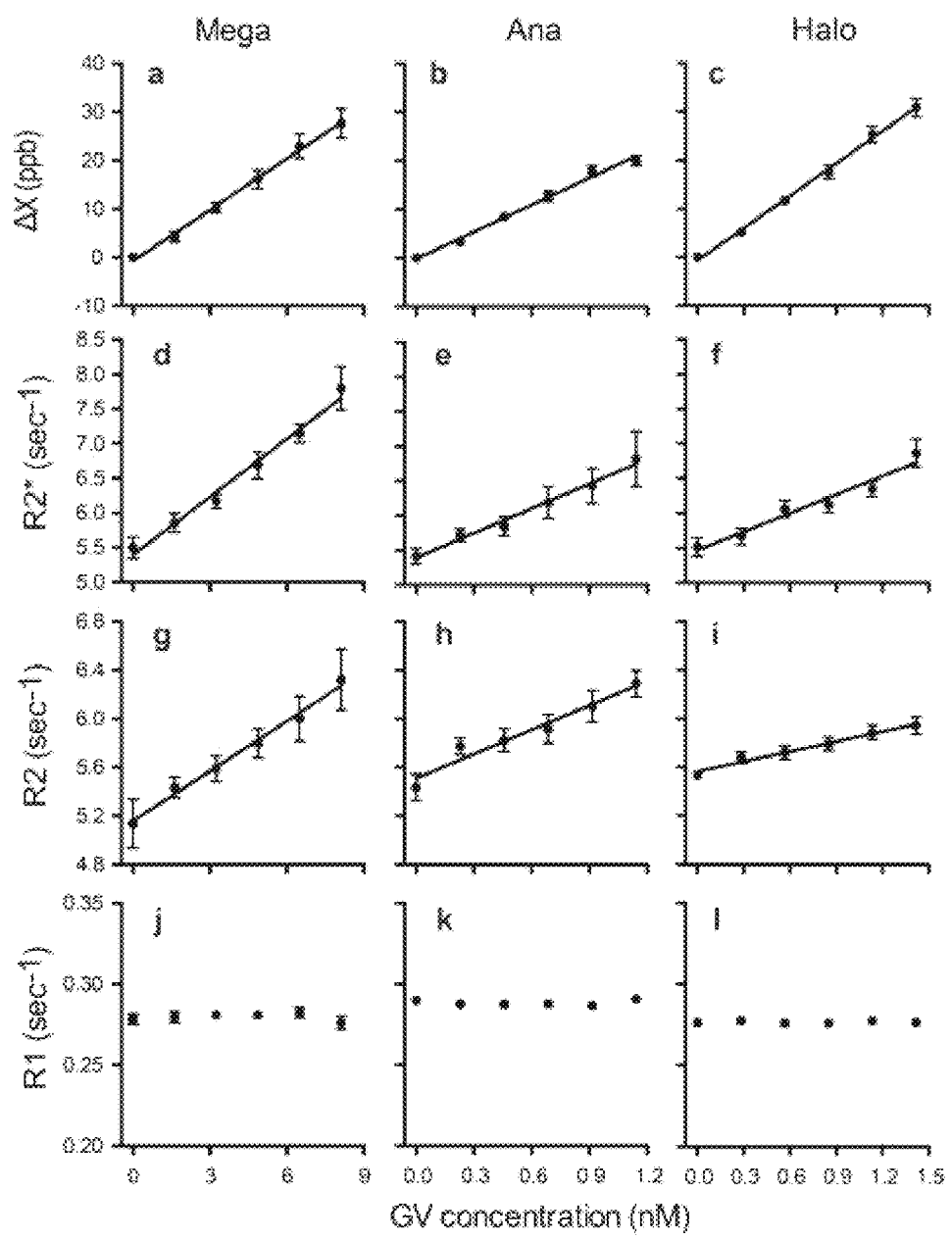
FIG. 4 shows in some embodiments molar susceptibility and T2*, T2 and T1 relaxivities of the three types of GVs used in this study. Panels a-c, susceptibility in the unit of parts per billion (ppb), Panels d-f, T2* relaxometry, Panels g-i, T2 relaxometry and Panels j-l T1 relaxometry measurements on GVs from *Bacillus megaterium* (Mega, Panels a, d, g, j), *Anabaena flos-aquae* (Ana, Panels b, e, h, k) and *Halobacterium salinarum* (Halo, c, f, i, l). Error bars represent SEM. N=9 for all susceptibility and R2* measurements. For T2 and T1 measurements, N=6 for Mega and Ana and N=9 for Halo. Relaxivities calculated from linear regression fitting are listed in Table 1.

The acoustic collapse pressure profile of a given GV type can be determined by imaging GVs with imaging ultrasound energy after collapsing portions of the given GV type population with a collapsing ultrasound energy (e.g. ultrasound pulses) with increasing peak positive pressure amplitudes to obtain acoustic pressure data point of acoustic pressure values, the data points forming an acoustic collapse curve. The acoustic collapse pressure function f(p) can be derived from the acoustic collapse curve by fitting the data with a sigmoid function such as a Boltzmann sigmoid function. Exemplary acoustic collapse pressure curves construed accordingly for a set of three different GVs are shown in FIG. 4, panel c of U.S. application Ser. No. 15/613,104). Detailed description of how to construe hydrostatic and acoustic collapse pressure curves for different GV types can be found, for example in U.S. application Ser. No. 15/613,104, which is incorporated herein by reference in its entirety.

Accordingly, acoustic collapse pressure profile in the sense of the disclosure include a set of initial collapse pressure values, a midpoint collapse pressure value and a set of complete collapse pressure values. The initial collapse pressures are the acoustic collapse pressures at which 5% or less of the GV signal is erased. A midpoint collapse pressure is the acoustic collapse pressure at which 50% of the GV signal is erased. Complete collapse pressures are the acoustic collapse pressures at which 95% or more of the GV signal is erased.

The initial collapse pressures can be obtained by solving the fitted equations for p such that $f(p) \leq 0.05$. The midpoint collapse pressure can be obtained by solving the fitted equations for p such that $f(p)=0.5$. The complete collapse pressures can be obtained by solving the fitted equations for p such that $f(p) \geq 0.95$.

In particular, for a GV type, an acoustic collapse pressure can be more than twice the hydrostatic collapse pressure for the same GV as shown by a comparison of corresponding curves built based on the detected acoustic collapse pressure values according to equations (11) and on detected hydrostatic collapse pressure value according to Equation (10).

Accordingly, in methods and systems of the present disclosure and related compositions and contrast agents, identification of the acoustic collapse pressure for a GV type can be used to apply an acoustic pressure which allows selective collapsing or imaging of the GV in ultrasound.

The term "ultrasound imaging" or ultrasound scanning" or "sonography" as used herein indicate imaging performed with techniques based on the application of ultrasound. Ultrasound refers to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein refers in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. A contrast agent sometimes used with ultrasound imaging are microbubbles created by an agitated saline solution, which works due to the drop in density at the interface between the gas in the bubbles and the surrounding fluid, which creates a strong ultrasound reflection. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect to measure and visualize movement, such as blood flow rates. Types of Doppler imaging includes continuous wave Doppler, where a continuous sinusoidal wave is used; pulsed wave Doppler, which uses pulsed waves transmitted at a constant repetition frequency, and color flow imaging, which uses the phase shift between pulses to determine velocity information which is given a false color (such as red=flow towards viewer and blue=flow away from viewer) superimposed on a grey-scale anatomical image. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body. Other ultrasound techniques and devices suitable to image a target site using ultrasound would be understood by a skilled person.

Applying ultrasound refers to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging task and, in some methods described herein, collapsing GVs. To create images, particularly 2D and 3D imaging, scanning techniques can be used where the ultrasound energy is applied in lines or slices which are composited into an image.

In some embodiments, the ultrasound imaging herein described can comprising collapsing the GVPS type in the contrast agent by applying collapsing ultrasound to the target site and/or imaging the GVPS type in the contrast agent by applying imaging ultrasound to the target site.

In some embodiments, imaging the target site can be performed by scanning an ultrasound image of the target site in a subject. In some cases, imaging the target site includes transmitting an imaging ultrasound signal from an ultrasound transmitter to the target site, and receiving a set of ultrasound data at a receiver. The visible image is formed by ultrasound signals backscattered from the target site. The ultrasound data can be analyzed using a processor, such as a processor configured to analyze the ultrasound data and produce an ultrasound image from the ultrasound data. In certain embodiments, the ultrasound data detected by the receiver includes an ultrasound signal, an ultrasound signal reflected by the target site of the subject.

In certain embodiments, the method includes applying a set of imaging pulses from an ultrasound transmitter to the target site, and receiving ultrasound signal at a receiver. In certain instances, the ultrasound signal detected by the receiver includes an ultrasound echo signal. Additional information of ultrasound systems and methods can be found in related publications as will be understood by a person skilled in the art.

Methods for performing ultrasound imaging are known in the art and can be employed in methods of the current disclosure. In certain aspects, an ultrasound transducer, which comprises piezoelectric elements, transmits an ultrasound imaging signal (or pulse) in the direction of the target site. Variations in the acoustic impedance (or echogenicity) along the path of the ultrasound imaging signal causes backscatter (or echo) of the imaging signal, which is received by the piezoelectric elements. The received echo signal is digitized into ultrasound data and displayed as an ultrasound image. Conventional ultrasound imaging systems comprise an array of ultrasonic transducer elements that are used to transmit an ultrasound beam, or a composite of ultrasonic imaging signals that form a scan line. The ultrasound beam is focused onto a target site by adjusting the relative phase and amplitudes of the imaging signals. The imaging signals are reflected back from the target site and received at the transducer elements. The voltages produced at the receiving transducer elements are summed so that the net signal is indicative of the ultrasound energy reflected from a single focal point in the subject. An ultrasound image is then composed of multiple image scan lines.

In some embodiments, imaging the target site is performed by applying or transmitting an imaging ultrasound signal from an ultrasound transmitter to the target site and receiving a set of ultrasound data at a receiver. The ultrasound data can be obtained using a standard ultrasound device, or can be obtained using an ultrasound device configured to specifically detect the contrast agent used. Obtaining the ultrasound data can include detecting the ultrasound signal with an ultrasound detector. In some embodiments, the imaging step further comprises analyzing the set of ultrasound data to produce an ultrasound image.

In certain embodiments, the ultrasound signal has a transmit frequency of at least 1 MHz, 5 MHz, 10 MHz, 20 MHz, 30 MHz, 40 MHz or 50 MHz. For example, an ultrasound data is obtained by applying to the target site an ultrasound signal at a transmit frequency from 4 to 11 MHz, or at a transmit frequency from 14 to 22 MHz.

In the embodiments herein described, the collapsing ultrasound and imaging ultrasound are selected to have a collapsing pressure and an imaging pressure amplitude based on the acoustic collapse pressure profile of the GVPS type used in the contrast agent. The collapsing ultrasound is typically provided at a high ultrasound pressure amplitude in order to collapse the GVs in the contrast agent, while the imaging ultrasound is typically provided at a low ultrasound pressure amplitude to avoid collapsing of the GVs.

The ability of GVPS to both be collapsed by ultrasound and act as an MRI contrast allows them to act as an acoustically modulated reporter, thus creating possibilities for multimodal imaging. In some embodiments herein described, when collapsing ultrasound is used in combination with MRI imaging, acoustically collapsing the GVPS can remotely in situ erase the contrast agent to enable a background-free magnetic resonance imaging of a target site contrasted with the GVPS. The background-free magnetic resonance imaging removes background noise posed by background contrast from endogenous sources [20, 21] by allowing reporters to be identified specifically based on their ultrasound collapse profile.

In some embodiments, a method to provide a background-free magnetic resonance imaging of a target site comprises a MRI imaging used in combination with ultrasound collapsing on a target site contrasted with a contrast agent comprising a GVPS. In the method, the GVPS contains a gas having susceptibility substantially distinct from the susceptibility of the bulk material in the target site. The GVPS also has a selectable acoustic collapse pressure value derived from an acoustic collapse pressure profile of the GVPS type. The method comprises administering to a target site a contrast agent comprising a gas vesicle protein structure (GVPS) type herein described, imaging the target site by applying an external magnetic field to the target site to obtain a first MRI image of the target site, and collapsing the GVPS type by applying collapsing ultrasound to the target site, the collapsing ultrasound applied at a collapsing ultrasound pressure greater than a selectable acoustic collapse pressure value, and after collapsing, imaging the target site by applying an external magnetic field to the target site to obtain a second MRI image of the target site. The MRI imaging parameters used before and after the collapse are identical.

The MRI imaging can be performed by susceptibility-based MRI imaging by measuring the volume susceptibility of the target site or relaxation rate of nuclear spins of an atom at the target site, including QSM, T2, or T2* imaging as described above.

In general, the MRI imaging can be performed with different field strength of the static magnet used in a variety of MRI equipment, including clinical and preclinical MRI. Imaging parameters, such as the repetition time, number of average, and to a large extend the echo time (TE) can be optimized based on the tissue type and the subject.

The method can further comprise subtracting the pre-collapse image from the image acquired after collapse to result in background-free contrast specific to the GVs.

In some embodiments, the collapsing ultrasound is applied at a collapsing ultrasound pressure greater than a selectable acoustic collapse pressure value. As used herein, the term "selectable acoustic collapse pressure" refers to an acoustic collapse pressure value that can be selected from the acoustic collapse profile of the GVPS type.

In some instances, the collapsing ultrasound is selected to have a collapsing pressure amplitude based on acoustic collapse pressure profiles of the GVPS type used in the contrast agent. In some instances, the collapsing ultrasound pressure can be referred to as the "peak positive pressure" of the ultrasound pulses. The term "peak positive pressure" refers to the maximum pressure amplitude of the positive pulse of a pressure wave, typically in terms of the difference between the peak pressure and the ambient pressure at the location in the person or specimen that is being imaged.

In some embodiments, the collapsing ultrasound transmit pulses are selected to have a peak positive pressure amplitude equal to or higher than an initial collapse pressure in the acoustic collapse profile of the GVPS used in the contrast agent administered to the target site.

In some embodiments, the collapsing ultrasound transmit pulses are selected to have a peak positive pressure amplitude equal to or higher than the midpoint collapse pressure in the acoustic collapse profile of the GVPS used in the contrast agent administered to the target site.

In some embodiments, the collapsing ultrasound transmit pulses are selected to have a peak positive pressure amplitude equal to or higher than a complete collapse pressure in the acoustic collapse profile of the GVPS used in the contrast agent administered to the target site.

In some embodiments, the collapsing ultrasound pressure used to collapse the GVPS type is higher than the midpoint of the hydrostatic collapse pressure profile of the GVPS type.

In some embodiments, the method further comprises obtaining the acoustic collapse pressure profile of the GVPS type administered to the target site. The acoustic collapse pressure profile of the GVPS type can be obtained by imaging GVPS, in vivo or in vitro, with imaging ultrasound energy after collapsing portions of the given GVPS type population with a collapsing ultrasound energy (e.g. ultrasound pulses) with increasing peak positive pressure amplitudes and constructing an acoustic pressure profile for the GVPS type. Alternatively, the acoustic collapse pressure profile can be obtained from the hydrostatic collapse pressure profile of the GVPS type according to equation (9).

In some embodiments, the GVPS type can be wild-type GVPS from any bacterial origin or variants thereof. For example, the GVPS type can be a wild-type Ana GV containing the wild-type GvpC having an acoustic collapse pressure profile defined by an initial collapse pressure of 650 kPa and a complete collapse pressure of 1,100 kPa. The collapsing ultrasound pulses can be acquired with a transmit pressure above 1,100 kPa.

In some embodiments, application of collapsing ultrasound to erase the contrast agent eliminates GV's susceptibility mismatch with water, allowing GV-specific contrast to be revealed by differential imaging and therefore creating an enhanced MRI contrast in the target site compared with an MRI imaging performed without collapse. In addition, such pressure can also be applied remotely using ultrasound, rendering the entire acoustomagnetic imaging paradigm non-invasive and depth-unlimited.

In an exemplary embodiment shown in Example 2, the mean collapse-dependent contrast in the GV-injected region was 19.4±3.2% compared to 0.3±2.0% when using a phosphate-buffered saline without GVs.

In some embodiments, an acoustically modulated multiplexed imaging method is described. The term "multiplex" refers to the presence of two or more GVPS types, each of which exhibits an acoustic collapse pressure profile substantially distinct from one another and/or a susceptibility substantially distinct one from the other. The two or more GVPSs can be derived from different bacteria or variants of GVPSs from the same or different bacteria.

In particular, in some embodiments, methods for acoustically modulated multiplexed imaging of a target site herein described comprise a MRI imaging method to be used in combination with ultrasound collapsing on a target site contrasted with a contrast agent comprising at least a first gas vesicle protein structure (GVPS) type and a second GVPS type is described. In the method, the first GVPS type exhibits a first acoustic collapse pressure profile and a first selectable acoustic collapse pressure value and the second GVPS type exhibits a second acoustic collapse pressure profile and a second selectable acoustic collapse pressure value. Each acoustic collapse pressure profile is defined as a collapse function from which a collapse account can be determined and a different selectable acoustic collapse pressure value can be selected from their corresponding acoustic collapse pressure profile.

The method comprises imaging the target site by applying an external magnetic field to the target site to obtain a first MRI image of the target site, selectively collapsing the first GVPS type by applying collapsing ultrasound to the target site, the collapsing ultrasound applied at a first acoustic collapse pressure value equal to or higher than the first selectable acoustic collapse pressure value and lower than the second selectable acoustic collapse pressure value.

The MRI imaging can be performed by susceptibility-based MRI imaging by measuring the relaxation rate of nuclear spins at the target site, including QSM, T2 or T2* map, or T2- or T2*-weighted imaging as described above, or the imaging can be performed by Hyper-CEST imaging.

The method further comprises imaging the target site containing at least the second, uncollapsed GVPS type by applying an external magnetic field to the target site to obtain a second MRI image of the target site.

In acoustically modulated multiplexed imaging methods herein described, the collapsing pressure of the collapsing ultrasound is selected based on the acoustic collapse pressure profiles of the GVPS types to selectively collapse one GVPS type over the other GVPS type.

The term "selectively collapse" refers to collapsing at least a portion of one GVPS type in a greater amount that any other GVPS type in a mixture containing a plurality of GVPS types. For any two given GVPS types each exhibiting an acoustic pressure profile characterized by f(p), the collapsing pressure is selected to have a f1(p) value for the first GVPS type greater than a f2(p) value for the second GVPS type in order to selectively collapse the first GVPS type.

In some embodiments, the collapsing pressure of the collapsing ultrasound is equal to a maximally informative collapse pressure ("MIAP") of two spectrally adjacent GV types.

The term "maximally informative collapse pressure" or "MIAP" as used herein indicates an acoustic pressure chosen based on the acoustic collapse profiles of the two GV types such that the fraction of the first GV collapsed at this pressure is maximally different from the fraction of the second GV collapsed at this pressure.

Accordingly, a maximally informative acoustic pressure (MIAP) value for a set GVPS relative to another one or more GVPS types in a GVPS mixture can be performed based on acoustic collapse profiles construed using detected acoustic collapse pressure values according to Equation (3). In particular, for GVPSs in a set GVPS mixture the MIAP can be expressed as a pressure by maximizing Δf(p), i.e.

$$\max[|f1(p)-f2(p)|], \text{ wherein } f1(p)=(1+e^{(p-pc)/\Delta p})^{-1} \text{ and } f2(p)=(1+e^{(p-pc)/\Delta p})^{-1} \quad \text{(Eq. 12)}$$

f1(p) and f2(p) correspond to the acoustic collapse profiles of the first GVPS and the second GVPS respectively.

The target site is then imagined following the collapsing by applying an external magnetic field to obtain a second MRI image of the target site.

In some embodiments, the acoustically modulated multiplexed imaging method further comprises after imaging the target site containing the second, uncollapsed GVPS type with MRI, collapsing the second GVPS type by applying a second collapsing ultrasound and imaging the target site containing the collapsed GVPS types with MRI. The second collapsing pressure is higher than the first collapsing pressure. In some embodiments, the second collapsing pressure is higher than the complete collapse pressure of the second GVPS type.

For example, in a contrast agent including Ana GVs with wild-type GvpC (first GVPS type) and Ana GVs with ΔGvpC (second GVPS type), a first collapsing pressure can be applied at 650 kPa and the second collapsing pressure can be applied at any pressure that is higher than 1230 kPa. During in vivo application, the skilled person should judge the tissue attenuation, which may complicate the actual pressure delivered to the target site (see Example 3).

In some embodiments, the acoustically modulated multiplexed imaging method further comprises obtaining an acoustic pressure profile of each GVPS type administered to the target site. The acoustic collapse pressure profile of each GVPS type can be obtained by imaging the GVPS, in vivo or in vitro, with imaging ultrasound energy after collapsing portions of the given GVPS type population with a collapsing ultrasound energy (e.g. ultrasound pulses) with increasing peak positive pressure amplitudes and constructing an acoustic collapse pressure profile for the GVPS type. Alternatively, the acoustic collapse pressure profile can be obtained from a hydrostatic collapse pressure profile of the GVPS type according to equation (10).

In some embodiments, the acoustically modulated multiplexed imaging method further comprises obtaining a first acoustic collapse pressure profile of a first GV and at least a second acoustic collapse pressure profile of at least a second GV, and calculating a first maximally informative collapse pressure from the obtained first and second acoustic collapse pressure profiles. Each acoustic collapse pressure profile is characterized by a fitted sigmoid function f(p) as would be understood by a skilled person upon review of the present disclosure.

For example, in a contrast agent comprising GVPs variants ΔGvpC, ΔN&C and GvpC$_{WT}$, the first collapsing pressure is equal to the first maximal informative acoustic pressure of 630 kPa calculated based on the acoustic collapse profiles of ΔGvpC variant and ΔN&C variant. The first maximal informative acoustic pressure is capable of maximally collapsing the ΔGvpC variant while minimally collapsing the other two variants, (ΔN&C and GvpC$_{WT}$). The second collapsing pressure is equal to the second maximal informative acoustic pressure of 790 kPa calculated based on the acoustic collapse profiles of ΔN&C variant and GvpC$_{WT}$. The second maximal informative acoustic pressure is capable of maximally collapsing the ΔN&C variant while minimally collapsing the remaining variant, GvpC$_{WT}$. The third collapsing pressure is about 1230 kPa, higher than the complete collapse pressure of GvpC$_{WT}$ in order to collapse the remaining GvpC$_{WT}$ variant.

GVs from distinct genetic origins can have different shapes and sizes and therefore can be distinguished on the basis of their differential effects on susceptibility-related MRI parameters, such as susceptibility experimentally measured from QSM, T2* and T2. Herein as an example, T2 and QSM are chosen as two input parameters for duplexed imaging of two types of GVs. Differences in GV morphology result in different nanoscale magnetic field patterns for a given quantity of gas, which can in turn alter the efficiency of aqueous T2 relaxation. The magnetic susceptibility calculated from QSM reports a value primarily dependent on the total amount of air in the sample, independent of its nanoscale arrangement. Therefore, each type of GV has its own parametric fingerprint.

Accordingly, in some embodiments, a MRI multiplexing method to be used on a target site contrasted with at least a first and a second gas vesicle protein structure (GVPS) types are described. In the method, each GVPS type has three parameters, a QSM susceptibility (χ), a T2* molar relaxivity (r2*), and a T2 molar relaxivity (r2). For each GVPS type, ratios can be calculated between susceptibility and T2 or T2* relaxivity, or between T2 and T2* relaxivity, or between all three parameters. This ratio forms a "parameter fingerprint" that can be used to distinguish one GVPS type from another GVPS type. In embodiments described herein, a first ratio of the first GVPS calculated between two or three selected parameter values, χ and/or r2*and/or r2, is different from a corresponding (expressed in the same order) second ratio of the second GVPS calculated between the second GVPS parameter values for the same selected parameters (same fingerprint type). The accuracy for quantitatively distinguishing the two GVPS types in MRI scales inversely with the difference of the ratios between the two GVPS types.

In some embodiments, the first and second molar susceptibility of the two GVPS types are different due to the first and second GVPS types being different sizes.

The method comprises administering to the target site a contrast agent comprising the at least first and second GVPS types and imaging the target site by applying an external magnetic field to the target site to obtain a MRI image of the target site. In some embodiments, the produced image is obtained using quantitative susceptibility mapping (QSM).

In some embodiments, imaging the target site further comprises processing the MRI image using voxel-wise unmixing to obtain an unmixed MRI image. The term "voxel-wise unmixing" refers to a mathematical image processing method for obtaining magnetically unmixed images by subtracting each sub-population of signals from a sum of signal contributed by each sub-population present in any given voxel. The term "voxel" refers to a volume element representing a value on a regular grid in the three-dimensional space. Voxels are often used in the visualization and analysis of medical data as known to a person skilled in the art.

In some embodiments, voxel-wise unmixing of susceptibility and relaxation rate can be performed according to the following equation (for two parameters, in this example using susceptibility (χ, or here as a relative susceptibility compared to the surrounding bulk water, Δχ) and T2 relaxivity ($r_2$):

$$\begin{pmatrix} R_{2,obs} \\ \Delta\chi_{obs} \end{pmatrix} = \begin{pmatrix} r_{2,\alpha} & r_{2,\beta} \\ \Delta\chi_\alpha & \Delta\chi_\beta \end{pmatrix} \cdot \begin{pmatrix} c_\alpha \\ c_\beta \end{pmatrix} \qquad \text{(Eq. 13)}$$

where the concentrations of the two GV species, $c_\alpha$ and $c_\beta$, are the two unknowns. $r_{2,\alpha}$ and $r_{2,\beta}$ were the r2 relaxivity and $\Delta\chi_\alpha$ and $\Delta\chi_\beta$ are the relative susceptibility of the GVs and $R_{2,obs}$ and $\Delta\chi_{obs}$ are the observed (i.e. measured) T2 and QSM relaxivity and relative susceptibility, respectively. One skilled in the art would recognize that the equation can be modified to use different parameters, or more than two parameters.

By unmixing the parameters, the quantities of the two GV types in each sample, $c_\alpha$ and $c_\beta$, can be obtained.

The method can further comprise measuring the first and second GV susceptibility and the first and second relaxivities before the administering. The susceptibility of the GVPS can be a molar susceptibility or a mass susceptibility. In particular, in some embodiments where GVPS is used as genetically encoded agent and is expected to be expressed in situ, mass susceptibility parameters are selected because the quantity of GVPS produced by the cells will be more affected by the mass quantity of the GVPS protein than molar concentration. In some embodiments where GVPS with a targeting moiety is made ex vivo and subsequently administered to the patient or animal, molar susceptibility parameters are selected because the quantity of GVPS at the target site is likely dependent on the concentration of the targeting moiety, which scales with the molar concentration of GVPS.

In some embodiments, the produced image is obtained by performing quantitative susceptibility mapping (QSM). The amount of contrast provided by QSM compared to T2/T2* depends on the geometric properties (size and shape) of the GVPS type. In some GVPS types, QSM shows stronger contrast than T2/T2*; in others, T2/T2*; shows stronger contrast than QSM. In some embodiments, GVPS types with larger volumes will give strong QSM contrast and GVPS types with greater length:width ratios will give strong T2/T2* contrast (see, e.g., Example 1 and in particular FIG. 4 panel a, showing QSM contrast in black and T2/T2* contrast in grey).

In some embodiments, the multiplexing method can be used to simultaneously track two or more types of cells expressing two different types of gas vesicles. The multiplexing method can also be used to track cells with one type of gas vesicle while with another type of gas vesicles to dynamically report a specific biological process, such as expression of a specific gene.

In some embodiments, susceptibility-based MRI imaging can be used in combination with ultrasound imaging and xenon-based MRI imaging of a target site contrast with a gas vesicle protein structure (GVPS). In such cases, the GVPS-containing contrast agent can be used as a trimodal contrast agent compatible with all three types of imaging modalities.

In the method, the GVPS type has an associated susceptibility and relaxivity property distinct from water and a selectable acoustic collapse pressure value derived from an acoustic collapse pressure profile of the GVPS type. The method comprises administering to a target site a contrast agent comprising a gas vesicle protein structure (GVPS) herein described, imaging the target site by applying an external magnetic field to the target site to obtain a MRI image of the target site, and imaging the target site by applying imaging ultrasound to the target site to obtain an ultrasound image of the target site.

An enhanced image can be created from the MRI image and the ultrasound image. As an example, the MRI image and ultrasound image can be combined such that the features in common between the two images are retained. Since GVPS will appear in both MRI and ultrasound images while noise and other artifacts specific to either MRI or ultrasound will be removed.

The imaging ultrasound is typically a low-pressure ultrasound, applied at an imaging ultrasound pressure lower than a selectable acoustic collapse pressure value. The selectable acoustic collapse pressure value is selected from the acoustic collapsing profile of the GVPS in the contrast agent.

In some embodiments, the imaging ultrasound transmit pulses are selected to have an imaging ultrasound pressure equal to or lower than an initial collapse pressure in the acoustic collapse profile of the GVPS used in the contrast agent administered to the target site.

In some embodiments, the imaging ultrasound transmit pulses are selected to an imaging ultrasound pressure equal to or lower than a midpoint collapse pressure in the acoustic collapse profile of the GVPS used in the contrast agent administered to the target site.

In some embodiments, the imaging ultrasound transmit pulses are selected to have an imaging ultrasound pressure equal to or lower than a complete collapse pressure in the acoustic collapse profile of the GVPS used in the contrast agent administered to the target site.

In some embodiments, the target site can be treated with collapsing ultrasound to collapse the GVPS in the contrast agent prior to or after the imaging ultrasound.

In addition to contrast agents reporting their location, GVs can also be used as dynamic sensors for imaging specific biological activities such as neurotransmission or enzymatic function. In response to molecular signals of interests, GVs can be designed to aggregate or form clusters, thus leading to an increase or decrease in T2 or T2* contrast. Differential MRI contrast based on clustering can then be produced.

Accordingly, in some embodiments, a method to perform MRI imaging of a biochemical event in a target site contrasted with a gas vesicle protein structure (GVPS) type is described. In the method, the GVPS type presents a functional group or binding moiety able to attach directly or indirectly to a corresponding functional group or binding moiety on the same or other GVPS type upon occurrence of the biochemical event. The method comprises imaging the target site by applying an external magnetic field to the target site to obtain a sequence of MRI images of the target site and detecting an increase or decrease in MRI contrast.

In particular, the GVPS can include a specific binding moiety attached to a surface of the gas vesicles. The specific binding moiety can be configured to specifically bind to a corresponding binding moiety on the same or other GVPS type or to a target site in a subject. The bonds formed between gas vesicles or between gas vesicles and the target site can include covalent bonds and non-covalent interactions, such as ionic bonds, hydrophobic interactions, hydrogen bonds, van der Walls forces, dipole-dipole interactions and others known to a person skilled in the art. In certain embodiments, the specific binding moiety can be covalently bound to the gas vesicles. Covalent bonds between the binding moiety and the gas vesicles can include covalent bonds that involve reactive groups such as N-hydroxysuccinimide (NHS) esters (such as sulfa-NHS esters), imidoesters, aryl azides, diazirines, carbodiimides, maleimides, cyanates, iodoacetamides, and others identifiable to the skilled person.

In some embodiments, a tag comprises a moiety that can be used for targeting a GV to a cell, such as a receptor-targeting peptide RGD, which binds effectively to a wide range of integrins. In some embodiments, a tag comprises a functionalized moiety that can be used to increase or decrease uptake of GVs by macrophages, such as a CD47 or an R8, respectively. In some embodiments, a tag can comprise a functionalized moiety that can be used for modular approaches in which the GV surface can be specifically covalently conjugated to other recombinant proteins, such as a SpyTag-SpyCatcher.

The functional group or binding moiety used herein can be any molecular that specifically binds to the corresponding functional group or binding moiety on another GVPS of the same or different type. In other embodiments, the functional group or binding moiety used herein can be a molecular that specifically binds to a target site of interest, such as a protein, peptide, cell, tissue and others that are targeted in the subjects.

Depending on the nature of the target site and biological events to be detected, the specific binding moiety can be an antibody against an epitope of a peptidic analyte, or any recognition molecule, such as a member of a specific binding pair. For example, suitable specific binding pairs include a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a peptide aptamer binding pair; and others identifiable to a person skilled in the art.

In some embodiments, the affinity between one binding moiety and its corresponding moiety to which the binding moiety specifically binds can be characterized by a dissociation constant $K_d$. In some instances, $K_d$ has a value less than $10^{-3}$ mol/L, or less than $10^{-5}$. In some cases, $K_d$ of a pair of binding moiety can be on the order of about $10^{-14}$ mol/L. "Affinity" refers to the strength of binding, increased binding affinity being correlated with a lower $K_d$.

In certain embodiments, the functional group or binding moiety on the GVPS includes an antibody. An antibody as defined here can include fragments of antibodies which retain specific binding to antigen, including Fab, Fv, scFv, and Fd fragments, chimeric antibodies, humanized antibodies, single-chain antibodies, and fusion proteins comprising an antigen-binding portion of an antibody and a non-antibody protein, as will be understood by a person skilled in the art. The antibodies can also include Fab', Fv, F(ab')2, and or other antibody fragments that retain specific binding to antigen.

In certain embodiments, a gas vesicle bound with an antibody binding moiety can be configured to specifically bind to an analyte at a target site of interest in a subject. As such, specific binding of the gas vesicle-bound specific binding moiety to the analyte at the target site of interest can indirectly bind the gas vesicle to the target site of interest in the subject, thus leading to the aggregation or clustering of the gas vesicles at the target site.

Accordingly, binding of the gas vesicles to other gas vesicles and/or the target site can aggregate the gas vesicles to form a cluster and thus facilitate detection of an increase or decrease in the MRI contrast.

In some embodiments, the clustering of GVs results in an increase in R2* and/or R2 at least 2-fold compared to control samples with no clustering of GVs. In an example (FIG. 10E and FIG. 10F), the increase of R2* and R2 can be 15-fold and 5-fold, respectively.

In some embodiments, the de-aggregation of GVs results in a decrease in R2* and/or R2. For example, the GVs can be functionalized to disassociate upon a biological stimulus. In such cases, the GVs are pre-clustered ex vivo, with the crosslinking bridge designed to be cleavable or degradable either enzymatically or chemically. Enzymatic cleavage can be made highly specific, using the knowledge of the specific cleavage site of the particular enzyme of interest. When the pre-clustered GVs encounter the enzyme of interest, the GV cluster will disintegrate and MRI image will show a decrease in R2* and/or R2.

In some embodiments, an increase or decrease in R2* and R2 corresponds to an increase or decrease in the GV density and the overall size of the GV clusters. In general, the higher the GV density and/or the larger the overall size of the GV cluster, the higher the MRI contrast of the GVs.

As used herein, the density of GV can be characterized by the average GV to GV distance. The overall size of the GV clusters can be characterized by hydrodynamic radius. The term "hydrodynamic radius" used herein can be defined as:

$$\frac{1}{R_{hyd}} \stackrel{def}{=} \frac{1}{N^2}\left\langle \sum_{i \neq j} \frac{1}{r_{ij}} \right\rangle \qquad (Eq.\ 14)$$

wherein $r_{ij}$ is the distance between two subparticles i and j, and the angular brackets represents an ensemble average over a collection of N subparticles. Hydrodynamic radius of a GV cluster can be mathematically calculated or measured using dynamic light scattering and others as will be understood by a person skilled in the art. The hydrodynamic radius of a cluster can be converted to radii of gyration using the Kirkwood-Riseman relationship (80-82) as will be understood by a person skilled in the art.

In some embodiments, the clustering of GVs results in a GV-GV distance of about 10 nm or less and the average hydrodynamic radius of about several microns.

Figure 11A:
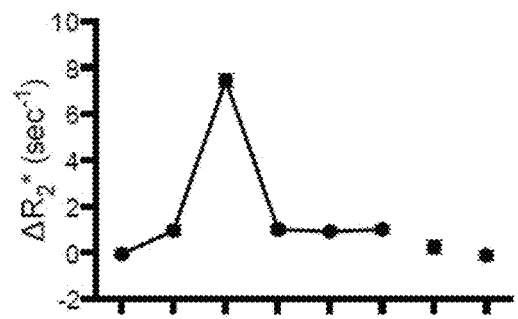
FIGS. 11A-E demonstrate, in some embodiments, the impact of streptavidin (SA) to gas vesicle (GV) stoichiometry on T2/T2* relaxation.
Figure 11B:
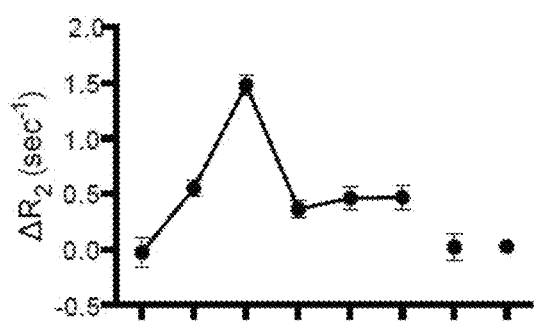
Figure 11C:
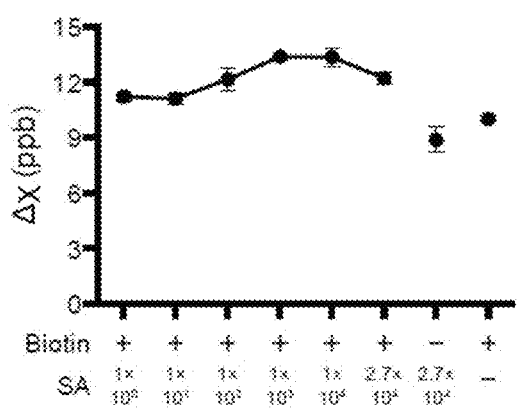
Figure 11D:
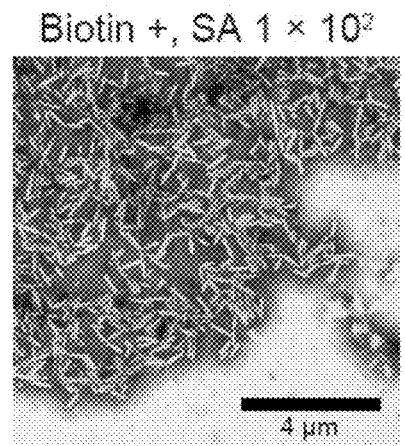
Figure 11E:
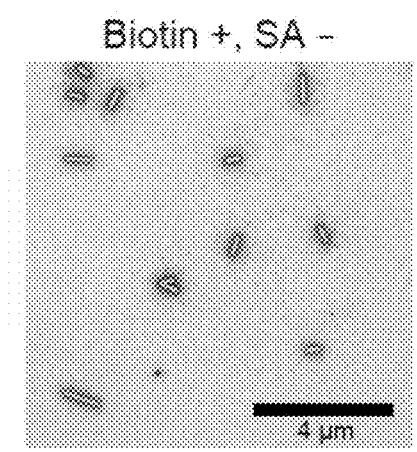

In an exemplary embodiment, the GVPS are Ana GVs attached with a biotin functional group. At the presence of appropriate streptavidin concentrations, GVs form microsize clusters (see Example 5). To select an optimal SA:GV ratio, a titration series of SA:GV ratio can be been performed (see, for example, FIGS. 11A-B), and the SA:GV value corresponding to the maximal $\Delta R_2$ and $\Delta R_2^*$ is the optimal ratio selected for clustering purpose. For example, the ratio of streptavidin to biotin-functionalized GV can be provided at about 100. Upon clustering, T2*- and T2-weighted images show dramatic relaxation enhancement compared to control samples with no clustering of GVs, with R2* and R2 increasing approximately 15- and 5-fold. In such case, the average hydrodynamic radius of GV cluster is about 2.7 microns.

In some embodiments, the obtained MRI images are $T_2$ or $T_2^*$ weighted images.

In some embodiments, the increase or decrease in MRI contrast is an increase or decrease in $R_2$ or $R_2^*$ relaxation rate.

Gas vesicles protein structures can be provided by Gyp genes endogenously expressed in bacteria or archea or heterologously expressed in cells that do not naturally produce gas vesicles. Endogenous expression refers to expression of Gyp proteins forming the protein shell of the GV in bacteria or archaea that naturally produce gas vesicles encoded (e.g. in their genome or native plasmid DNA). Heterologous expression refers to expression of Gyp proteins in any species that either does not naturally produce gas vesicles, or where its natural production of gas vesicles has been suppressed, for example through genetic knock-out of the genes encoding Gyp proteins, and where foreign DNA encoding gas vesicle genes is introduced into the organism to persist as a plasmid or integrate into the genome.

Plasmids or vectors can be constructed to comprise gas vesicle reporter gene clusters encoding a gas vesicle type. The term "Gas Vesicles Reporter Genes" or "GVRG" as described herein indicates a gene cluster encoding a set of Gyp proteins capable of providing a GV upon expression within a cell, for example, an *E. coli* bacterium. In the GVRG genetic circuit, molecular components are connected one to another in accordance to a circuit design by activating, inhibiting, binding or converting reactions to form a fully connected network of interacting components. An expression of the GV or an intracellular spatial translocation of GV type occurs when the GVRG genetic circuit operates according to the circuit design in response to the biochemical event. When cells comprising GVRG are introduced to a target site, in vivo or in vitro, the GV type can act as a reportable molecular component of a GVRG genetic circuit. Detailed description about the GVRG and its design can be found in the U.S. application Ser. No. 15/663,635, entitled "Genetically Engineered Gas Vesicle Gene Clusters, Genetic Circuits, Vectors, Bacterial Cells, Compositions, Methods and Systems for Contrast-Enhanced Imaging" filed on Jul. 28, 2017, which is incorporated herein by reference in its entirety.

Accordingly, in some embodiments herein described, a method to label a prokaryotic cell such as a bacterial or archaeal cell at a target site is described. The method comprises introducing into the prokaryotic cell a GVRG encoding a gas vesicle type, and imaging the target site comprising the prokaryotic cell to obtain a MRI image. The MRI imaging can be performed by susceptibility-based MRI imaging or by measuring the relaxation rate of nuclear spins at the target site, including QSM, T2 or T2* map, or T2- or T2*-weighted as described above.

In these embodiments, the genetic circuit encoding a GV can be designed to report a biochemical event by initiating expression of the GV, or to report a biochemical event by intracellular spatial translocation of a GV type already present in the cell, such as translocation of GVs to a specific sub-cellular compartment in response to a cellular signal or clustering of GVs.

Additional description of genetic circuits comprising GV and/or related gene clusters as a reportable molecular component and related configurations can be found in U.S. application Ser. No. 15/663,635, entitled "Genetically Engineered Gas Vesicle Gene Clusters, Genetic Circuits, Vectors, Bacterial Cells, Compositions, Methods and Systems for Contrast-Enhanced Imaging" filed on Jul. 28, 2017 incorporated herein by reference in its entirety.

In some embodiments, genetic circuit can be configured and introduced in one or more prokaryotic hosts to image one or more biochemical event and/or to label one or more prokaryotic hosts with approaches also described for a specific type of GV gene clusters (hybrid GV gene clusters) in U.S. application Ser. No. 15/663,635, entitled "Genetically Engineered Gas Vesicle Gene Clusters, Genetic Circuits, Vectors, Bacterial Cells, Compositions, Methods and Systems for Contrast-Enhanced Imaging" filed on Jul. 28, 2017 incorporated herein by reference in its entirety.

In some embodiments herein described, a genetic circuit having a reportable GV gene cluster can be used to image a biochemical event within a prokaryotic host and/or to label the prokaryotic host in combination with MRI and/or ultrasound methods herein described. In particular, in embodiments herein described the imaging can be performed following production of GVs performed intracellularly using any type of GV gene clusters comprised in gas vesicle reporting genetic circuits.

In some embodiments, a method can be performed to image with MRI and/or ultrasound methods herein described a biochemical event and/or a labeled prokaryotic host. In those embodiments, the method comprises:

introducing into the prokaryotic host a gas vesicle gene cluster (GVGC) configured for expression in the prokaryotic host, the gas vesicle gene cluster (GVGC) encoding a gas vesicle (GV) type, wherein the GV type is a reportable molecular component of a gas vesicle reporting (GVR) genetic circuit, in which molecular components are connected one to another in accordance to a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to the biochemical event and/or a trigger molecular component within the target prokaryotic host; and imaging the target site comprising the prokaryotic host by any of the method to perform MRI and/or ultrasound imaging of the target site herein described.

In some embodiments, a method can be performed to provide a multiplexed image with MRI and/or ultrasound methods herein described two or more biochemical events and/or a labeled prokaryotic hosts. In those embodiments the method comprises:

introducing into the one or more prokaryotic cell types a plurality of gas vesicle reporter genes (GVGCs) encoding a plurality of gas vesicle (GV) types, the plurality of GVGCs introduced to provide a plurality of reportable genetic molecular components of one or more GVR genetic circuits, in which molecular components are connected one to another in accordance to a circuit design by activating, inhibiting, binding or converting reactions to form a fully connected network of interacting components, wherein in each reportable genetic molecular component the gas vesicle (GV) type is expressed from the plurality of GVGCs when the one or more GVR genetic circuits operate according to the circuit design in response to a same or different biochemical events and/or to a same or different triggering molecular component, wherein each GV type exhibits i) an acoustic collapse pressure profile defined as a collapse function from which a collapse amount can be determined, and ii) a selectable acoustic collapse pressure value, selectable acoustic collapse pressure values going from a lowest acoustic collapse pressure value to a highest acoustic collapse pressure value, imaging the target site of the one or more prokaryotic cell type by the method to perform multiplexed MRI imaging and/or ultrasound imaging herein described.

In some embodiments the method can further comprise:

selectively collapsing each GV type to a collapse amount higher than a collapse amount of each remaining GV type by applying collapsing ultrasound to the target site comprising the one or more prokaryotic cell types, the collapsing ultrasound applied at a pressure value equal to or higher than the selectable acoustic collapse pressure value of the GV type being collapsed and lower than an acoustic collapse pressure value of said each remaining GV type or types.

The method further comprises imaging the target site containing the remaining GV type or types by applying imaging ultrasound to the target site, the imaging ultrasound applied at a pressure value lower than a lowest acoustic collapse pressure value of said each remaining GV type or types and/or with MRI imaging method herein described. In those embodiments, the method can also comprises repeating the collapsing and the imaging until all GV types are collapsed, thus providing a sequence of visible images of the target site, the sequence being indicative of image-by-image decreasing remaining GV types.

Representative cells that can endogenously express GVs include Cyanobacterium *Anabaena flos-aquae* (Ana GVs) [1], the *Halobacterium Halobacterium salinarum* (Halo GVs) [9], and *Bacillus megaterium* (Mega GVs). In some exemplary embodiments, endogenous GV gene clusters comprise *A. flos-aquae* regulatory genes GvpF, GvpG, GvpK, GvpJ, GvpN, GvpV, GvpW, and structural gene GvpA and optionally GvpC from *A. flos-aquae*.

Representative cells that can heterologously express GVs include *E. coli* expressing a heterologous GV gene cluster from *Bacillus megaterium* (Mega). In some exemplary embodiments, heterologous GV gene clusters comprise *B. megaterium* regulatory genes GvpR, GvpN, GvpF, GvpG, GvpL, GvpS, GvpK, GvpJ, GvpT and GvpU and structural gene GvpB from *B. megaterium*.

As a person skilled in the art will understand, Gyp proteins expressed by bacteria or archea typically include two primary structural proteins, here also indicated as GvpA and GvpC, and several putative minor components and chaperones [22-24].

Reference is made once again to the illustration of FIG. 1 showing a schematic representation of the structure of a GV. In the illustration of FIG. 1 GvpA and GvpC are indicated as the two major structural constituents of GVs, with GvpA ribs (1) (gray) forming the primary GV shell and the outer scaffold protein GvpC (2) (black) conferring structural integrity. In particular, in the illustration of FIG. 1, the light gray elements represent the proteinaceous gas vesicle shell, comprising multiple copies of GvpA and other minor structural constituents. In the illustration of FIG. 1, the dark rectangles (2) bound to the surface of the gas vesicle shell represent GvpC, a protein that affects mechanical and acoustic properties of the gas vesicle.

In bacteria or archaea expressing GVs, the Gyp proteins forming a GV's protein shell are encoded by a cluster of 8 to 14 different genes depending on the host bacteria or archaea, as will be understood by a skilled person.

The term "gene cluster" as used herein means a group of two or more genes found within an organism's DNA that encode for two or more polypeptides or proteins, which collectively share a generalized function or are genetically regulated together to produce a cellular structure and are often located within a few thousand base pairs of each other. The size of gene clusters can vary significantly, from a few genes to several hundred genes [25]. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

In embodiments herein described, identification of a gene cluster encoding for Gyp proteins in a bacteria or archaea can be performed for example by isolating the GVs from the bacteria or archaea, isolating the protein for the protein shell of the GV and derive the related amino acidic sequence with methods and techniques identifiable by a skilled person. The sequence of the genes encoding for the Gyp proteins can then be identified by method and techniques identifiable by a skilled person. For example, gas vesicle gene clusters can also be identified by persons skilled in the art by performing gene sequencing or partial- or whole-genome sequencing of organisms using wet lab and in silico molecular biology techniques known to those skilled in the art. As understood by those skilled in the art, gas vesicle gene clusters can be located on the chromosomal DNA or native plasmid DNA of microorganisms. After performing DNA or cDNA isolation from a microorganism, the polynucleotide sequences or fragments thereof or PCR-amplified fragments thereof can be sequenced using DNA sequencing methods such as Sanger sequencing, DNASeq, RNASeq, whole genome sequencing, and other methods known in the art using commercially available DNA sequencing reagents and equipment, and then the DNA sequences analyzed using computer programs for DNA sequence analysis known to skilled persons.

Gas vesicle gene cluster genes [22-24] can also be identified in DNA sequence databases such as GenBank, EMBL, DNA Data Bank of Japan, and others. Gas vesicle gene cluster gene sequences in databases such as those above can be searched using tools such as NCBI Nucleotide BLAST and the like, for gas vesicle gene sequences and homologs thereof, using gene sequence query methods known to those skilled in the art.

Exemplary genes present in the gene cluster for haloarchael GVs (which have the largest number of different gyp genes) and their predicted function and features are illustrated in Example 26 of related U.S. application Ser. No. 15/613,104, filed on Jun. 2, 2017 which is incorporated herein by reference in its entirety.

Representative examples of endogenously expressed GVs are the gas vesicle protein structure produced by the Cyanobacterium *Anabaena flos-aquae* (Ana GVs) [15], and the *Halobacterium Halobacterium salinarum* (Halo GVs) [24]. In particular, Ana GVs are cone-tipped cylindrical structures with a diameter of approximately 140 nm and length of up to 2 and in particular 200-800 nm or longer, encoded by a cluster of nine different genes, including the two primary structural proteins, GvpA and GvpC, and several putative minor components and putative chaperones [26] as would be understood by a person skilled in the art. Halo GVs are typically spindle-like structures with a maximal diameter of approximately 250 nm and length of 250-600 nm, encoded by a cluster of fourteen different genes, including the two primary structural proteins, GvpA and GvpC, and several putative minor components and putative chaperones [26] as would be understood by a person skilled in the art.

In embodiments herein described Gas vesicles protein structures can be provided by Gyp genes heterologously expressed in prokaryotic cells such as bacteria or archaea. Heterologous expression refers to expression of Gyp proteins in any species that either does not naturally produce gas vesicles, or where its natural production of gas vesicles has been suppressed, for example through genetic knock-out of the genes encoding Gyp proteins, and where foreign DNA encoding gas vesicle genes is introduced into the organism to persist as a plasmid or integrate into the genome.

In some embodiments, heterologously expressed Gyp genes can comprise genes encoding for corresponding Gyp proteins which are naturally occurring or have sequences having at least 50% identity with naturally occurring Gyp proteins.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that a similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank and UniProt and others identifiable to those skilled in the art.

As understood by those skilled in the art, determination of percent identity between any two sequences can be accomplished using a mathematical algorithm. Non-limiting examples of such mathematical algorithms are the algorithm of Myers and Miller [27], the local homology algorithm of Smith et al. [28]; the homology alignment algorithm of Needleman and Wunsch [29]; the search-for-similarity-method of Pearson and Lipman [30]; the algorithm of Karlin and Altschul [31], modified as in Karlin and Altschul [32]. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA [30], and TFASTA in the Wisconsin Genetics Software Package, Version 8 (available from Genetics Computer Group (GCG), 575 Science Drive, Madison, Wis., USA). Alignments using these programs can be performed using the default parameters.

In some embodiments, heterologously expressed Gyp proteins to provide a GV type have independently at least 50% sequence identity, preferably at least 80%, more preferably at least 90%, most preferably at least 95% sequence identity compared to a reference sequence of corresponding Gyp protein using one of the alignment programs described using standard parameters.

In some exemplary embodiments, the wild-type or native GVs used herein can be produced by *Anabaena flos-aquae* (Ana GVs) with their primary GvpC protein encoded by SEQ ID NO:6 of U.S. application Ser. No. 15/613,104. Alternatively, the native GVs used herein can be derivatives of native GVs having one or more variations including insertions, deletions or replacement with at least 30% preferably at least 80% identity with respect to SEQ ID NO:6 of U.S. application Ser. No. 15/613,104 and an E-value of less than 0.00001. GvpC proteins from other microorganisms can also be used as a reference sequence including the sequences listed in Table 4 of U.S. application Ser. No. 15/613,104, filed on Jun. 2, 2017 which is incorporated herein by reference in its entirety.

Heterologous expression of GVs in bacteria or archaea that do not express GVs can be performed by cloning one or more polynucleotides encoding naturally occurring Gyp proteins or homologs thereof that are required for production of GVs (comprising gvpA, gvpC, and other proteins known to those skilled in the art and described herein) into one or more suitable expression plasmids or vectors, and expressing the heterologous GV proteins in the bacteria or archaea. Polynucleotides encoding GV protein genes can be cloned using commercially available reagents from vendors such as Qiagen, Invitrogen, Applied Biosystems, Promega, and others, following standard molecular biology methods known in the art, such as those described herein. As would be understood by those skilled in the art, polynucleotides encoding GV protein genes can be obtained from several different sources. For example, polynucleotides encoding GV proteins can be obtained by isolating genomic DNA or cDNA encoding GV proteins from microorganisms whose genomes encode GV proteins genes, and/or express GV proteins RNA. RNA can be isolated from a cell that expresses GV proteins genes, and cDNA produced by reverse transcription using standard techniques and commercial kits. Genomic DNA can be purified from the cell, and cDNA or genomic DNA encoding one or more GV proteins isolated, following methods known to those in the art. Alternatively, polynucleotides comprising one or more gas vesicle genes can be synthesized using oligonucleotide and polynucleotide synthetic methods known in the art. PCR-based amplification of one or more GV protein genes can be performed using appropriately designed primer pairs (e.g. using PrimerDesign or other programs known to those skilled in the art). PCR-based amplification can be followed by ligation (e.g. using T4 DNA ligase) of a polynucleotide encoding gas vesicle gene amplicon into an appropriate expression cassette in a plasmid suitable for propagation in bacteria or other cells, such as transformation-competent *E. coli* DH5alpha, followed by growth of transformed cell cultures, purification of the plasmid for confirmation of the cloned enzyme by DNA sequence analysis, among other methods known to those skilled in the art. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences that are compatible with the bacteria or archaea heterologously expressing the GV, as would be understood by a skilled person. Promoters can be constitutively active or inducible. Exemplary inducible expression systems comprise IPTG-inducible expression as described in the Examples.

In some embodiments, where one or more Gyp proteins are expressed heterologously to form GVs in microorganisms other that the native host, the related sequence can be optimized for expression in the heterologous host microorganism as will be understood by a skilled person.

In particular, in some embodiments described herein, wherein GV is produced heterologously production of a GV gvpc gene sequences can be codon-optimized for expression in one or more microorganism of choice such as *Escherichia coli*, according to methods identifiable by a skilled person. As would be understood by those skilled in the art, the term "codon optimization" as used herein refers to the introduction of synonymous mutations into codons of a protein-coding gene in order to improve protein expression in expression systems of a particular organism, such as *E. coli* in accordance with the codon usage bias of that organism. The term "codon usage bias" refers to differences in the frequency of occurrence of synonymous codons in coding DNA. The genetic codes of different organisms are often biased towards using one of the several codons that encode a same amino acid over others—thus using the one codon with, a greater frequency than expected by chance. Optimized codons in microorganisms, such as *Escherichia coli* or *Saccharomyces cerevisiae*, reflect the composition of their respective genomic tRNA pool. The use of optimized codons can help to achieve faster translation rates and high accuracy.

In the field of bioinformatics and computational biology, many statistical methods have been proposed and used to analyze codon usage bias. Methods such as the 'frequency of optimal codons' (Fop), the Relative Codon Adaptation (RCA) or the 'Codon Adaptation Index' (CAI) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes. There are many computer programs to implement the statistical analyses enumerated above, including CodonW, GCUA, INCA, and others identifiable by those skilled in the art. Several software packages are available online for codon optimization of gene sequences, including those offered by companies such as GenScript, EnCor Biotechnology, Integrated DNA Technologies, ThermoFisher Scientific, among others known those skilled in the art. Those packages can be used in providing Gyp proteins with codon ensuring optimized expression in various cell systems as will be understood by a skilled person.

A representative example of heterologous GVs is the *E. coli* expressing a heterologous GV gene cluster from *Bacillus megaterium* (Mega). Mega GVs are typically cone-tipped cylindrical structures with a diameter of approximately 73 nm and length of 100-600 nm, encoded by a cluster of eleven or fourteen different genes, including the primary structural protein, GvpA, and several putative minor components and putative chaperones [26, 33] as would be understood by a person skilled in the art.

In some embodiments, the GVs can be engineered to modulate their mechanical, acoustic, surface and targeting properties in order to achieve enhanced harmonic responses and multiplexed imaging to be better distinguished from background tissues. In particular in those embodiments, a GV can be engineered to provide a variant GvpC protein and corresponding variant GV type and/or to provide a variant GV type with a modified amount of native or engineered GvpC protein on the protein shell of the GV.

A GvpC protein is a hydrophilic protein encoded by a gene of the GV gene cluster, which includes repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a GvpC multiple repetitions of a same repeat is flanked by an N-terminal region and a C-terminal region. In a same GvpC, repetitions of a same repeat in the GvpC protein can have different lengths and different sequence identity one with respect to another.

Repeat regions within any given GvpC sequence 'X' from organism 'Y' can be identified by comparing the related sequence with the sequence of a known GvpC (herein e.g. reference GvpC sequence "Z"). In particular the comparing can be performed on by aligning sequence 'X' to the reference GvpC sequence 'Z' using a sequence alignment tools such as BLASTP or other sequence alignment tools identifiable by a skilled person at the date of filing of the application upon reading of the present disclosure. In particular, a reference sequence 'Z' is chosen from a host that is the closest phylogenetic relative of 'Y', from a list of *Anabaena flos-aquae, Halobacterium salinarum, Haloferax mediditerranei, Microchaetae diplosiphon* and *Nostoc* sp. The sequence alignment of 'X' and 'Z' (e.g. a BLASTP) is performed by performing a first alignment of sequence X and sequence Z to identify a beginning and an end of a repeat in 'X as well as a number of repetition of the identified repeat, in accordance with the known repeats in 'Z'. The first alignment results in at least one first aligned portion of X with respect to reference sequence Z. The aligning can also comprises performing a second alignment between the at least one first aligned portion of X identified following the first alignment and additional portions of X to identify at least one repeat 'R1' in X. Other repeats in 'X' (i.e. R2, R3, R4 . . . ) can subsequently be identified with respect to R1.

In performing alignment steps sequence are identified as repeat when the sequence shows at least 3 or more of the following characteristics:

1) There are no gaps or spacer amino acids between any two adjacent repetition of a repeat (see e.g. FIG. 16 and FIG. 26 of U.S. application Ser. No. 15/613,104 filed on Jun. 2, 2017)

2) Each repetition of a repeat has a sequence length between 18-45 amino acids, e.g. 33 amino acids seen for 100% of the repeats in *Anabaena flos-aquae, Microchaetae diplosiphon* and *Nostoc* sp. (e.g. FIG. 26 of U.S. application Ser. No. 15/613,104 filed on Jun. 2, 2017)

3) Upon alignment of all the repeats within a given GvpC sequence, there exists for every position in more than 50% of the total number of repeats, greater than 50% sequence similarity of the amino acid residues in each repeat (e.g. FIG. 26 of U.S. application Ser. No. 15/613,104 filed on Jun. 2, 2017)

4) Sub-sequences of at least 3 or more amino acids at the beginning or end of the that are conserved across 50% or more of the repeats in a given GvpC sequence, also referred to as "consensus sequences". Exemplary embodiments of such consensus sequences are QAQELLAF at the end of repeats in *Anabaena flos-aquae*, LHQF at the end of repeats in Microchaete diplosiphon, LSQF at the end of repeats in *Microcystis aeruginosa* and DAF at the beginning of repeats in *Halobacterium salinarum*. (e.g. FIGS. 16 and 26 of U.S. application Ser. No. 15/613,104 filed on Jun. 2, 2017).

5) The consensus sequence of all the repeats within a given GvpC sequence show greater than 60% percent identity to the consensus sequence of all the repeats within another GvpC from a different microbial host of the same phylogenetic order (e.g. FIG. 26, panels g-h of U.S. application Ser. No. 15/613,104 filed on Jun. 2, 2017).

In some exemplary embodiments, the repeat has at least 90% sequence identity with another repeat within the same GvpC sequence.

In a GvpC the N-terminal region comprises the amino acid residues upstream (towards the N-terminus) of the first repeated sequence of the GvpC's repeat, while the C-terminal region comprises the amino acid residues downstream (towards the C-terminus) of the last repeated sequence of the GvpC's repeat.

GvpC protein is typically rich in glutamine, alanine and glutamic acid residues, which account for >40% of the residues. In the exemplary *Anabaena flos-aquae*, GvpC comprises five highly conserved 33-amino acid repeats with predicted alpha-helical structure, and is believed to bind across GvpA ribs to provide structural reinforcement [15], which aligns with experimental data. In biochemical studies, removal of GvpC and truncations to its sequence were shown to result in a reduced threshold for Ana GV collapse under hydrostatic pressure. In addition, previous studies in other species have demonstrated that GvpC can tolerate fusions of bacterial and viral polypeptides.

GvpC sequences in different bacteria or archaea producing GVs typically have a greater than 15% sequence identity and are produced by genes found in the gas vesicle gene cluster.

In some embodiments, a GV can be engineered to tune the related acoustic properties. In particular the engineering can be performed by genetically engineering a GV having an acoustic collapse pressure $aP_0$ performed to obtain a variant GV with a critical collapse pressure $aP_1$ lower than the $aP_0$.

In particular, in some embodiments, a method to tune acoustic properties of a gas vesicle protein structure having a critical collapse pressure $aP_0$ comprises engineering the GV by replacing a GvpC protein of the GV's protein shell with: subsaturated concentrations of the GvpC protein and/or saturated or subsaturated concentrations of a genetically modified GvpC protein.

In some of those embodiments, the GvpC proteins of the native GVs are removed with methods and techniques identifiable to a skilled person. For example, the native GvpC proteins can be removed by treating the GVs with urea, as shown in Example 1 and FIG. 2, panel d, of U.S. application Ser. No. 15/613,104 filed on Jun. 2, 2017, which results in GVs with their outer GvpC layer stripped but leaves the GvpA-based shell intact.

In some embodiment of methods to tune the acoustic properties of a GV, a GvpC protein of a set type GV can be replaced by wild-GvpC or genetically modified GvpC variants in certain concentrations either sub-saturating or saturated, such that complete surface coverage of the gvpA shell and gas vesicle strengthening does not occur.

In particular, in some embodiments, adding molar excess of gvpC:gvpA than that found in native GVs prior to dialysis to produce GVs can increase $aP_t$ up to a threshold, above which the critical collapse pressure plateaus and does not increase any further (see FIG. 5, FIG. 6 and FIG. 17 of U.S. application Ser. No. 15/613,104 filed on Jun. 2, 2017). Such concentration is considered as a saturated concentration.

Conversely, in some embodiments, adding a lower molar ratio of gvpC:gvpA prior to dialysis to produce GVs can decrease $aP_1$.

In some embodiment of methods to tune the acoustic properties of a GV, the genetically modified GvpC protein of methods and systems can be modified by at least one of
   a) a deletion of the N-terminal region, C-terminal region or both
   b) a deletion of 3 or more repeats, in particular starting from the repeat adjacent to the C-terminus and moving towards the N-terminus
   c) a deletion of at least one repeat immediately after the N-terminus, and
   d) addition of amino acids such as functional tags
   e) substitution of a sub-sequence comprising at least nine amino acids within the GvpC sequence, wherein the substitution refers to replacement of amino acids in the original GvpC sequence with any other amino acid sequence, particularly with other amino acid sequence having sequence similarity lower than 50% with respect to the sub-sequence within the GvpC sequence,
to obtain a gas vesicle variant with a critical collapse pressure $aP_1$ lower than the $aP_0$.

In some embodiments, a deletion can comprise a deletion of up to all of the amino acids of an N-terminal region, one or more repeat regions, or a C-terminal region. In some embodiments, a deletion can comprise a deletion of part of one or more of an N-terminal region, a C-terminal region, or a repeat region. For example, a deletion can comprise part of region 2 and part of repeat region 3, as shown in the Examples (exemplary variant N-rep2to3-C). In some embodiments, a deletion can comprise a deletion of more than one repeat region.

In some embodiments, a deletion of a gvpC N-terminal region or a C-terminal region can produce a gvpC variant comprised in a GV having a lower $aP_1$ than a deletion of a gvpC repeat region.

In some embodiments, a deletion of a gvpC N-terminal deletion can produce a gvpC variant comprised in a GV having a lower $aP_1$ than a deletion of a gvpC C-terminal deletion.

In some embodiments, a deletion of both a gvpC N-terminal region and a gvpC C-terminal region can produce a gvpC variant comprised in a GV having a lower $aP_1$ than a deletion of a gvpC N-terminal region or a C-terminal region performed individually.

In some embodiments, a deletion of one or more repeats regions that are in a position further towards the gvpC N-terminus can produce a gvpC variant comprised in a GV having a lower $aP_1$ than a deletion of one or more repeats regions that are in a position further towards the gvpC C-terminus.

In some embodiments herein described, GV variants without GvpC proteins or with truncated or mutated GvpC proteins exhibit lower collapse pressure compared to the native GVs under both hydrostatic pressure and ultrasound (Example 2 of U.S. application Ser. No. 15/613,104 filed on Jun. 2, 2017).

For example, the native Ana GVs have a hydrostatic collapse pressure about 569.85 kPa, while the Ana GV variants free of GvpC proteins and the Ana GV variants with truncated GvpC proteins have a hydrostatic collapse pressure about 195.30 kPa and 374.30 kPa, respectively (see Table 5 of U.S. application Ser. No. 15/613,104 filed on Jun. 2, 2017). The native Ana GVs have an acoustic collapse pressure about 868.81 kPa, while the Ana GV variants free of GvpC proteins and the Ana GV variants with truncated GvpC proteins have a hydrostatic collapse pressure about 571.00 kPa and 657.04 kPa, respectively (see Table 7 of U.S. application Ser. No. 15/613,104 filed on Jun. 2, 2017).

In some embodiments, GV variants without GvpC proteins or with truncated or mutated GvpC proteins show harmonic signals several-fold higher than the native GVs both in vitro and in vivo.

As used herein, the term "harmonic signal" or "harmonic frequency" refers to a frequency in a periodic waveform that is an integer multiple of the frequency of the fundamental signal. In addition, this term encompasses sub-harmonic signals, which are signals with a frequency equal to an integral submultiple of the frequency of the fundamental signal. In ultrasound imaging, the transmitted pulse is typically centered around a fundamental frequency, and received signals may be processed to isolate signals centered around the fundamental frequency or one or more harmonic frequencies. In relation to the imaging of GVs, for those natural or modified GVs that are capable of producing harmonic scattering at a particular acoustic pressure, isolating received harmonic signals during imaging can improve the fraction of the image signal that is due to the GVs rather than background scattering and reflection. Exemplary GV variants showing show harmonic signals several fold higher than the native GVs comprise GV variants such as ΔGvpC, ΔN&C-term, ΔN-term, ΔC-term, SR1, SR3, ST-GvpC, GvpC-R8, GvpC-RGD, GvpC-LRP, GvpC-mCD7, SR10ERY1, SR3CERY1, ΔN&C-CERY1, WTCERY1, GvpC-ACPP, GvpC-hPRM, N-term-rep1to2-C-term, N-term-rep1to3-C-term, N-term-rep2to3-C-term and N-term-rep1to4-C-term. FIG. 9 of U.S. application Ser. No. 15/613,104 shows exemplary genetic engineering of GV surface properties, cellular targeting and multimodal imaging. As shown in FIG. 9 of U.S. application Ser. No. 15/613,104 filed on Jun. 2, 2017, gvpC genetic fusions can be used to engineer novel GV properties and functions. FIG. 10 of U.S. application Ser. No. 15/613,104 filed on Jun. 2, 2017 shows an exemplary Clustal Omega sequence alignment of exemplary genetically engineered GvpC proteins described herein.

The term "fundamental signal" or "fundamental wave" refers to the primary frequency of the transmitted ultrasound pulse. All GVs can backscatter ultrasound at the fundamental frequency, allowing their detection by ultrasound.

The term "non-linear signal" refers to a signal that does not obey superposition and scaling properties, with regards to the input. The term "linear signal" refers to a signal that does obey those properties. One example of non-linearity is the production of harmonic signals in response to ultrasound excitation at a certain fundamental frequency. Another example is a non-linear response to acoustic pressure. One embodiment of such a non-linearity is the acoustic collapse profile of GVs, in which there is a non-linear relationship between the applied pressure and the disappearance of subsequent ultrasound contrast from the GVs as they collapse. Another example of a non-linear signal that does not involve the destruction of GVs, is the increase in both fundamental and harmonic signals with increasing pressure of the transmitted imaging pulse, wherein certain GVs exhibit a super-linear relationship between these signals and the pulse pressure. [34]

In some embodiments, the engineered GvpC variants are obtained by further linking the native GvpC protein to one or more other proteins, polypeptides, or domains to form a recombinant fusion protein.

Recombinant fusion proteins can be created artificially using recombinant DNA technology identifiable by a person skilled in the art of molecular biology. In general, the methods for producing recombinant fusion proteins comprise removing the stop codon from a cDNA or genomic sequence coding for the native GvpC protein having a SEQ ID NO: 6 of U.S. application Ser. No. 15/613,104 or a derivative thereof, then appending the cDNA or genomic sequence of the second protein in frame through ligation or overlap extension PCR. Optionally, PCR primers can further encode a linker of one or more amino acids residues and/or a PCR primer-encoded protease cleavage site placed between two proteins, polypeptides, or domains or parts thereof. The resulting DNA sequence will then be expressed by a cell or other protein expression system as a single protein. A fusion protein can also comprise a linker of one or more amino acids residues, which can enable the proteins to fold independently and retain functions of the original separate proteins or polypeptides or domains or parts thereof. Linkers in protein or peptide fusions can be engineered with protease cleavage sites that can enable the separation of one or more proteins, polypeptides, domains or parts thereof from the rest of the fusion protein. Other methods for genetically engineering these recombinant fusion proteins include Site Directed Mutagenesis (e.g. using Q5 Site-Directed Mutagenesis Kit from NEB or the QuickChange Lightning Kit from Agilent), Gibson Assembly (e.g. using the NEB Hi-Fi DNA Assembly Kit), Error-prone PCR (e.g. Mutazyme from Agilent) and Golden-Gate assembly (e.g. using the NEB Golden Gate Assembly Mix).

In some embodiments, the gvpC proteins described herein can be synthesized using cell-based methods or cell-free methods known to those skilled in the art. Protein biosynthesis can be performed by translation of DNA polynucleotides encoding the protein. Thus, protein biosynthesis can be performed by providing cell-based or cell-free protein translation systems with DNA polynucleotides encoding the protein. Plasmids with genetically engineered gvpC constructs described herein can be transformed into competent cells, such as BL21(DE3) cells (Invitrogen, Carlsbad, Calif.) or Rosetta™(DE3)pLysS cells (Millipore Sigma, Temecula, Calif.) using electroporation, heat shock, and other methods known to those skilled in the art and expressed in culture. The gvpC proteins described herein can also be produced by liquid-phase or solid-phase chemical protein synthetic methods known to those skilled in the art [16].

In some embodiments, a gvpC variant can be produced by engineering a gvpC protein from any species that encodes a gvpC protein in its genome, or a synthetically designed gvpC protein. In some embodiments, a gvpC protein is a gvpC protein from *Anabaena flos-aquae, Halobacterium salinarum, Halobacterium mediterranei, Microchaete diplosiphon* or *Nostoc* sp., or homologs thereof, and others identifiable by a skilled person.

In some embodiments of methods and systems and related compositions herein described one or more GVs (including variants GVs) can be engineered to include tags peptides and/or functional group to provide the GV with additional functionalities. In particular in some embodiments GVs can be functionalized through genetic and/or chemical modification of a Gyp protein (including variants GvpC protein herein described).

In particular, some embodiments here described tags and/or functional groups can be added through chemical or genetic modification of a GvpC protein or a variant thereof in accordance with the present disclosure of a set type of GV and/or through chemical modification of another Gyp protein of the set type GV.

Reference is made once again to FIG. 1 showing exemplary GvpC proteins engineered to include tags and/or functional groups. In particular, in the illustration of FIG. 1, the helical structure (3) connected to one of the GvpC proteins represents a genetically or chemically fused protein functionality that is not present in wild-type gas vesicles. The spherical bulb (4) connected to another GvpC represents a genetically or chemically fused fluorescent molecule allowing the gas vesicle to be imaged with an optical imaging modality such as fluorescence imaging.

In some embodiments, functionalization of a Gyp protein can be performed by reacting one or more GVs with one or more compounds to allow attachment and presentation of a functional group on the protein shell of the one or more GVs.

The term "functional group" as used herein indicates specific groups of atoms within a molecular structure that are responsible for the characteristic chemical reactions of that structure. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, the first functional group and the second functional group can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

The term "present" as used herein with reference to a compound or functional group indicates attachment performed to maintain the chemical reactivity of the compound or functional group as attached. Accordingly, a functional group presented on a GV shell and/or a Gyp protein thereof, is able to perform under the appropriate conditions the one or more chemical reactions that chemically characterize the functional group.

In some embodiments, the functionalization of the GvpC can be performed by chemical conjugation to a GvpC protein shell of moieties such as lysine residues and/or amine-reactive crosslinkers such as sulfo-N-hydroxysuccinimide esters (Sulfo-NHS). Depending on the application, the desired extent of labeling can be tuned by varying the molar ratio of Sulfo-NHS to GVs and by changing the incubation time as will be understood by a skilled person. Additional, chemical moieties including polymers (e.g. polyethylene glycol), fluorophores and small molecules (e.g. biotin) which can be conjugated methods identifiable. Biotinylated GVs can subsequently react with streptavidin or avidinated antibodies [35]. Either dialysis or buoyancy purification can be used to separate the labeled GVs from excess reactants.

In some embodiments methods to functionalize GVs can be performed by genetically engineering a GvpC protein of the GV shell to include one or more protein tags.

The term "tag" as used herein means protein tags comprising peptide sequences introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag.

The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags comprise the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO:11)); Calmodulin-tag, a peptide that can be bound by the protein calmodulin (KRRWKKNFIAVSAANRFKKISSSGAL (SEQ ID NO:12)); polyglutamate tag, a peptide binding efficiently to anion-exchange resin such as Mono-Q (EEEEEE (SEQ ID NO:13)); E-tag, a peptide recognized by an antibody (GAPVPYPDPLEPR (SEQ ID NO:14)); FLAG-tag, a peptide recognized by an antibody (DYKDDDDK (SEQ ID NO:15)); HA-tag, a peptide from hemagglutinin recognized by an antibody (YPYDVPDYA (SEQ ID NO:16)); His-tag, typically 5-10 histidines that can be bound by a nickel or cobalt chelate (HHHHHH (SEQ ID NO:17)); Myc-tag, a peptide derived from c-myc recognized by an antibody (EQKLISEEDL (SEQ ID NO:18)); NE-tag, a novel 18-amino-acid synthetic peptide (TKENPRSNQEESYDD-NES (SEQ ID NO:19)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO:20)); SBP-tag, a peptide which binds to streptavidin (MDEKTTGWRGGHVVEGLAGELEQLRAR-LEHHPQGQREP (SEQ ID NO:21)); Softag 1, for mammalian expression (SLAELLNAGLGGS (SEQ ID NO:22)); Softag 3, for prokaryotic expression (TQDPSRVG (SEQ ID NO:23)); Strep-tag, a peptide which binds to streptavidin or the modified streptavidin called streptactin (Strep-tag II: WSHPQFEK (SEQ ID NO:24)); TC tag, a tetracysteine tag that is recognized by FlAsH and ReAsH biarsenical compounds (CCPGCC (SEQ ID NO:25)); V5 tag, a peptide recognized by an antibody (GKPIPNPLLGLDST (SEQ ID NO:26)); VSV-tag, a peptide recognized by an antibody (YTDIEMNRLGK (SEQ ID NO:27)); Xpress tag (DLYDD-DDK (SEQ ID NO:28)); Covalent peptide tags such as: Isopeptag, a peptide which binds covalently to pilin-C protein (TDKDMTITFTNKKDAE (SEQ ID NO:29)); Spy-Tag, a peptide which binds covalently to SpyCatcher protein (AHIVMVDAYKPTK (SEQ ID NO:30)); SnoopTag, a peptide which binds covalently to SnoopCatcher protein (KLGDIEFIKVNK (SEQ ID NO:31)). In embodiments described herein, any of the tags of SEQ ID NO:11-31, and other tags known to those skilled in the art, can comprise one or more amino acid substitutions, insertions, or deletions that do not alter the function of the tag, and can further comprise one or more additional amino acids, up to a maximum tag length of 100 amino acids In some embodiments, the protein tag can be a polyhistidine tag. A polyhistidine-tag is an amino acid motif in proteins that typically consists of six histidine (His) residues typically, often at the N- or C-terminus of the protein. It is also known as hexa histidine-tag, 6×His-tag, His6 tag and by the trademarked name His-tag (registered by EMD Biosciences). The total number of histidine residues can vary in the tag. N- or C-terminal his-tags can also be followed or preceded, respectively, by a suitable amino acid sequence that facilitates a removal of the polyhistidine-tag using endopeptidases. This extra sequence is not necessary if exopeptidases are used to remove N-terminal His-tags (e.g., Qiagen TAGZyme). Polyhistidine-tagging can be used to detect protein-protein interactions in the same way as a pull-down assay. Fluorescent hexahistiadine CyDye tags are also available. These use Nickel covalent coordination to EDTA groups attached to fluorophores in order to create dyes that attach to the polyhistidine tag. This technique has been shown to be effective for following protein migration and trafficking. This technique may also be effective in order to measure distance via Fluorescent Resonance Energy Transfer.

In embodiments described herein a GvpC or a variant gvpC can be engineered to attach a tag fused to or inserted into an N-terminal region, a C-terminal region of a gvpC or a variant gvpC. In some embodiments, a tag that can be used for affinity purification of the engineered gvpC, such as a His-tag. In some embodiments, the tag comprises one or more functional groups that can be used to alter the surface charge of a GV, such as a lysine-rich protein (LRP). In some embodiments, a tag comprises a moiety that can be used for targeting a GV to a cell, such as a receptor-targeting peptide RGD, which binds effectively to a wide range of integrins. In some embodiments, a tag comprises a functionalized moiety that can be used to increase or decrease uptake of GVs by macrophages, such as a CD47 or an R8, respectively. In some embodiments, a tag can comprise a functionalized moiety that can be used for modular approaches in which the GV surface can be specifically covalently conjugated to other recombinant proteins, such as a SpyTag-SpyCatcher.

In some embodiments, engineering of a GvpC to attach one or more tags can be performed with or without substantially alter the critical collapse pressure of the base GvpC.

For example in some embodiments described herein, a GvpC protein of a GV can be engineered to attach one or more protein tags or polypeptide tags while optionally substantially altering the acoustic collapse pressure of a GV shell comprising the engineered GvpC as compared to a GV shell of a same non-engineered GvpC.

The term "substantially alter" or "substantially decrease" as used herein means a decrease of more than 10% in acoustic collapse pressure, preferably more than 20% in acoustic collapse pressure.

In some embodiments described herein, an engineered GvpC protein can comprise one or more protein tags or polypeptide tags. In embodiments described herein, appending functional residues comprising one or more polypeptide tags or protein tags to the N-terminus or the C-terminus of GvpCWT can reduce collapse pressure depending on the length and exact properties of the amino acid sequence.

In particular, in some embodiments, engineering of a GvpC can be further engineered to attach one or more tags up to the C-terminus without substantially alter the critical collapse pressure as compared to deleting the N- and/or C-terminal regions. In some embodiments, small tags such as RGD and RDG do not substantially alter the collapse pressure value. In some embodiments, tags comprising longer sequences such as LRP (100 residues) decrease acoustic collapse pressure to a greater extent. In some embodiments, tags such as those comprising mCD47 cause a substantial decrease in acoustic collapse pressure value. In some embodiments, appending a His-Tag (e.g. 6 His amino acids) to the N-terminus of the wild-type GvpC sequence does not substantially alter the acoustic collapse pressure value. In some embodiments, appending a gvpC with a Spytag-Spycatcher (FIG. 12 of U.S. application Ser. No. 15/613,104 filed on Jun. 2, 2017) is an effective method to functionalize GVs with large molecules (greater than 100 amino acids in length) such as fluorescent proteins, without substantially altering their collapse pressure value.

Addition of a functional moiety comprised in a tag to a gvpC or a variant gvpC can be obtained through different approaches identifiable by a skilled person.

For example, in some embodiments, an addition of a tag to a gvpC or variant gvpC can be performed at a protein level by first providing the gvpC protein or variant gvpC protein and the protein tag and then performing the insertion into a N-terminal or a C-terminal region by breaking a peptide bond between two adjacent amino acids of the gvpC or variant gvpC N-terminal region of C-terminal region and then forming new peptide bonds between the gvpC or variant gvpC and the protein tag, as described above. For example, the gvpC or variant gvpC can be digested with a protease to break a peptide bond between two adjacent amino acids in the gvpC or variant gvpC N-terminal region or C-terminal region, followed by insertion of the protein tag between the previously adjacent amino acids of the N-terminal region or C-terminal region, for example using native chemical ligation methods known to those skilled in the art [36]. In other embodiments, a protein tag can be fused to a C-terminus or an N-terminus of a gvPC protein or a variant gvpC protein using native chemical ligation methods known in the art.

In some embodiments, a tagged gvpC or variant gvpC functionalized with a protein tag inserted or fused to the N- or C-terminus can be synthesized as single protein by design. Proteins can be synthesized using biosynthetic methods, such as cell-based methods or cell-free methods known to those skilled in the art. Protein biosynthesis can be performed by translation of DNA or RNA polynucleotides encoding the protein. Thus, protein biosynthesis can be performed by providing cell-based or cell-free protein translation systems with DNA or RNA polynucleotides encoding the protein. For example, protein biosynthesis can be performed in cells transfected with in vitro transcribed RNA encoding the protein. Proteins can also be produced by liquid-phase or solid-phase chemical protein synthetic methods known to those skilled in the art [37].

In some embodiments, insertion or terminus fusion of a protein tag to a gvpC or a variant gvpC can be performed at a polynucleotide level through to an in-frame insertion of a protein tag-coding polynucleotide in between two codons in an N- or C-terminal region of a gvpC or a variant gvpC. An in-frame insertion can be performed in several steps, by first providing the gvpC- or variant gvpC-coding and the protein tag-coding polynucleotides and performing the insertion by breaking a bond (typically a phosphodiester bond) between two adjacent nucleotide bases of the first polynucleotide and then forming new bonds between the gvpC-coding polynucleotide and the protein tag-coding polynucleotide. For example, the gvpC coding polynucleotide can be digested with one or more restriction endonucleases and then the protein tag-coding polynucleotide inserted by ligation (e.g., using T7 DNA ligase) into compatible site(s) allowing formation of phosphodiester bonds between the first and second polynucleotide bases. Compatible DNA ligation sites can be "sticky" ends, digested with restriction endonuclease producing an overhang (e.g. EcoRI), or can be "blunt ends" with no overhang, as would be understood by those skilled in the art. A fusion of a polynucleotide encoding a tag can also be ligated to an N- or C-terminus of a gvpC or a variant gvpC polynucleotide by ligation (e.g., using T7 DNA ligase) into compatible site(s).

In some embodiments, the gvpC- or variant gvpC-coding and the protein tag-coding polynucleotides can be provided within a single polynucleotide by design. For example, a tag can be added by inserting the polynucleotide encoding a protein of interest in a plasmid or vector that has the tag ready to fuse at the N-terminus or C-terminus. The tag can be added using PCR primers encoding the tag; using PCR the tag can be fused to the N-terminus or C-terminus of the protein-coding polynucleotide, or can be inserted at an internal location, using internal epitope tagging [38], among other methods known to those skilled in the art. Other methods such as overlap extension PCR and infusion HD cloning can be used to insert a tag at a site between the N-terminus and C-terminus of a protein-coding polynucleotide (see Examples of U.S. application Ser. No. 15/613,104). Optionally, a polynucleotide encoding a 'linker' (such as a sequence encoding a short polypeptide or protein sequence, e.g., gly-gly-gly or gly-ser-gly can be placed between the protein of interest and the tag; this can be useful to prevent the tag from affecting the activity of the protein being tagged.

The choice of the location where a tag is added to a protein sequence depends mainly on the structural and functional features of a protein and the intended downstream methods employing the use of the tag.

In embodiments herein described, the insertion location of a protein tag in a genetically engineered gvpC or variant gvpC is performed at insertion position selected to have the tag presented on the external surface-exposed position of the gvpC or variant gvpC without compromising the function of the gvpC or variant gvpC.

In some embodiments, the GVPS and variants thereof can be used as a contrast agent in the method to provide an imaging of a target site. In some embodiments, the GVPS and variants thereof can be used as a contrast agent in the multiplexed and multi-modalities imaging methods herein described. In particular, a combination of GVPS and/or variants thereof can be used in a contrast agent, each exhibiting a different acoustic collapse profile with progressively decreased midpoint collapse pressure values. In some cases, the percentage difference between the midpoint collapse pressure values of any given two GVPN types in the contrast agent is at least twenty percent.

In some embodiments, one or more of the GVs herein described can be comprised in a composition together with a suitable vehicle. The term "vehicle" as used herein indicates any of various media acting usually as solvents, carriers, binders or diluents for the multi-ligand capture agents that are comprised in the composition as an active ingredient. In particular, the composition including the GVs can be used in one of the methods or systems herein described In some embodiments, one or more of the GVs herein described can be comprised in a contrast agent in the sense of the disclosure, the contrast agent comprising a plurality of the GVs (inclusive of engineered GVs) and/or GvpC variants herein described. The term "contrast agent" refers to an agent (material) in aqueous media, including water, saline, buffer, liquid media, configured to increase contrast in ultrasound imaging methods. By an increase in contrast, it is meant that the differences in image intensity between adjacent tissues visualized by a ultrasound imaging method are enhanced. For instance, differences in image intensity can be enhanced with the use one or more sets of imaging parameters.

The contrast agent can be provided in any pharmaceutically and/or physiologically suitable liquid or buffer known in the art. For example, the contrast agent can be contained in water, physiological saline, balanced salt solutions, buffers, aqueous dextrose, glycerol or the like. In certain embodiments, the contrast agent can be combined with agents that can stabilize and/or enhance delivery of the contrast agent to the target site. For example, the contrast agent can be administered with detergents, wetting agents, emulsifying agents, dispersing agents or preservatives.

In certain embodiments, two or more gas vesicle types are combined in a mixture for multiplexed imaging, wherein the two or more GV types have distinct acoustic collapse profiles and different biodistribution or targeting properties, such that their location in the imaged specimen provides information about two or more different aspects of the specimen, such that the unmixed ultrasound images acquired after administering this mixture contains information about the two or more different aspects of the specimen. Different aspects of the specimen may include different molecular or cellular targets to which the GVs bind, different vascularization patterns through which GVs flow in circulation, different levels of cellular metabolism leading to uptake or destruction of GVs, etc. These mixtures are supplied together with the acoustic collapse profiles or each component of the mixture and the MIAPs that should be used to acquire multiplexed images.

In certain embodiments, the gas vesicles contained in the contrast agent are bacterially-derived, gas vesicles formed by bacteria, such as photosynthetic bacteria (e.g., cyanobacteria), or archaea-derived gas vesicles formed by archaea (e.g., halobacteria). In other embodiments, the gas vesicles contained in the contrast agent are genetically engineered GVs by genetically engineering the bacterially-derived gas vesicles or archaea-derived gas vesicles herein described.

As mentioned above, the GVs (inclusive of native and variant GVs) and/or GvpC variants herein described can be provided as a part of systems to perform any of the above mentioned methods. The systems can be provided in the form of kits of parts. In a kit of parts, one or more GVs and/or GvpC variants and other reagents to perform the method are comprised in the kit independently. The GVs and/or GvpC variants can be included in one or more compositions, and each GV and/or GvpC variant is in a composition together with a suitable vehicle.

In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (such as. wash buffers and the like).

Further details concerning the engineered GVs, and systems and methods of the present disclosure will become more apparent hereinafter from the following detailed disclosure of examples by way of illustration only with reference to an experimental section.

EXAMPLES

The GVPS and related systems and methods herein disclosed are further illustrated in the following examples, which are provided by way of illustration and are not intended to be limiting.

In particular, the following examples illustrate exemplary methods and protocols for preparing exemplary gas vesicles protein structures from Ana, Halo and Mega and related characterizing, testing and use these GVPS for MRI imaging alone or in combination with ultrasound imaging in vivo and in vitro. A person skilled in the art will appreciate the applicability and the necessary modifications to adapt the features described in detail in the present section, to additional gas vesicle protein structure and related methods and systems according to embodiments of the present disclosure.

The following materials and methods were used in the experiments illustrated in the Examples.

Expression and Purification of Gas Vesicles.

Ana and Halo GVs were purified after expression in their respective host bacteria. *Anabaena flos-aquae* (CCAP strain 1403/13F) was cultured in Gorham's media supplemented with BG-11 solution (Sigma, St. Louis, Mo.) and 10 mM $NaHCO_3$ at 25° C., 100 rpm shaking and 1% $CO_2$ under a 14 h-light-10 h-dark cycle and confluency was reached in ~2 weeks. Halobacteria NRC-1 (Carolina Biological Supply, Burlington, N.C.) were cultured at 42° C. in ATCC medium 2185 under ambient light and with shaking at 100 rpm. Confluency was reached in ~1 week. Both types of cultures were transferred to sterile separating funnels. The buoyant cells were allowed to float to the top over a 48 h period. The subnatant was discarded and the floating cells were collected. *Anabaena* cells were lysed with 500 mM sorbitol and 10% Solulyse solution (Genlantis, San Diego, Calif.), and Halobacteria cells were hypertonically lysed with the addition of excess low-salt TMC buffer (10 mM Tris, pH=7.5, 2.5 mM $MgCl_2$, 2 mM $CaCl_2$). GVs were separated from cell debris by repeated centrifugally assisted floatation followed by resuspension in 1×PBS (Teknova, Hollister, Calif.). The centrifugation speed was carefully controlled to avoid the hydrostatic collapse of GVs. To prepare solution for in vivo experiments, purified GVs were dialyzed overnight in 1×PBS solution. The concentration of gas vesicles (GVs) was estimated based on the pressure-sensitive optical density at 500 nm ($OD_{500,PS}$) due to the ability of intact GVs to scatter light[39]. $Ana_{AC}$ was prepared by treating Ana GVs with a solution of 6 M urea and 20 mM Tris-HCl (pH=8.0). Two rounds of centrifugally assisted buoyancy purification were performed to remove GvpC. The solution was then dialyzed overnight in 1×PBS buffer to remove urea. GVs from *Bacillus megaterium* (Mega) were heterologously expressed in *E. coli* Rosetta™ 2 (DE3)pLysS (EMD Millipore, Billerica, Mass.). The pNL29 region of the Mega GV gene cluster[33] was cloned into the pST39 plasmid for expression under the control of the T7 promoter[40]. The transformed cells were grown at 30° C. in LB media supplemented with 0.2% glucose. 20 μM isopropyl β-D-1-thiogalactopyranoside (IPTG) was added at $OD_{600}$ between 0.4 and 0.6 to induce the expression of GVs, and the cells were grown overnight before harvesting by centrifugation. The clear subnatant was removed by a syringe, while both the floating and the pelleted cells were collected. The cells were lysed in 10% Solulyse (Genlantis, San Diego, Calif.), 250 μg/ml lysozyme and 10 μg/ml DNaseI. Centrifugally assisted floatation and $OD_{500}$ measurement followed the procedure used for Halo and Ana GV. Mega GVs, which are natively clustered after purification from bacteria, were unclustered using the same urea treatment, buoyancy purification and dialysis procedure described for the preparation of $Ana_{AC}$ GVs.

Transmission Electron Microscopy (TEM).

GVs at $OD_{500,PS}$~0.2 were prepared in a buffer of 10 mM HEPES, 150 mM NaCl (pH 8) and spotted on Formvar/Carbon 200 mesh grids (Ted Pella) that were rendered hydrophilic by glow discharging (Emitek K100X). GV samples were negatively stained using 2% uranyl acetate. Images were acquired using a Tecnai T12 LaB6 120 kV TEM.

Gas Vesicle Concentration Relationships.

Gas vesicle concentrations were determined using the relationships summarized in Table 1. The length and width of the GVs from TEM images was quantified in Fiji[41], and geometric calculations[42] were performed to derive the molecular weights of each type of GVs. The protein concentrations of purified GV solutions were measured by a Pierce 660 nm protein assay (Thermo Fisher Scientific, Waltham, Mass.) and related to $OD_{500,PS}$ for convenient quantification. In calculating molecular weight, Mega and Ana GVs were modeled as cylinders capped by cones at the two ends, while Halo GVs were modeled as spindles[43]. The GV wall thickness was assumed to be 1.80 nm for all three GV types[44], and the average protein density was assumed to be 1.4 $g/cm^3$ [45].

In Vitro MRI and Relaxometry.

Purified GVs or *E. coli* cells were embedded in agarose phantoms. 1% agarose stock solution was prepared in PBS and maintained at 60° C. until use. The size of the phantom was ~18×6×4 cm (length×width×height). Using a custom 3D-printed caster, the bottom half was first cast with cylindrical wells of the size 3×5 mm (diameter×depth) separated by 3 mm. The cylindrical geometry perpendicular to $B_0$ was chosen to ensure a homogeneous field in the sample wells to facilitate susceptibility-based imaging. The gel was allowed to solidify and exposed to air for 1 h for gas equilibration. Two-times concentrated GVs or *E. coli* cells in PBS were mixed 1:1 with the melted agarose stock solution and immediately loaded into the wells. Subsequently, the top half of the phantom was cast so that all the wells were surrounded by agarose. Care was taken to avoid bubbles. MRI was performed on a 7 T horizontal bore Bruker-Biospin scanner, using a 7.2 cm diameter volume coil for transmit and receive. T2* relaxivity was measured with 3D Multi Gradient Echo (MGE) experiments with the following parameters: repetition time (TR)=500 ms, 32 echos, echo spacing (TE)=9.0 ms, field of view (FOV)=12×6×0.8 $cm^3$, spatial resolution=0.25×0.25×0.25 $mm^3$ and 1 average. T2 relaxometry was performed by 2D Multi Slice Multi Echo (MSME) spin echo experiments with the following parameters: TR=2500 ms, 16 echos, TE=16.0 ms, FOV=8×6 $cm^2$, and spatial resolution=0.25×0.25 $mm^2$. Slice thickness=1 mm and 16 averages were used for multiparametric multiplexing experiments and 0.5 mm and 4 averages for all other experiments. T1 relaxometry was performed by 2D Rapid Acquisition with Relaxation Enhancement with Variable TR (RAREVTR) with the following parameters: Effective TE=9.683 ms, RARE factor=12, FOV=8×6 cm$^2$, spatial resolution=0.25×0.25 mm$^2$, slice thickness=0.5 mm, 2 average and 8 variable TR times including: 126.43, 738.40, 1461.21, 2344.09, 3478.70, 5068.54, 7746.55, 20000.00 ms. For data analysis, a circular region of interest (ROI) was drawn for each well using Fiji[41]. The average intensity of the ROI was imported into Matlab for exponential fitting to derive the T2*, T2 and T1 values. Voxel-wise T2* and T2 maps were generated by ImageJ plugin, MRI Processor, using Simplex fitting. For T2* relaxometry, the ROI excluded the rim of the wells. Multiparametric multiplexing of GVs was achieved by solving the matrix equation:

$$\begin{pmatrix} c_\alpha \\ c_\beta \end{pmatrix} = \begin{pmatrix} r_{2,\alpha} & r_{2,\beta} \\ \Delta\chi_\alpha & \Delta\chi_\beta \end{pmatrix}^{-1} \begin{pmatrix} R_{2,obs} \\ \Delta\chi_{obs} \end{pmatrix} \qquad \text{Eq. (15)}$$

where the concentrations of the two GV species, $c_\alpha$ and $c_\beta$, were the two unknowns. $r_{2,\alpha}$ and $r_{2,\beta}$ were the r2 relativity and $\Delta\chi_\alpha$ and $\Delta\chi_\beta$ were the molecular susceptibility of the GVs (Table 1).

TABLE 1

Summary of the geometrical, optical and magnetic properties of three types of gas vesicles (GVs).

|  | Mega | Ana | Halo |
|---|---|---|---|
| GV geometry | | | |
| Length (nm) | 249 ± 13 | 519 ± 15 | 400 ± 10 |
| Width (nm) | 72.5 ± 1.7 | 136.3 ± 2.0 | 250.8 ± 4.6 |
| Number of particles measured | N = 61 | N = 107 | N = 125 |
| GV concentration relationships | | | |
| Protein concentration to OD$_{500}$ ratio (μg/mL]/OD) | 145.5 ± 6.4 | 36.6 ± 2.6 | 13.4 ± 2.2 |
| Estimated molecular weight (MDa) | 71.7 | 320 | 282 |
| Molar protein concentration to OD$_{500}$ ratio (pM/OD) | 2,030 | 114 | 47.3 |
| GV MRI properties | | | |
| Molar susceptibility (ppb/nM) | 3.52 ± 0.27 | 18.53 ± 0.91 | 22.2 ± 1.1 |
| Mass susceptibility (ppb/[mg/mL]) | 39.2 ± 3.0 | 57.2 ± 2.8 | 80.9 ± 3.8 |
| Relaxivity r2* (sec$^{-1}$/nM) | 0.280 ± 0.027 | 1.19 ± 0.23 | 0.89 ± 0.11 |
| Relaxivity r2* (sec$^{-1}$/[mg/mL]) | 3.11 ± 0.30 | 3.66 ± 0.71 | 3.24 ± 0.42 |
| Relaxivity r2 (sec$^{-1}$/nM) | 0.138 ± 0.023 | 0.67 ± 0.11 | 0.273 ± 0.045 |
| Relaxivity r2 (sec$^{-1}$/[mg/mL]) | 1.53 ± 0.26 | 2.06 ± 0.34 | 1.00 ± 0.16 |

In Table 1, errors in GV length and width are in SEM. Although the size and shape of GVs are determined primarily by the genotype, each type possesses certain degree of heterogeneity. For example, Ana GVs has length distribution with a standard deviation of 35% of the mean[39]. The protein concentrations of GVs were measured by Pierce 660 nm protein assay. N=4, 5, 3 for Mega, Ana and Halo GVs, and the errors were SEM. Molar susceptibility and relaxivity were the slopes from linear regression fitting of the MRI measurements in FIG. 4, and the errors are the standard error of the slope.

Quantitative Susceptibility Mapping.

Magnitude and phase images of 3D MGE or 3D fast low angle shot (FLASH) experiments were obtained in ParaVision 5.1 (Bruker), and the images from a single echo served as the input to the Susceptibility Mapping and Phase artifacts Removal Toolbox (SMART) (MRI Institute for Biomedical Research, Detroit, Mich.). This software performed phase unwrapping using the 3D-SRNCP algorithm [46], background field removal by the SHARP algorithm [47] and susceptibility map generation using the SWIM algorithm [48]. The resulting QSM images were analyzed in Fiji[41]. Unless specified otherwise, all QSM images were processed from the 5$^{th}$ echo (TE=45.0 ms) of a 3D MGE experiment.

In Vitro Acoustic Collapse.

Acoustic GV collapse was performed separately from MRI for in vitro experiments. The acoustically modulated multiplexing experiments were performed with a single element immersion transducer (Olympus) with transmit frequency=2.25 MHz, element size=0.75 inch, focal length=1.5 inch, pulse duration=10 μs, duty cycle=0.1%. A waveform generator (Model WS8352, Tabor Electronics, Tel Hanan, Israel) and a power amplifier (Model 3100LA, Electronics & Innovation, Rochester, N.Y.) were used to drive the transducer. The input voltages to the transducer were 57 V and 131 V for collapsing Ana$_{AC}$ and Ana$_{WT}$ GVs in the agarose phantom, respectively. The output peak positive pressures were estimated by a fiber optic hydrophone (Precision Acoustics, Dorset, UK) to be 0.74 MPa and 1.41 MPa, respectively. Note that the difference between acoustic and hydrostatic collapse pressures of GVs were expected due to the inability of gas to exit GVs during acoustic collapse[49, 50]. For collapsing the intracellular GVs in *E. coli*, a Verasonics Vantage programmable ultrasound scanning system using the L11-4v 128-element linear array transducer (Verasonics, Kirkland, Mass.) was used with the following parameters: transmit frequency=6.25 MHz, transmit voltage=15 V.

In Vivo MRI and Acoustic Collapse.

All animal experiments were approved by the Institutional Animal Care and Use Committee (IACUC) of the California Institute of Technology. Male C57BL6J mice between 12 and 18 weeks of age (Jackson Laboratory, Bar Harbor, Me.) were anaesthetized with 1-2.5% isoflurane. 2 μL PBS buffer with or without 3.4 nM Ana$_{WT}$ GVs was injected into the striatum or the thalamus using a Nanofil blunt-end g35 needle coupled with a motorized pump (World Precision instruments, Sarasota, Fla.) at 100 nL/min using a stereotaxic frame (Kopf, Tujunga, Calif.). The coordinates of the two pairs of sites with respect to the bregma were: +1 mm anterior-posterior, ±2 mm medio-lateral, −3.25 to −3.5 mm dorso-ventral and −2.5 mm anterior-posterior, ±1.5 mm medio-lateral, −3.25 mm dorso-ventral. The needles remained in place after injection for 5 minutes to avoid backflow along the needle tract. $OD_{500,PS}$ of the GV solution inside the syringe was measured post-injection to confirm GV integrity. For MRI experiments, mice were anaesthetized using 1-2% isoflurane and were placed in an acrylic cradle where respiration and body temperature were continuously monitored using a pressure transducer (Biopac Systems) and fiber optic rectal thermometer (Neoptix). Warm air was circulated to maintain body temperature at 30° C. A 7.2 cm diameter volume coil was used for RF transmission and a 3 cm diameter surface coil was used for detection. T2*-weighted images were acquired by 2D FLASH experiments with the following parameters: TE=15.0 ms, TR=50.595 ms, flip angle=20°, FOV=4×2.8 cm$^2$, spatial resolution=0.1×0.1 mm$^2$, slice thickness=1.0 mm and 64 averages. 3D FLASH experiments with the same voxel size and total experimental time were also used, where 64 averages were replaced by 64 slices and 1 average. Anatomical images were acquired by 2D RARE experiments with the following parameters: effective TE=19.98 ms, RARE factor=8, TR=300 ms, FOV=14.0×51.2 cm$^2$, spatial resolution=0.1×0.1 mm$^2$, slice thickness=1.0 mm and 1 average. Data analysis was performed in Fiji[41]. An elliptical ROI was manually drawn for the hypointense region containing GVs. Another concentric ROI with twice the radius was drawn and the intensity of the region between the two ROI was used to measure the intensity of the background tissue. The intensity of the GV region normalized by the background was used to calculate the percentage contrast change upon ultrasound exposure. In situ collapse of GVs was achieved using an MRI-guided focused ultrasound system comprising a 16-channel signal generator, a motorized MRI-compatible transducer positioning system and an annular array transducer operating at 1.5 MHz (Image Guided Therapy, Pessac, France). Two ultrasound pulse schemes were used to transcranially collapse Ana GVs, with the following parameters: (1) pulse length (PL) =10 µs, duty cycle=0.01%, peak rarefactional pressure (PRP)=5.7 MPa, 10 to 200 shots; (2) PL=50 ms, duty cycle=5%, PRP=3.0 MPa, 100 to 600 shots. Both schemes were capable of collapsing GVs and were tested for both the GV and the control PBS injection sites. The peak positive pressures were derived from the maximal value recorded at the focal spot by a fiber optic hydrophone in water (Precision Acoustics, Dorset, UK) assuming 18% attenuation by the mouse skull [51].

Gas Vesicle Clustering.

Purified Ana GVs were biotinylated using a 10$^5$ molar excess of EZ-Link Sulfo-NHS-LC-biotin (Thermo Scientific, Rockford, Ill.) for 4 hours in PBS buffer. The excess biotin was removed by two rounds of overnight dialysis in PBS buffer. Biotinylated or control GVs at $OD_{500,PS}$=10 were incubated with streptavidin (Geno Technology, St. Louis, Mo.) at the ratio specific to each experiment for 30 minutes at room temperature before loading into MRI phantom. Dynamic light scattering measurements were performed using a Zeta-PALS instrument (Brookhaven Instruments, Hotsville, N.Y.) at a concentration equivalent to $OD_{500,PS}$=0.2 in PBS.

Finite Element Simulations.

The magnetic field simulation was performed in Finite Element Method Magnetics (FEMM) version 4.2 [52]. GVs were simulated as an axisymmetric object with its longitudinal axis aligned parallel to the magnetic field. The ratio of the susceptibility between inside and outside ($\chi_{in}/\chi_{out}$) of the GVs was taken to be 1+9.395×10$^{-6}$, which corresponds to the susceptibility difference between air and water. The cylindrical well in an agarose phantom was simulated as a circle in 2D planar domain. $\chi_{in}/\chi_{out}$ was set at 1+3.426×10$^{-8}$, which correlates to 0.36% air inside the well, the amount expected for 1 nM concentration of Ana GVs. The GV cluster was simulated as a single sphere in the axisymmetric domain occupying a volume equivalent of 200 GVs packed at 20% density. In all cases, the external field was set at 7.0 T to correlate to the experimental condition.

Example 1: Susceptibility-Based MRI Contrast Using GVs at Sub-Nanomolar Concentrations To test the ability of GVs to produce susceptibility-based MRI contrast, computational modelling and in vitro imaging experiments were performed.

Figure 2:
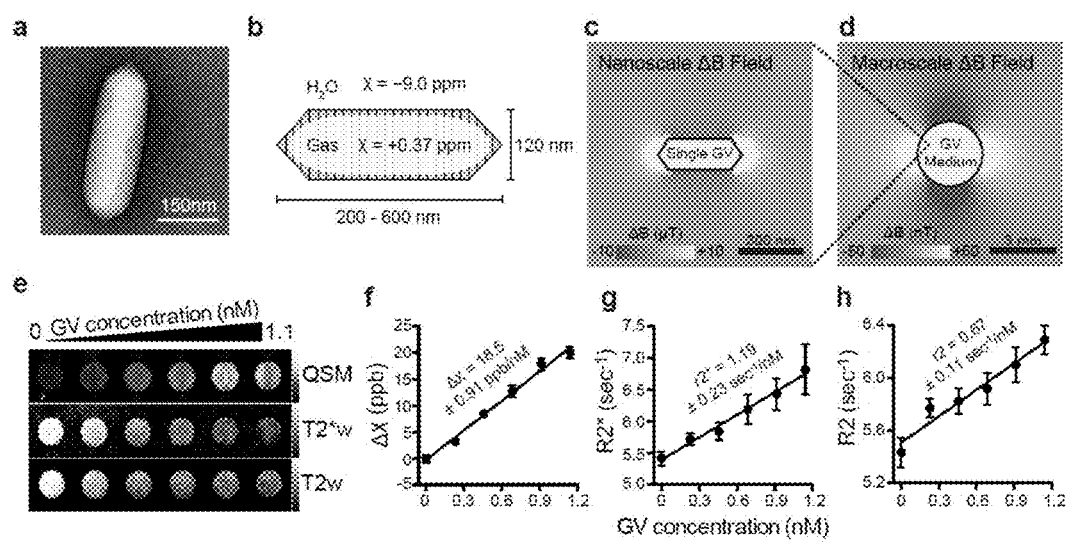
FIG. 2 shows in some embodiments susceptibility contrast produced by exemplary gas vesicles (GVs). Panel a, Transmission electron microscopy (TEM) image of a GV from *Anabaena flos-aquae* (Ana) Panel b. Schematic drawing of a GV, whose air-filled interior has magnetic susceptibility different from that of surrounding $H_2O$. Panel c, Finite element model of the magnetic field gradient produced by a single air-filled Ana GV in water exposed to a 7 Tesla horizontal magnetic field. Panel d, Finite element model of the magnetic field gradient produced by a cylindrical 0.5% agarose sample containing 1 nM Ana GVs embedded in an 1% agarose phantom. Panel e, Quantitative susceptibility map (QSM), T2*-weighted (T2*w) and T2-weighted (T2w) images of wells containing Ana GVs at concentrations ranging from 0 to 1.1 nM. The QSM scale ranges linearly from −2 to +50 parts per billion (ppb), and T2*w and T2w images at echo time (TE)=144 msec have linear scales adjusted for optimal contrast. Panels f, g, h, Magnetic susceptibility, T2* relaxation rate and T2 relaxation rate, respectively for different concentrations of Ana GVs. The value and the standard error of the slope from the linear regression fitting are shown for each plot and corresponds to molar susceptibility (Panel f), r2* relaxivity (Panel g) and r2 relaxivity (Panel h). N=9 in (Panels f, g) and N=6 in (Panel h). Error bars represent SEM.
Figure 3A:
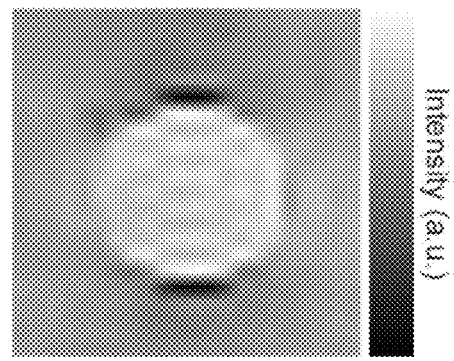
FIGS. 3A-D show exemplary images of GV-containing well in the agarose phantom.
Figure 3B:
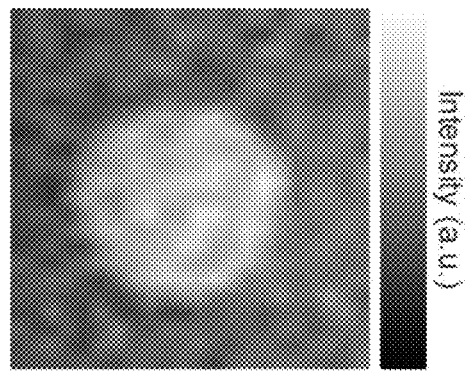
Figure 3C:
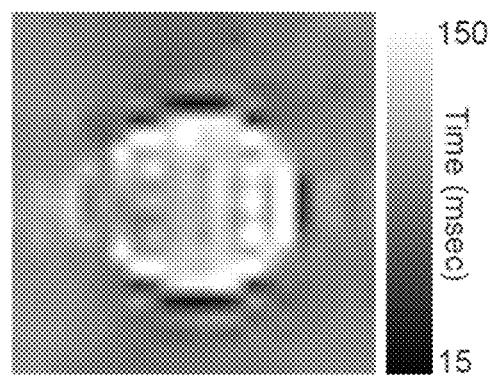
Figure 3D:
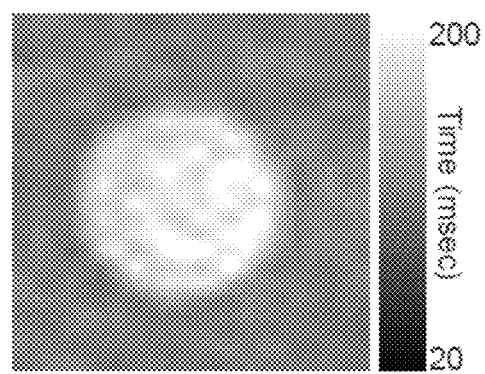

Exemplary measurement of the resulting imaging of Ana GV is shown in FIG. 2, panel f, in which magnetic susceptibility is measured for different concentrations of Ana GVs. The value of the slope from the linear regression fitting for the plot corresponds to molar susceptibility.

The air contents of the GV interior have an expected magnetic susceptibility of +0.37 ppm, differing significantly from water, which is diamagnetic at −9.0 ppm (FIG. 2 panel b). As a result of this mismatch, individual GVs in aqueous media under a uniform magnetic field are predicted by finite element modelling to produce nanoscale magnetic field gradients (FIG. 2 panel c). The proton nuclear spins on water molecules experiencing such gradients are expected to decohere, leading to enhanced T2/T2* relaxation and a concomitant reduction of local signal intensity in T2- and T2*-weighted images, which can be acquired with widely used spin-echo and gradient-echo MRI pulse sequences [53]. In addition, macroscale volumes containing GVs have a different average susceptibility than surrounding voxels, producing macroscale field gradients (FIG. 2 panel d), which should cause a patterned change of spin phase beyond the site of the GVs (FIGS. 3A-D). These phase changes can be decoded by quantitative susceptibility mapping (QSM) algorithms to produce contrast maps with additional sensitivity beyond magnitude-only T2/T2* images [54, 55].

To test the ability of GV nanostructures to produce these forms of contrast, GVs were purified from the cyanobacterium *Anabaena flos-aquae* (Ana GVs) and imaged them in agarose phantoms with a 7 Tesla MRI scanner. As predicted, GVs produced robust contrast in T2*- and T2-weighed images and QSM maps (FIG. 2 panel 3). Quantification of this MRI contrast revealed T2* and T2 relaxivities of 1.19±0.23 nM$^{-1}$ s$^{-1}$ and 0.67±0.11 nM$^{-1}$ s$^{-1}$, respectively, and molar susceptibility of 18.53±0.91 parts-per-billion (ppb) nM$^{-1}$ (FIG. 2 panels f-h). Notably, Ana GVs are readily detectable by QSM at concentrations below 300 pM, corresponding to a net protein concentration below 80 µg/mL, which is substantially lower than most existing protein-based MRI reporters[56-58]. At these concentrations, GVs produce negligible T1 contrast (FIG. 4), and have an insignificant effect on proton density due to water exclusion (<0.1% v/v), preserving these contrast modes for use by orthogonal reporters or anatomical imaging.

Example 2: Background-Free Acoustically Modulated Imaging

Figure 5A:
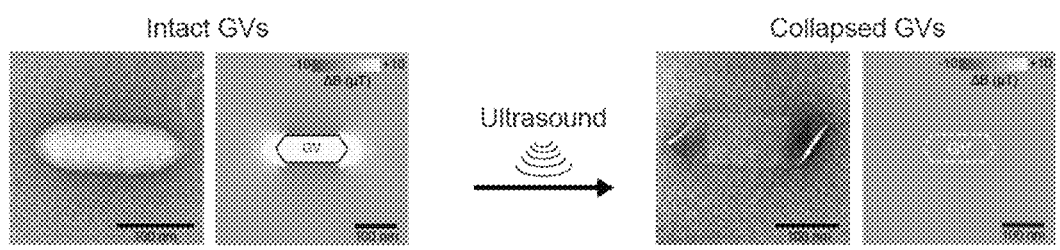
FIGS. 5A-C show an exemplary embodiment of background-free acoustically modulated imaging.

Experiments were performed test the specificity of GVs as contrast agent to be detected in biological tissues or other target site minimizing confused imaging due to the presence of background contrast from endogenous sources such as blood vessels and tissue interfaces In particular, QSM images of samples containing Ana GVs or buffer before and after acoustic collapse with ultrasound were acquired. The results are shown in FIGS. 5A-C.

Figure 5B:
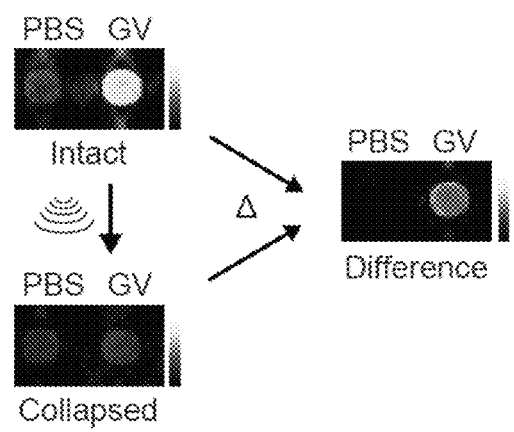
Figure 5C:
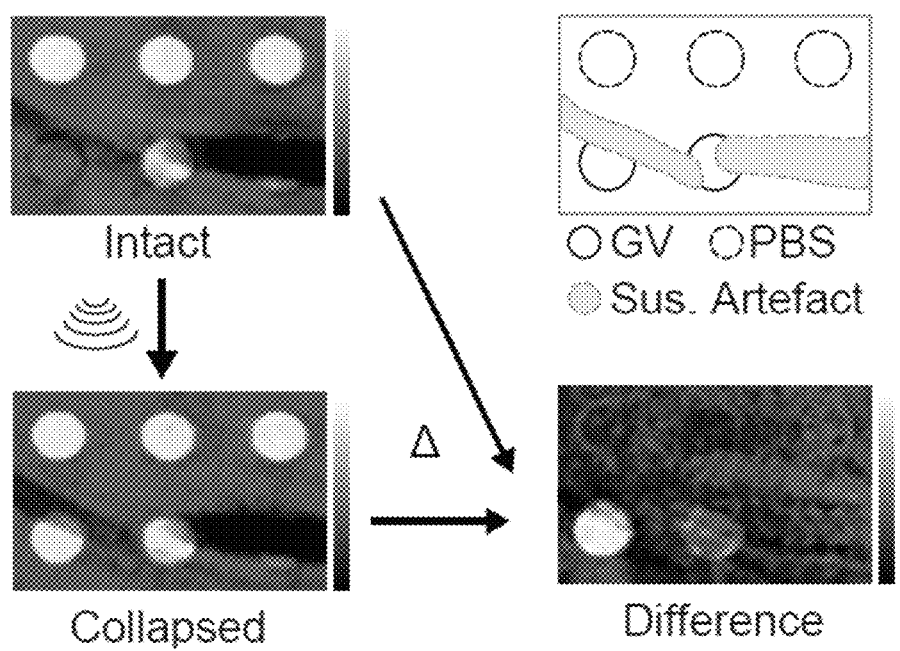

Subtraction of the pre-collapse image from the image acquired after collapse resulted in background-free contrast specific to the GVs (FIG. 5B). To demonstrate that this method can distinguish GVs from susceptibility artefacts in T2*-weighted imaging, a phantom containing GVs, regions was created with lower concentration of agarose and capillary tubes filled with paramagnetic nickel. While GVs are difficult to distinguish from other hyper- and hypo-intense regions in the raw initial image, acoustic collapse and background subtraction enable the specific observation of GVs even at concentrations that were initially difficult to spot by the naked eyes (FIG. 5B).

Accordingly, the experiments show that GVs have a built-in mechanism by which their identity as the source of any given MRI contrast can be ascertained. In particular, the collapse of their gaseous interior under pressure should eliminate GV's susceptibility mismatch with water (FIG. 5A), allowing GV-specific contrast to be revealed by differential imaging. Importantly, such pressure can be applied remotely using ultrasound, rendering the entire acoustically modulated imaging paradigm non-invasive and depth-unlimited.

Figure 6A:
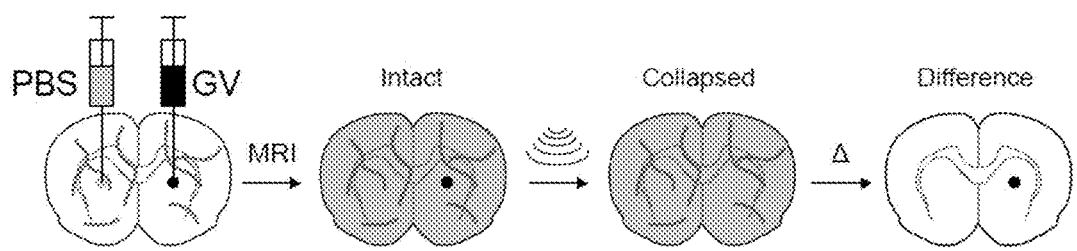
FIG. 6A shows diagram of the in vivo experiment in the living mouse brain. 2 μL solutions of 3.4 nM Ana GVs or blank PBS buffer were injected into contralateral striatum in the mouse brain. T2*-weighted images taken before the insonication were subtracted from those taken after, and the difference images were calculated to reveal contrast specific to the GVs, giving rise to a background-free image.
Figure 6B:
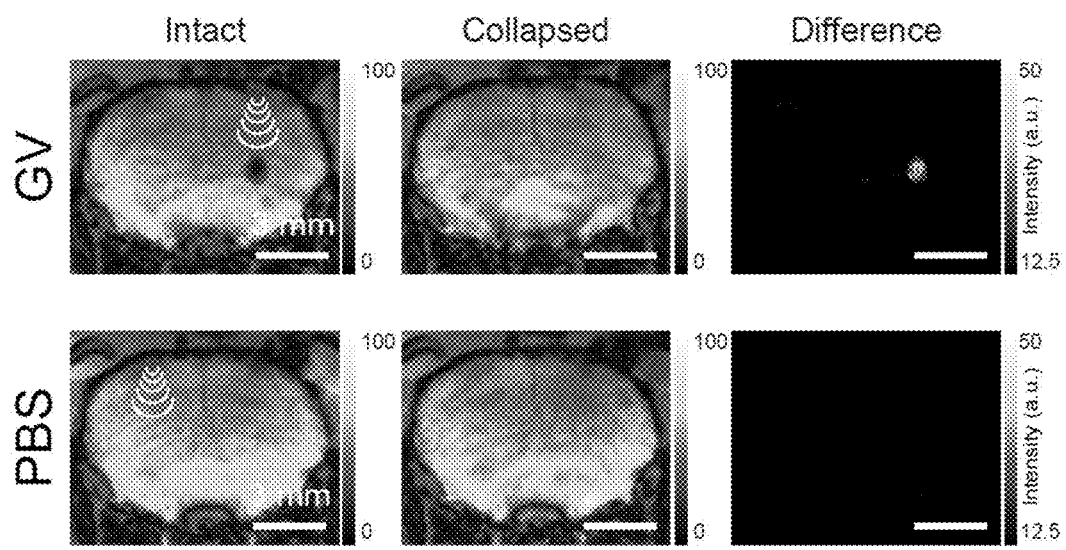
FIG. 6B shows representative T2*-weighted images (TE=15 msec) of a mouse injected with PBS and GVs, acquired before and after ultrasound was applied to the site of GV injection (top) and the site of PBS injection (bottom). Their subtraction results in the difference image.
Figure 6C:
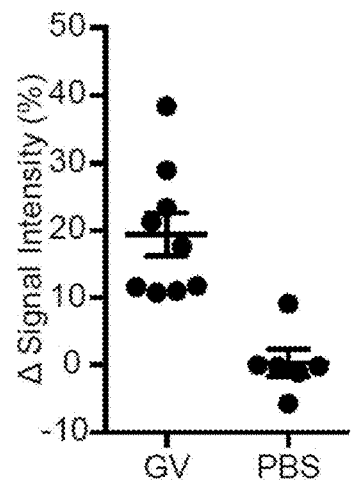
FIG. 6C shows changes in signal intensity at the sites of injection for GV and PBS (N=9 and 6 for GV and PBS, respectively, that resulted from a total of 8 mice) following ultrasound pulses, normalized by the intensity of the brain region surrounding the injection site (see methods for details).
Figure 6D:
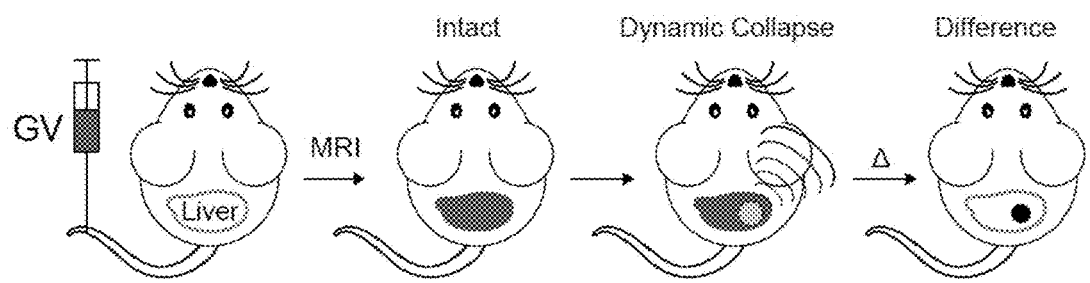
FIG. 6D shows diagram of dynamic imaging of the mouse liver after intravenous (IV) administration of GVs. 200 μL PBS with or without 13.7 nM GVs ($Ana_{AC}$, clustered form) were injected. After allowing 1 min for the liver uptake of GVs, mice were euthanized and T2*-weighted images were acquired continuously before, during and after a 5-second application of ultrasound pulses to the liver.
Figure 6E:
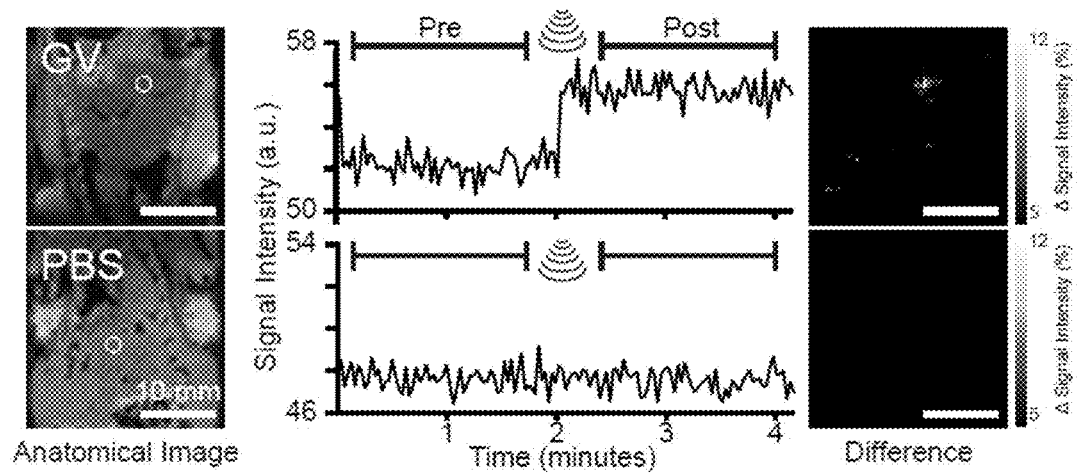
FIG. 6E shows representative anatomical image, time course and different image. Insonated spot (1 mm radius circle, dashed line labeled in anatomical image) was used for signal intensity quantification. T2*-weighted images were recorded at a rate of 1.9 sec/frame while the image intensity profile of the insonated spot (1 mm radius) was plotted. The 50 frames collected before and after insonation were averaged and subtracted to obtain the difference image.
Figure 6F:
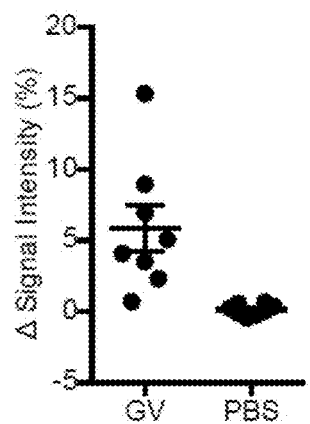
FIG. 6F shows average signal intensity change in the insonated region upon the application of focused ultrasound to the liver tissue (N=16 spots in 8 mice). Error bars represent SEM.
Figure 7A:
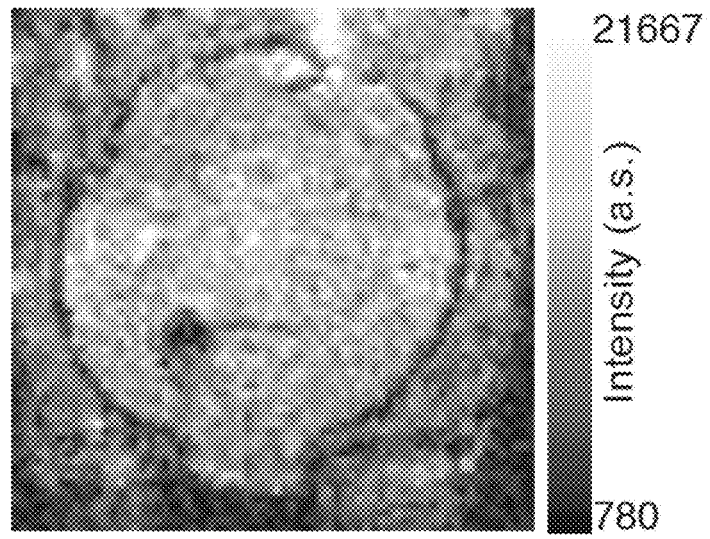
FIGS. 7A-B show an exemplary quantitative susceptibility mapping (QSM) of GV-based contrast in vivo.
Figure 7B:
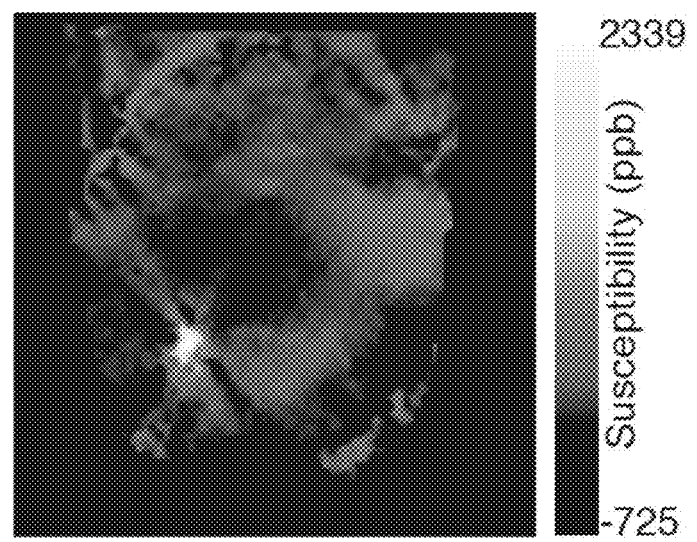

To test the acoustically modulated imaging paradigm in vivo, Ana GVs were stereotaxically injected in the striatum of adult C57 mice and imaged them using T2*-weighted MRI (FIG. 6A). We then collapsed the GVs in situ using brief pulses of MRI-guided focused ultrasound [63] and acquired a post-collapse MRI image. The resulting differential image, overlaid on a separately acquired anatomical reference, shows specific background-free contrast from the brain region injected with GVs (FIG. 6B). A contralateral injection of phosphate-buffered saline (PBS) without GVs, subjected to the same MRI and ultrasound pulses, produced no significant contrast. The mean collapse-dependent contrast in the GV-injected region was 19.4±3.2% (Mean±SEM, N=9) compared to 0.3±2.0% for PBS (Mean±SEM, N=6, p=0.0002, unpaired t-test). Although we mainly used T2*-weighted images for in vivo background-free imaging due to their convenience, QSM-processed susceptibility maps also visualized GVs with a high contrast-to-noise ratio (FIGS. 7A-B).

Example 3: Acoustically Modulated Multiplexed Imaging

Figure 8A:
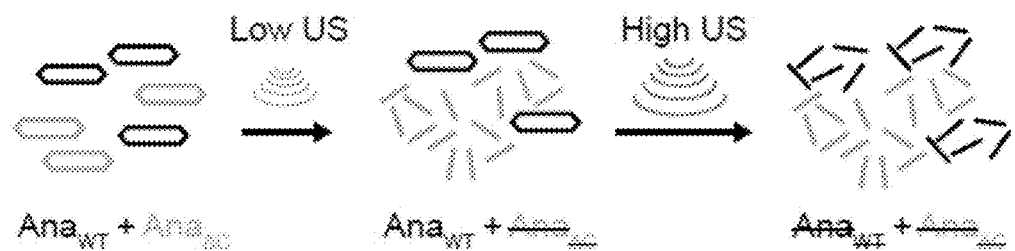
FIGS. 8A-G show an exemplary embodiment of acoustically multiplexed magnetic resonance imaging.

Acoustically modulated reporters allow an alternative multiplexing strategy based on their differential response to ultrasound. In particular, GVs with different protein composition collapse at substantially different acoustic pressures [50, 65], which suggests the possibility of detecting them in multiplex by collapsing one population at a time with ultrasound while acquiring a sequence of MRI images (FIG. 8A). Voxel-wise intensity changes between successive images should then encode the signal corresponding to each multiplexed GV population.

Figure 8B:
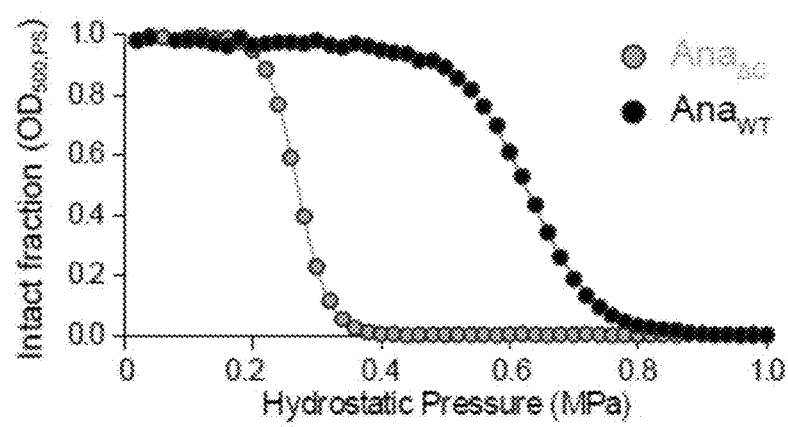
Figure 8C:
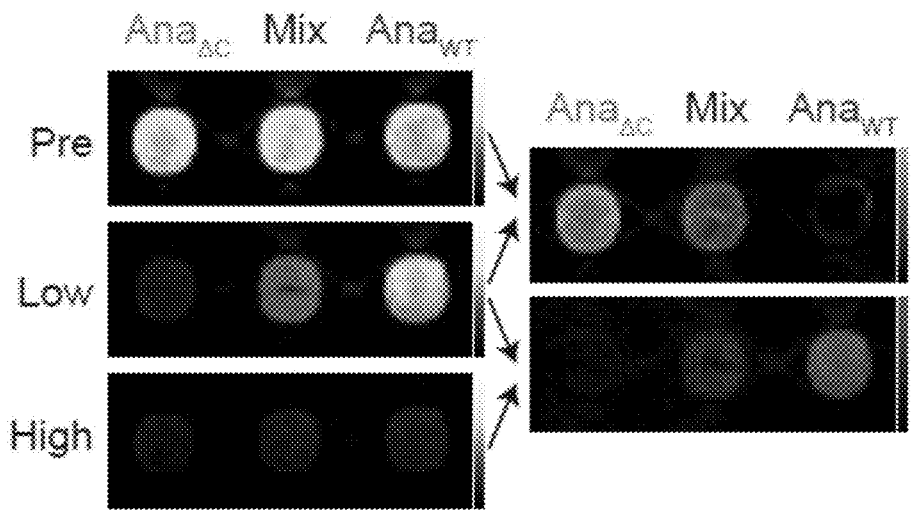
Figure 8D:
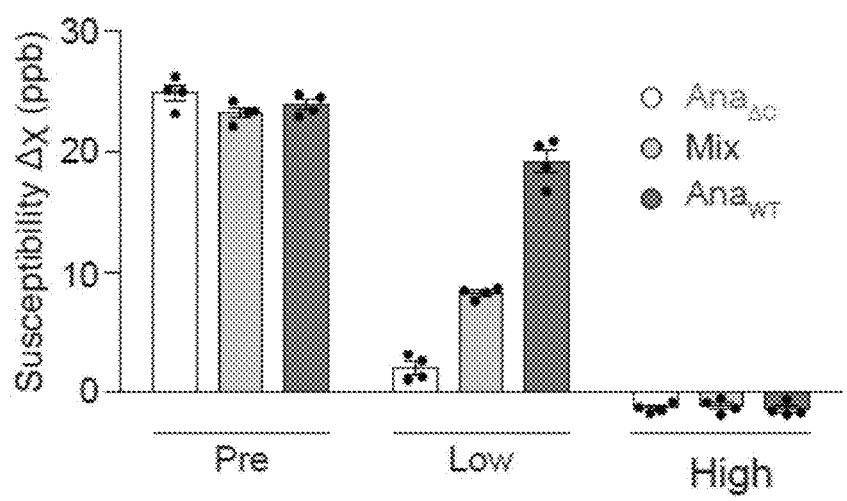
Figure 8E:
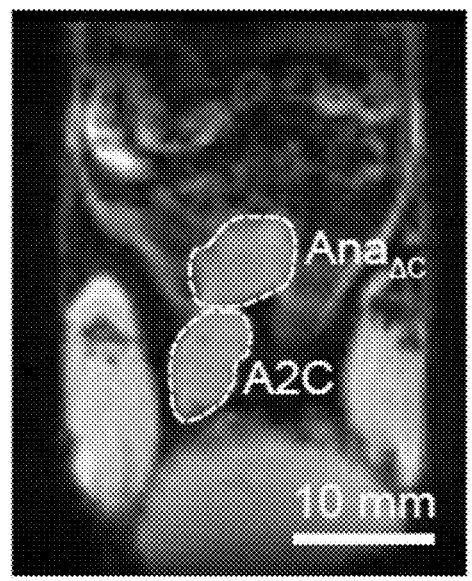
Figure 8F:
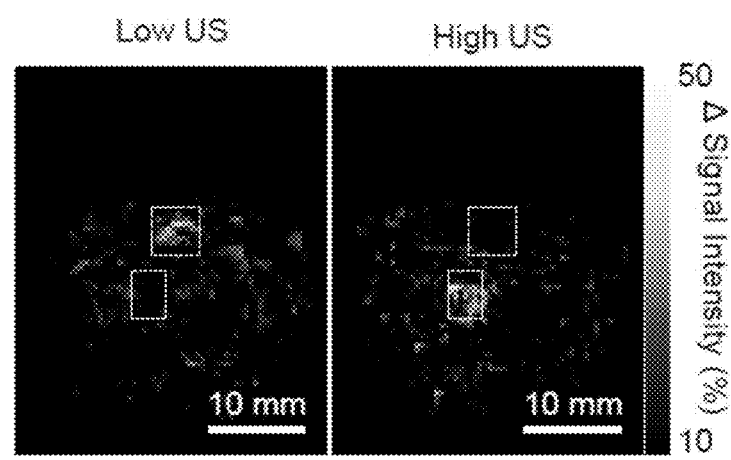
Figure 8G:
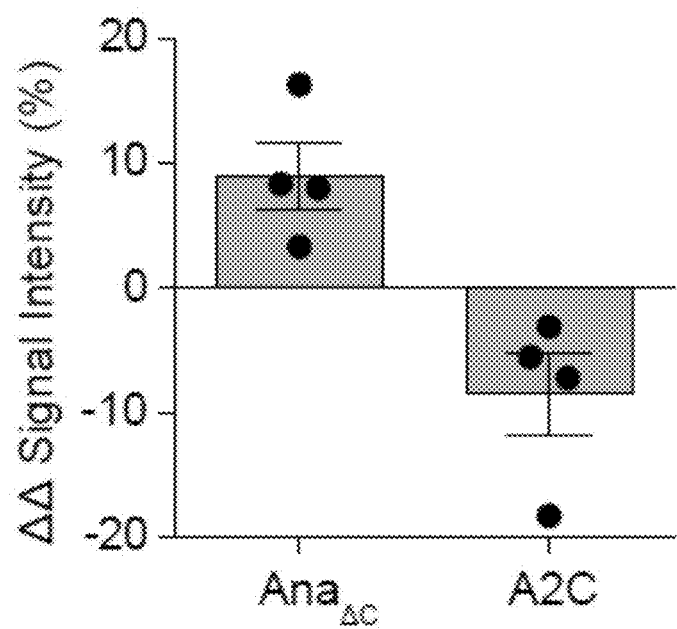

GVs with different collapse pressures can be obtained by isolating genetically distinct variants from multiple host organisms or by modifying the composition of a given GV type through genetic or chemical treatment [50, 66]. Here, we used a variant of Ana GVs (referred to as $Ana_{\Delta C}$) whose collapse pressure has been lowered by removing its outer scaffolding protein, GvpC[50] (FIG. 8B). Since GvpC removal does not alter the size or shape of the GV, $Ana_{\Delta C}$ produces MRI contrast equivalent to wildtype Ana GVs ($Ana_{WT}$). To demonstrate acoustically modulated multiplexing, we prepared a phantom with three wells containing $Ana_{\Delta C}$, $Ana_{WT}$ and a 1:1 mixture of these two GV variants (FIG. 8C). We then acquired three sequential MRI images interspersed by ultrasonic pulses at $Ana_{\Delta C}$- and $Ana_{WT}$-collapsing pressures. Changes in the measured magnetic susceptibility of each voxel between the relevant pairs of images revealed the specific GVs content of each sample (FIG. 8C-D).

Example 4: Multiparametric MRI Multiplexing

In addition to acoustic multiplexing, GVs from distinct genetic origins, which have different shapes and sizes, could be distinguished on the basis of their differential effects on T2 and QSM contrast. in particular differences in GV morphology (FIG. 9A) were expected to result in different nanoscale magnetic field patterns for a given quantity of gas, which can in turn alter the efficiency of aqueous T2 relaxation [67-71].

In contrast, the magnetic susceptibility calculated from QSM were expected to report a value primarily dependent on the total amount of air in the sample, independent of its nanoscale arrangement. Each type of GV should therefore have its own parametric fingerprint.

Figure 9A:
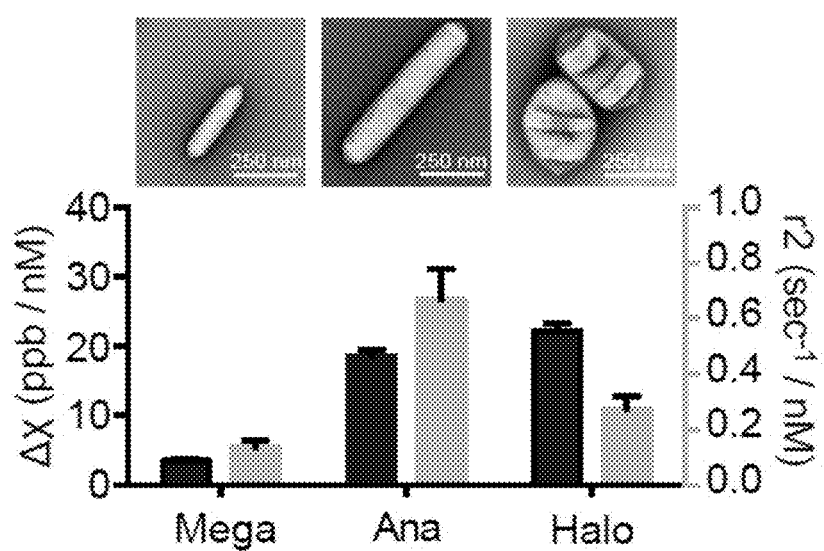
FIGS. 9A-C show an exemplary embodiment of multi-parametric fingerprinting for multiplexed magnetic resonance imaging.
Figure 9B:
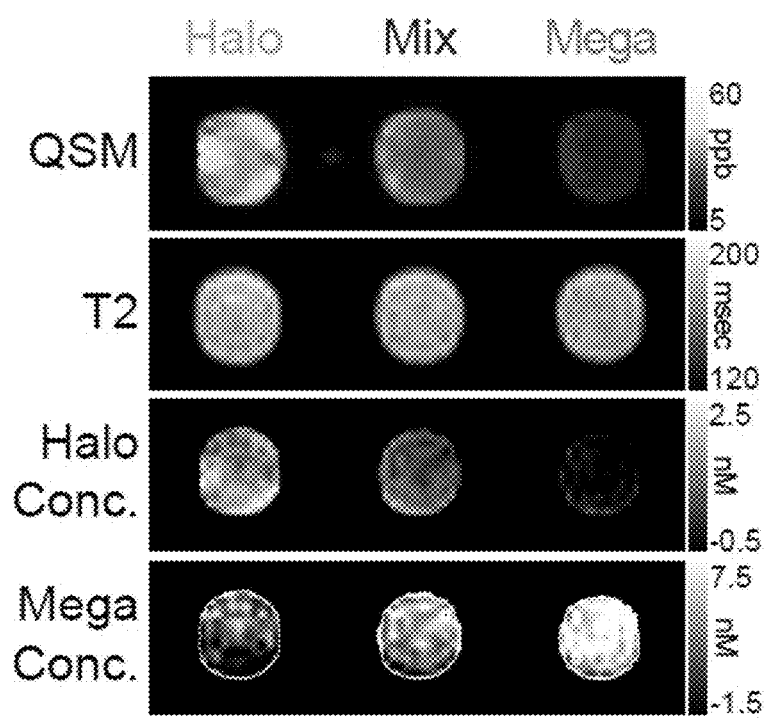
Figure 9C:
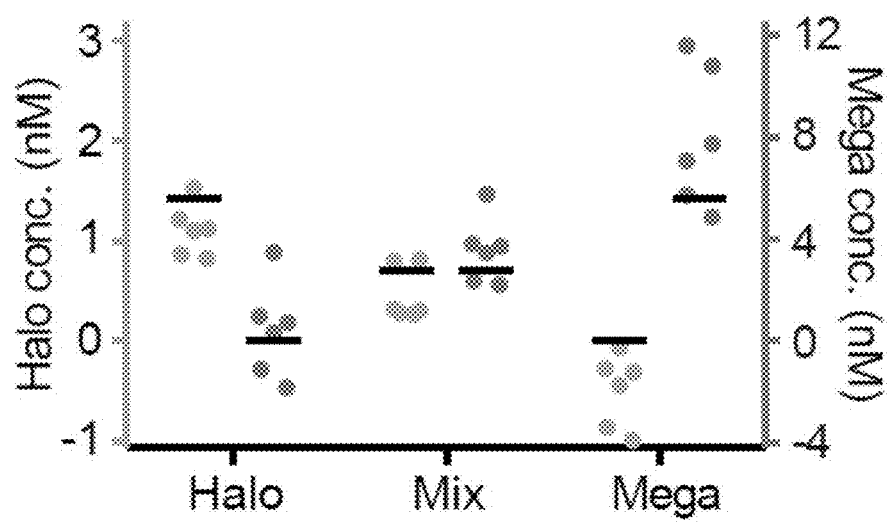

This hypothesis was tested using Ana GVs, GVs purified from *E. coli* expressing a GV gene cluster from *Bacillus megaterium* (Mega)[33] and GVs purified from *Halobacterium salinarum* (Halo) (FIG. 9A). After measuring the T2 relaxivity and molar susceptibility values for each molecule (FIG. 9A), Mega and Halo GVs were used to demonstrate multiplexed imaging. Each GV type had a distinct appearance under susceptibility contrast relative to its T2 relaxivity (FIG. 9B), and voxel-wise unmixing of susceptibility ($\Delta\chi$) and relaxation rate (R2) according the equation $$\begin{pmatrix} R_{2,obs} \\ \Delta\chi_{obs} \end{pmatrix} = \begin{pmatrix} r_{2,\alpha} & r_{2,\beta} \\ \Delta\chi_\alpha & \Delta\chi_\beta \end{pmatrix} \cdot \begin{pmatrix} c_\alpha \\ c_\beta \end{pmatrix} \quad \text{(Eq. 16)}$$

revealed the quantities of the two GV types in each sample, $C_\alpha$ and $C_\beta$ (FIG. 9C). This multiparametric MRI paradigm [72] has the advantage of being non-destructive compared to acoustic multiplexing.

Example 5: Clustering-Based Molecular Sensors

Given their size and magnetic character, GVs are in the so-called motional averaging regime [67, 70, 77, 78] of T2/T2* relaxation, where relaxation rates are expected to increase with larger particle size, provided that water access remains unaltered.

Figure 10A:
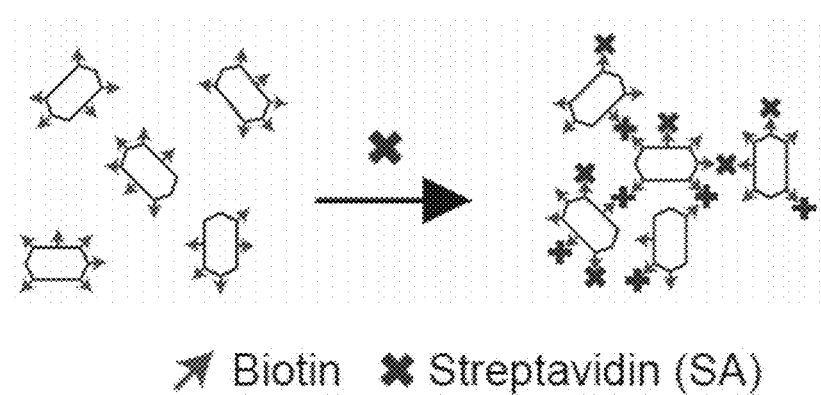
FIGS. 10A-G show an exemplary embodiment of clustering-based molecular sensors.
Figure 10B:
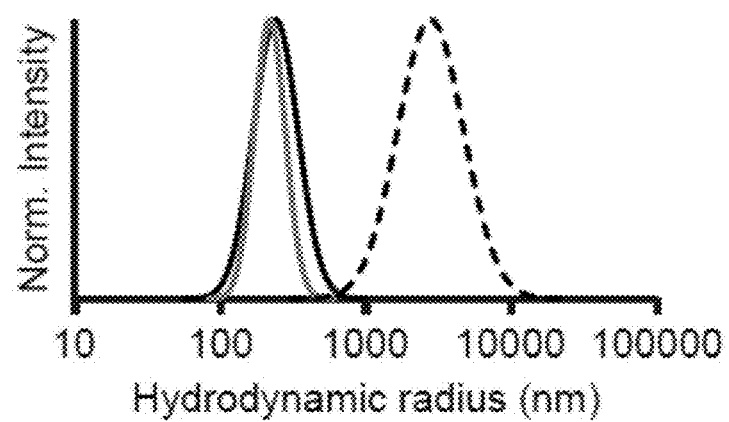
Figure 10C:
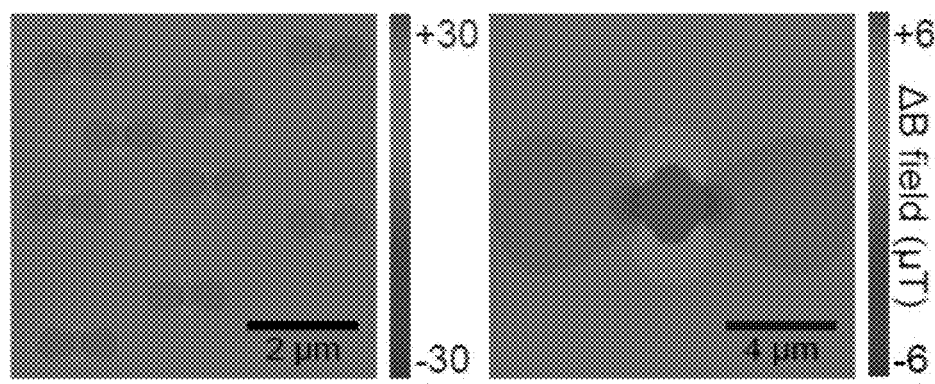
Figure 10D:
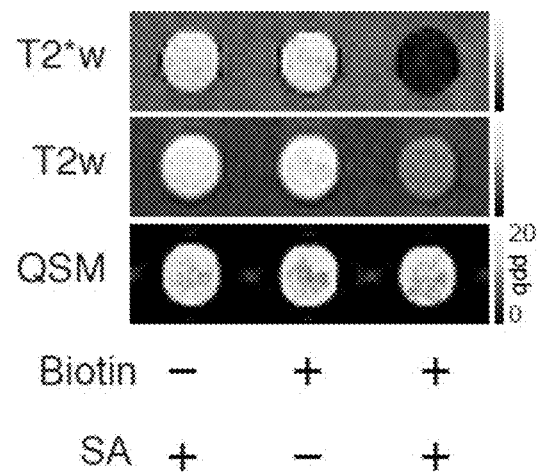
Figure 10E:
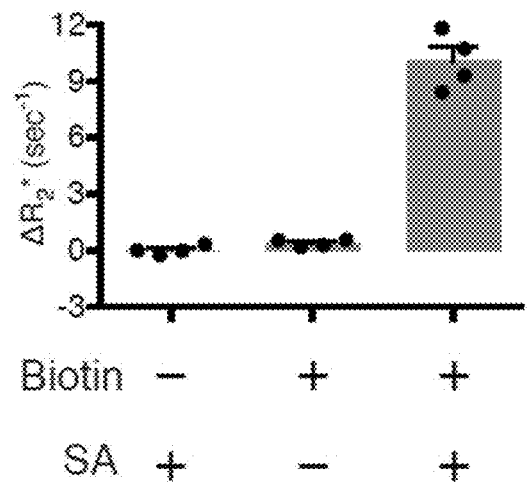
Figure 10F:
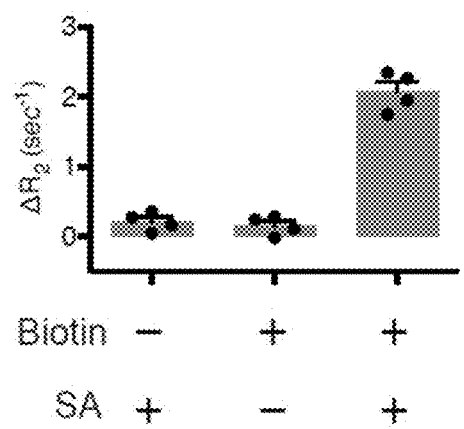
Figure 10G:
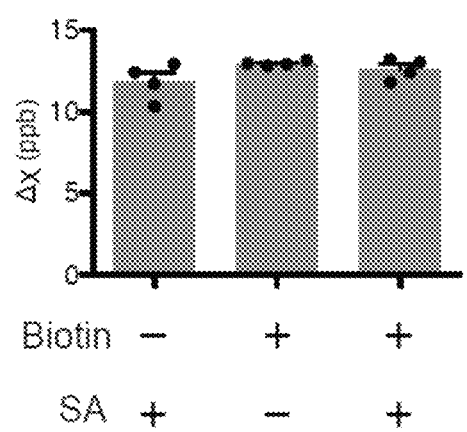

Therefore it was hypothesized that the clustering of GVs in response to a target analyte would result in an increase in both T2* and T2 relaxivity. This hypothesis was tested using biotin-functionalized Ana GVs mixed with tetrameric streptavidin (FIG. 10A, and FIGS. 11A-E). At appropriate streptavidin concentrations, GVs form micron-size clusters (FIG. 10B), which are predicted by finite element modelling to produce a magnetic field profile with correspondingly large spatial dimensions (FIG. 10C). Upon clustering, T2*- and T2-weighted images showed dramatic relaxation enhancement compared to control samples that lacked either biotinylation or streptavidin (FIG. 10D, and FIGS. 11A-E), with R2* and R2 increasing approximately 15- and 5-fold, respectively (FIGS. 10E-F). Remarkably, the QSM image was largely unaltered, as expected given the conservation of total air between the three samples; this allows a change in clustering to be distinguished from an increase in the number of particles, thereby enhancing sensing robustness.

Example 6: Theoretical Consideration of the T2/T2* Relaxation Produced by Gas Vesicles Relaxation theory[67, 68, 78] describes the T2/T2* relaxation of water near a contrast agent in three primary regimes: (1) the motional averaging regime, where $\Delta\omega_r \cdot \tau_D \ll 1$; (2) the static dephasing regime, where $\Delta\omega_r \cdot \tau_D \gg 1$; and (3) the intermediate regime, where $\Delta\omega_r \cdot \tau_D \sim 1$. Here $\Delta\omega_r$ is the root-mean-square frequency shift at the surface of the contrast agent and TD is the time for a water molecule to diffuse across the distance of the contrast agent's radius. Considering a single gas vesicle (GV) at high field (FIG. 2 panel b), we obtain $\Delta\omega_r \approx \Delta\chi \cdot \gamma B_0 \approx 10^3$ Hz and $\tau_D \approx 10^{-6}$ sec; therefore T2/T2* relaxation on the nanoscale (e.g., everywhere inside an agarose well containing GVs) occurs in the motional averaging regime. At the same time, the macroscale $\Delta B$ field around a millimeter-sized agarose well containing GVs (at a volume fraction of ~0.01%) (FIG. 2 panel c) has a predicted $\Delta\omega_r \approx 10^{-1}$ Hz and $\tau_D \approx 10^3$ sec, resulting in T2/T2* relaxation in the static dephasing regime.

These relaxation regimes are manifest in the T2-weighted and T2*-weighted images shown in FIGS. 3A-D. The spin relaxation at the center of the well is predominantly a result of the nanoscale $\Delta B$ field. On the other hand, the spin relaxation near the rim of the wells results from the macroscale $\Delta B$ field. The rim appears darker than the center of the well in the T2* image because relaxation is more efficient in the static dephasing regime than motional averaging regime. However, T2 relaxation in the static dephasing regime is minimal because the $\pi$ pulse can effectively refocus the dephasing, which explains the lack of hypointensity at the rim of the wells in T2-weighted images.

Relaxation theory also helps explain the behavior of clustered GVs because their micron-size clusters are predicted to have $\tau_D \approx 10^{-3}$ sec, which brings them from the motional averaging regime to the intermediate regime, resulting in strong enhancement of both T2* and T2 relaxation (FIGS. 10E-F).

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional gas vesicles, related components, genetic or chemical variants, as well as in compositions, methods and systems herein described, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. He, X. and D. A. Yablonskiy, *Biophysical mechanisms of phase contrast in gradient echo MRI*. Proceedings of the National Academy of Sciences, 2009. 106(32): p. 13558-13563.

2. Shaner, N. C., et al., *A bright monomeric green fluorescent protein derived from Branchiostoma lanceolatum*. Nat Meth, 2013. 10(5): p. 407-409.
3. Caravan, P., et al., *Gadolinium(III) Chelates as MRI Contrast Agents: Structure, Dynamics, and Applications*. Chemical Reviews, 1999. 99(9): p. 2293-2352.
4. Lee, J.-H., et al., *Artificially engineered magnetic nanoparticles for ultra-sensitive molecular imaging*. Nat Med, 2007. 13(1): p. 95-99.
5. Weissleder, R., et al., *Ultrasmall superparamagnetic iron oxide: characterization of a new class of contrast agents for MR imaging*. Radiology, 1990. 175(2): p. 489-493.
6. Genove, G., et al., *A new transgene reporter for in vivo magnetic resonance imaging*. Nat Med, 2005. 11(43): p. 450-454.
7. Cohen, B., et al., *Ferritin as an Endogenous MRI Reporter for Noninvasive Imaging of Gene Expression in C6 Glioma Tumors*. Neoplasia, 2005. 7(2): p. 109-117.
8. Shapiro, M. G., et al., *Directed evolution of a magnetic resonance imaging contrast agent for noninvasive imaging of dopamine*. Nat Biotech, 2010. 28(3): p. 264-270.
9. Cohen, B., et al., *MRI detection of transcriptional regulation of gene expression in transgenic mice*. Nat Med, 2007. 13(4): p. 498-503.
10. Gilad, A. A., et al., *Artificial reporter gene providing MRI contrast based on proton exchange*. Nat Biotech, 2007. 25(2): p. 217-219.
11. Zhang, S., et al., *PARACEST Agents: Modulating MRI Contrast via Water Proton Exchange*. Accounts of Chemical Research, 2003. 36(10): p. 783-790.
12. Taratula, O. and I. J. Dmochowski, *Functionalized 129Xe contrast agents for magnetic resonance imaging*. Current Opinion in Chemical Biology, 2010. 14(1): p. 97-104.
13. Evbuomwan, O. M., et al., *CEST and PARACEST Agents for Molecular Imaging*, in *The Chemistry of Molecular Imaging*. 2014, John Wiley & Sons, Inc. p. 225-243.
14. Kislukhin, A. A., et al., *Paramagnetic fluorinated nanoemulsions for sensitive cellular fluorine-19 magnetic resonance imaging*. Nat Mater, 2016. advance online publication.
15. Walsby, A. E., *Gas vesicles*. Microbiol. Rev., 1994. 58(1): p. 94-144.
16. Walsby, A. E., *Gas-vacuolate bacteria (apart from cyanobacteria)*, in *The Prokaryotes*. 1981, Springer. p. 441-447.
17. Walsby, A. E., *Cyanobacteria: planktonic gas-vacuolate forms*. The Prokaryotes, a Handbook on Habitats, Isolation, and Identification of Bacteria, 2013. 1: p. 224-235.
18. Woese, C. R., *Bacterial evolution*. Microbiological reviews, 1987. 51(2): p. 221.
19. Walsby, A. E., *Gas vesicles*. Microbiol Rev, 1994. 58(1): p. 94-144.
20. Terreno, E., et al., *Challenges for Molecular Magnetic Resonance Imaging*. Chemical Reviews, 2010. 110(5): p. 3019-3042.
21. Cunningham, C. H., et al., *Positive contrast magnetic resonance imaging of cells labeled with magnetic nanoparticles*. Magnetic Resonance in Medicine, 2005. 53(5): p. 999-1005.
22. Hayes, P. and R. Powell, *The gvpA/C cluster of Anabaena flos-aquae has multiple copies of a gene encoding GvpA*. Archives of microbiology, 1995. 164(1): p. 50-57.
23. Kinsman, R. and P. Hayes, *Genes encoding proteins homologous to halobacterial Gvps N, J, K, F & L are located downstream of gvpC in the cyanobacterium Anabaena flos-aquae*. DNA Sequence, 1997. 7(2): p. 97-106.
24. Pfeifer, F., *Distribution, formation and regulation of gas vesicles*. Nat. Rev. Microbiol., 2012. 10(10): p. 705-15.
25. Yi, G., S.-H. Sze, and M. R. Thon, *Identifying clusters of functionally related genes in genomes*. Bioinformatics, 2007. 23(9): p. 1053-1060.
26. Pfeifer, F., *Distribution, formation and regulation of gas vesicles*. Nat Rev Microbiol, 2012. 10(10): p. 705-15.
27. Myers, E. W. and W. Miller, *Optimal alignments in linear space*. Computer applications in the biosciences: CABIOS, 1988. 4(1): p. 11-17.
28. Smith, T. F. and M. S. Waterman, *Comparison of biosequences*. Advances in applied mathematics, 1981. 2(4): p. 482-489.
29. Needleman, S. B. and C. D. Wunsch, *A general method applicable to the search for similarities in the amino acid sequence of two proteins*. Journal of molecular biology, 1970. 48(3): p. 443-453.
30. Pearson, W. R. and D. J. Lipman, *Improved tools for biological sequence comparison*. Proceedings of the National Academy of Sciences, 1988. 85(8): p. 2444-2448.
31. Karlin, S. and S. F. Altschul, *Methods for assessing the statistical significance of molecular sequence features by using general scoring schemes*. Proceedings of the National Academy of Sciences, 1990. 87(6): p. 2264-2268.
32. Karlin, S. and S. F. Altschul, *Applications and statistics for multiple high-scoring segments in molecular sequences*. Proceedings of the National Academy of Sciences, 1993. 90(12): p. 5873-5877.
33. Li, N. and M. C. Cannon, *Gas vesicle genes identified in Bacillus megaterium and functional expression in Escherichia coli*. J Bacteriol, 1998. 180(9): p. 2450-8.
34. Maresca, D., et al., *Nonlinear Ultrasound Imaging of Nanoscale Acoustic Biomolecules*. Applied Physics Letters, 2017. 110(7).
35. Shapiro, M. G., et al., *Biogenic gas nanostructures as ultrasonic molecular reporters*. Nat. Nanotechnol., 2014. 9(4): p. 311-316.
36. Dawson, P. E., et al., *Synthesis of proteins by native chemical ligation*. Science, 1994. 266(5186): p. 776-780.
37. Nilsson, B. L., M. B. Soellner, and R. T. Raines, *Chemical synthesis of proteins*. Annu. Rev. Biophys. Biomol. Struct., 2005. 34: p. 91-118.
38. Zordan, R. E., et al., *Avoiding the ends: internal epitope tagging of proteins using transposon Tn7*. Genetics, 2015. 200(1): p. 47-58.
39. Walsby, A. E., *Gas vesicles*. Microbiological Reviews, 1994. 58(1): p. 94-144.
40. Shapiro, M. G., et al., *Genetically encoded reporters for hyperpolarized xenon magnetic resonance imaging*. Nat Chem, 2014. 6(7): p. 629-34.
41. Schindelin, J., et al., *Fiji: an open-source platform for biological-image analysis*. Nat Meth, 2012. 9(7): p. 676-682.
42. Walsby, A. E. and R. E. Armstrong, *Average thickness of the gas vesicle wall in Anabaena flos-aquae*. Journal of Molecular Biology, 1979. 129(2): p. 279-285.
43. SIMON, R. D., *Morphology and Protein Composition of Gas Vesicles from Wild Type and Gas Vacuole Defective Strains of Halobacterium salinarium Strain 5*. Microbiology, 1981. 125(1): p. 103-111.
44. Hayes, P. K., A. E. Walsby, and J. E. Walker, *Complete amino acid sequence of cyanobacterial gas-vesicle protein indicates a 70-residue molecule that corresponds in size to the crystallographic unit cell*. Biochemical Journal, 1986. 236(1): p. 31-36.

45. Fischer, H., I. Polikarpov, and A. F. Craievich, *Average protein density is a molecular-weight-dependent function*. Protein Science, 2004. 13(10): p. 2825-2828.
46. Abdul-Rahman, H. S., et al., *Fast and robust three-dimensional best path phase unwrapping algorithm*. Applied Optics, 2007. 46(26): p. 6623-6635.
47. Schweser, F., et al., *Quantitative imaging of intrinsic magnetic tissue properties using MRI signal phase: An approach to in vivo brain iron metabolism?* NeuroImage, 2011. 54(4): p. 2789-2807.
48. Tang, J., et al., *SWIM: Susceptibility Mapping as a Means to Visualize Veins and Quantify Oxygen Saturation*, in *Susceptibility Weighted Imaging in MRI*. 2011, John Wiley & Sons, Inc. p. 461-485.
49. Cherin, E., et al., *Acoustic behavior of Halobacterium salinarum gas vesicles in the high frequency range: experiments and modeling*. 2016. submitted.
50. Lakshmanan, A., et al., *Molecular Engineering of Acoustic Protein Nanostructures*. ACS Nano, 2016.
51. Choi, J. J., et al., *Noninvasive, transcranial and localized opening of the blood-brain barrier using focused ultrasound in mice*. Ultrasound in Medicine & Biology, 2007. 33(1): p. 95-104.
52. Meeker, D., *Finite element method magnetics*. FEMM, 2010. 4: p. 32.
53. Brown, R. W., et al., *Magnetic resonance imaging: physical principles and sequence design*. 2014: John Wiley & Sons.
54. Haacke, E. M., et al., *Susceptibility-Weighted Imaging: Technical Aspects and Clinical Applications, Part 1*. American Journal of Neuroradiology, 2009. 30(1): p. 19-30.
55. Wang, Y. and T. Liu, *Quantitative susceptibility mapping (QSM): Decoding MRI data for a tissue magnetic biomarker*. Magnetic Resonance in Medicine, 2015. 73(1): p. 82-101.
56. Gilad, A. A., et al., *MRI Reporter Genes*. Journal of Nuclear Medicine, 2008. 49(12): p. 1905-1908.
57. Gilad, A. A., et al., *Developing MR reporter genes: promises and pitfalls*. NMR in Biomedicine, 2007. 20(3): p. 275-290.
58. Srivastava, A. K., et al., *Advances in using MRI probes and sensors for in vivo cell tracking as applied to regenerative medicine*. Disease Models and Mechanisms, 2015. 8(4): p. 323-336.
59. Ahrens, E. T. and J. W. M. Bulte, *Tracking immune cells in vivo using magnetic resonance imaging*. Nature Reviews: Immunology, 2013. 13(10): p. 755-763.
60. Stuber, M., et al., *Positive contrast visualization of iron oxide-labeled stem cells using inversion-recovery with ON-resonant water suppression (IRON)*. Magnetic Resonance in Medicine, 2007. 58(5): p. 1072-1077.
61. Mani, V., et al., *Gradient echo acquisition for superparamagnetic particles with positive contrast (GRASP): Sequence characterization in membrane and glass superparamagnetic iron oxide phantoms at 1.5T and 3T*. Magnetic Resonance in Medicine, 2006. 55(1): p. 126-135.
62. Zurkiya, O. and X. Hu, *Off-resonance saturation as a means of generating contrast with superparamagnetic nanoparticles*. Magnetic Resonance in Medicine, 2006. 56(4): p. 726-732.
63. Jolesz, F. A., *MRI-Guided Focused Ultrasound Surgery*. Annual Review of Medicine, 2009. 60(1): p. 417-430.
64. McMahon, M. T., et al., *New "multicolor" polypeptide diamagnetic chemical exchange saturation transfer (DI-ACEST) contrast agents for MRI*. Magnetic Resonance in Medicine, 2008. 60(4): p. 803-812.
65. Shapiro, M. G., et al., *Biogenic gas nanostructures as ultrasonic molecular reporters*. Nat Nano, 2014. 9(4): p. 311-316.
66. Hayes, P. K., B. Buchholz, and A. E. Walsby, *Gas vesicles are strengthened by the outer-surface protein, GvpC*. Archives of Microbiology, 1992. 157(3): p. 229-234.
67. Yablonskiy, D. A. and E. M. Haacke, *Theory of NMR signal behavior in magnetically inhomogeneous tissues: The static dephasing regime*. Magnetic Resonance in Medicine, 1994. 32(6): p. 749-763.
68. Gillis, P., F. Moiny, and R. A. Brooks, *On T2-shortening by strongly magnetized spheres: A partial refocusing model*. Magnetic Resonance in Medicine, 2002. 47(2): p. 257-263.
69. Jensen, J. H. and R. Chandra, *NMR relaxation in tissues with weak magnetic inhomogeneities*. Magnetic Resonance in Medicine, 2000. 44(1): p. 144-156.
70. Matsumoto, Y. and A. Jasanoff, *T2 relaxation induced by clusters of superparamagnetic nanoparticles: Monte Carlo simulations*. Magnetic Resonance Imaging, 2008. 26(7): p. 994-998.
71. Bowen, C. V., et al., *Application of the static dephasing regime theory to superparamagnetic iron-oxide loaded cells*. Magnetic Resonance in Medicine, 2002. 48(1): p. 52-61.
72. Hung, A. H., et al., *Magnetic barcode imaging for contrast agents*. Magnetic resonance in medicine, 2016.
73. Perez, J. M., et al., *Magnetic relaxation switches capable of sensing molecular interactions*. Nat Biotech, 2002. 20(8): p. 816-820.
74. Zabow, G., S. J. Dodd, and A. P. Koretsky, *Shape-changing magnetic assemblies as high-sensitivity NW-readable nanoprobes*. Nature, 2015. 520(7545): p. 73-U157.
75. Atanasijevic, T., et al., *Calcium-sensitive MRI contrast agents based on superparamagnetic iron oxide nanoparticles and calmodulin*. Proceedings of the National Academy of Sciences, 2006. 103(40): p. 14707-14712.
76. Shapiro, M. G., et al., *Protein Nanoparticles Engineered to Sense Kinase Activity in MRI* Journal of the American Chemical Society, 2009. 131(7): p. 2484-2486.
77. Brooks, R. A., F. Moiny, and P. Gillis, *On T2-shortening by weakly magnetized particles: The chemical exchange model*. Magnetic Resonance in Medicine, 2001. 45(6): p. 1014-1020.
78. Gillis, P. and S. H. Koenig, *Transverse relaxation of solvent protons induced by magnetized spheres: Application to ferritin, erythrocytes, and magnetite*. Magnetic Resonance in Medicine, 1987. 5(4): p. 323-345.

The invention claimed is:
1. A contrast-enhanced magnetic resonance imaging method comprising:
 imaging a target site comprising a gas vesicle protein structure (GVPS), the GVPS containing gas having a gas susceptibility value different from a bulk material susceptibility at the target site to obtain a MRI image, the imaging comprising detecting volume susceptibilities of the target site and/or relaxation rates of nuclear spins of atoms in the bulk material; wherein the MRI image is QSM, T2, T2*, T2- or T2*-weighted map.
2. The magnetic resonance imaging method of claim 1, wherein the GVPS is a GVPS selected from a species of *Anabaena* bacteria, *Halobacterium* archaea, or *Bacillus megaterium*.

3. The magnetic resonance imaging method of claim 1, wherein the GVPS is provided in a contrast agent having a concentration equal to or lower than 100 nM.

4. The magnetic resonance imaging method of claim 1, wherein the imaging the target site obtains a series of MRI images of the target site, and the method further comprises:
detecting an increase or decrease in MRI contrast.

5. The magnetic resonance imaging method of claim 4, wherein the increase or decrease in MRI contrast is an increase or decrease in $R_2$ or $R_2^*$ relaxation rates.

6. The magnetic resonance imaging method of claim 1, wherein the GVPS is provided in a contrast agent having a concentration equal to or lower than 10 nM.

7. The magnetic resonance imaging method of claim 1, wherein the GVPS is provided in a contrast agent having a concentration equal to or lower than 1 nM.

8. The magnetic resonance imaging method of claim 1, wherein the GVPS is provided in a contrast agent and the MRI image is a first MRI image, the method further comprising
collapsing the GVPS by applying collapsing ultrasound to the target site, the collapsing ultrasound applied at a collapsing ultrasound pressure greater than a selectable acoustic collapse pressure value derived from an acoustic collapse pressure profile of the GVPS, and
after collapsing, imaging the target site to obtain a second MRI image of the target site.

9. The magnetic resonance imaging method of claim 1, wherein
the GVPS is part of a first GVPS type exhibiting a first acoustic collapse pressure profile and a first selectable acoustic collapse pressure value,
the target site further comprises a second GVPS type exhibiting a second acoustic collapse pressure profile and a second selectable acoustic collapse pressure value, and
the MRI image is a first MRI image,
the method comprising:
selectively collapsing the first GVPS type by applying collapsing ultrasound to the target site, the collapsing ultrasound applied at a first acoustic collapse pressure value equal to or higher than the first selectable acoustic collapse pressure value and lower than the second selectable acoustic collapse pressure value; and
imaging the target site containing at least the second, uncollapsed GVPS type to obtain a second MRI image of the target site.

10. The magnetic resonance imaging method of claim 8, wherein the collapsing ultrasound pressure is higher than a midpoint collapse pressure of the GVPS.

11. The magnetic resonance imaging method of claim 8, wherein the collapsing ultrasound pressure is higher than a complete collapse pressure of the GVPS.

12. The magnetic resonance imaging method of claim 8, wherein the GVPS comprise a GvpC protein selected from the group consisting of ΔGvpC, ΔN&C, and GvpCWT, and the selectable acoustic collapse pressure value is 571 kPa for ΔGvpC, 657 kPa for ΔN&C, and 869 kPa for GvpCWT.

13. The magnetic resonance imaging method of claim 8, further comprising subtracting the second MRI image from the first MRI image to provide a background-free magnetic resonance imaging of the target site.

14. The magnetic resonance imaging method of claim 9, further comprising, after imaging the target site containing at least the second, uncollapsed GVPS type,
selectively collapsing the second gas vesicle structure type by applying collapsing ultrasounds to the target site, the collapsing ultrasounds applied at a second acoustic collapse pressure value equal to or higher than the second selectable acoustic collapse pressure value of the second GVPS type.

15. The magnetic resonance imaging method of claim 9, further comprising:
after selectively collapsing the second GVPS type, imaging the target site by applying an external magnetic field to the target site.

16. The magnetic resonance imaging method of claim 9, wherein the first GVPS type and the second GVPS type are selected from GVPS types species of *Anabaena* bacteria and *Halobacterium* bacteria.

17. The magnetic resonance imaging method of claim 9, wherein the first GVPS type comprises ΔGvpC and the second GVPS type comprises ΔN&C, and the selectable acoustic collapse pressure value is 630 kPa.

18. The magnetic resonance imaging method of claim 9, wherein the acoustic collapse pressure value of the first gas vesicle protein structure type is selected from the acoustic collapse pressure profile at a value between 0.05% and 95% collapse.

19. The magnetic resonance imaging method of claim 9, wherein the acoustic collapse pressure value of the first GVPS type is selected from the acoustic collapse pressure profile at a value of 50% collapse.

20. The magnetic resonance imaging method of claim 9, wherein the acoustic collapse pressure value of the first GVPS type is selected from the acoustic collapse pressure profile at a value that optimally maximizes collapse of the first GVPS type while minimizing collapse of the second GVPS type.

21. The magnetic resonance imaging method of claim 20, wherein the optimally maximizing collapse of the first GVPS type while minimizing collapse of the second GVPS type is determined by maximizing f1(p)−f2(p), wherein $f1(p)=(1+e^{(p-p_c)/\Delta p})^{-1}$ and $f2(p)=(1+e^{(p-p_c)/\Delta p})^{-1}$ and f1(p) and f2(p) correspond to an acoustic collapse profile of the first GVPS and the second GVPS, respectively.

22. A contrast-enhanced magnetic resonance imaging method comprising:
imaging a target site comprising a gas vesicle protein structure (GVPS), the GVPS containing gas having a gas susceptibility value different from a bulk material susceptibility at the target site to obtain a MRI image, the imaging comprising detecting volume susceptibilities of the target site and/or relaxation rates of nuclear spins of atoms in the bulk material, wherein the gas susceptibility is different from the bulk material susceptibility by at least 3 ppm.

23. The magnetic resonance imaging method of claim 21, wherein the MRI image is QSM, T2, T2*, T2- or T2*-weighted map.

24. The magnetic resonance imaging method of claim 22, wherein the GVPS is provided in a contrast agent having a concentration equal to or lower than 100 nM.

25. The magnetic resonance imaging method of claim 22, wherein the GVPS is provided in a contrast agent and the MRI image is a first MRI image, the method further comprising
collapsing the GVPS by applying collapsing ultrasound to the target site, the collapsing ultrasound applied at a collapsing ultrasound pressure greater than a selectable acoustic collapse pressure value derived from an acoustic collapse pressure profile of the GVPS, and after collapsing, imaging the target site to obtain a second MRI image of the target site.

26. A contrast-enhanced magnetic resonance imaging method comprising:

imaging a target site comprising a gas vesicle protein structure (GVPS), the GVPS containing gas having a gas susceptibility value different from a bulk material susceptibility at the target site to obtain a MRI image, the imaging comprising detecting volume susceptibilities of the target site and/or relaxation rates of nuclear spins of atoms in the bulk material, wherein the imaging the target site obtains a series of MRI images of the target site, and detecting an increase or decrease in MRI contrast, wherein the increase or decrease in MRI contrast is an increase or decrease in $R_2$ or $R_2^*$ relaxation rates.

27. A contrast-enhanced magnetic resonance imaging method comprising:

imaging a target site comprising a gas vesicle protein structure (GVPS), the GVPS containing gas having a gas susceptibility value different from a bulk material susceptibility at the target site to obtain a MRI image, the imaging comprising detecting volume susceptibilities of the target site and/or relaxation rates of nuclear spins of atoms in the bulk material, wherein the GVPS is provided in a contrast agent;

further imaging the GVPS through an imaging ultrasound applied an imaging ultrasound pressure lower than a selectable acoustic collapse pressure value of the GVPS, thus forming an ultrasound image in addition to the MRI image; and forming an enhanced image from the MRI image and the ultrasound image.

28. The magnetic resonance imaging method of claim 27, wherein the first and second MRI images are selected from the group consisting of QSM, T2, T2*, T2- or T2*-weighted map.

29. A contrast-enhanced magnetic resonance imaging method comprising:

imaging a target site comprising a gas vesicle protein structure (GVPS), the GVPS containing gas having a gas susceptibility value different from a bulk material susceptibility at the target site to obtain a MRI image, the imaging comprising detecting volume susceptibilities of the target site and/or relaxation rates of nuclear spins of atoms in the bulk material, wherein the GVPS is part of a first GVPS type;

establishing a parameter fingerprint type comprising a ratio of at least two parameters selected from susceptibility, T2 relaxivity, and T2* relaxivity;

additionally administering to the target site a second gas vesicle protein structure (GVPS) type, the first GVPS type having a first value for a parameter fingerprint type and the second GVPS type having a second value for the parameter fingerprint type, the first value being different than the second value; and measuring from the imaging the at least two parameters of the parameter fingerprint type to obtain measured parameters.

30. The magnetic resonance imaging method of claim 29, further comprising:

processing the MRI image using voxel-wise unmixing of the parameters of the first GVPS type and the parameters of the second GVPS type with the measured parameters to obtain an unmixed MRI image of concentrations of the first GVPS type and concentrations of the second GVPS type.

31. The magnetic resonance imaging method of claim 29, wherein the parameter fingerprint comprises susceptibility and T2 relaxivity and the imaging the target site comprises QSM and T2 imaging.

32. The magnetic resonance imaging method of claim 29, wherein the parameter fingerprint comprises susceptibility and T2* relaxivity and the imaging the target site comprises QSM and T2* imaging.

33. The magnetic resonance imaging method of claim 29, wherein the parameter fingerprint comprises susceptibility, T2 relaxivity, and T2* relaxivity and the imaging the target site comprises QSM, T2 imaging, and T2* imaging.

* * * * *